United States Patent [19]

Duggan et al.

[11] Patent Number: 5,294,616

[45] Date of Patent: Mar. 15, 1994

[54] FIBRINOGEN RECEPTOR ANTAGONISTS

[75] Inventors: Mark E. Duggan, Narberth; Melissa S. Egbertson, Ambler; Wasyl Halczenko, Hatfield; George D. Hartman, Lansdale; Laura M. Turchi, Broomall; William L. Laswell, Perkasie, all of Pa.

[73] Assignee: Merck & Co., Inc., Rahway, N.J.

[21] Appl. No.: 857,528

[22] Filed: Mar. 25, 1992

Related U.S. Application Data

[63] Continuation-in-part of Ser. No. 750,645, Aug. 30, 1991, abandoned, which is a continuation-in-part of Ser. No. 589,299, Sep. 27, 1990, abandoned.

[51] Int. Cl.$^5$ .............. A61K 31/495; A61K 31/675; A61K 31/445; C07D 295/00; C07D 211/22; C07D 211/30; C07D 277/62; C07D 307/02
[52] U.S. Cl. .................... 514/255; 514/80; 514/82; 514/85; 514/183; 514/210; 514/211; 514/299; 514/311; 514/326; 514/331; 514/385; 514/377; 514/391; 514/394; 514/461; 514/428; 514/513; 514/545; 514/547; 514/549; 514/561; 514/562; 514/599; 514/609; 514/501; 514/529; 514/530; 514/533; 514/616; 514/563; 544/398; 544/400; 544/232; 546/112; 546/221; 546/23; 546/162; 546/227; 546/233; 546/248; 546/276; 548/175; 548/567; 548/568; 548/950; 549/487; 558/391; 558/170; 560/9; 560/29; 560/41; 560/106; 560/107; 560/119; 560/122; 560/125; 560/168; 562/501; 562/504; 562/507; 562/125
[58] Field of Search .............. 560/41, 106, 107, 119, 560/122, 125, 450, 29, 9, 168, 41, 107; 562/501, 504, 507, 125; 514/510, 529, 530, 533, 255, 326, 183, 210, 212, 82, 85, 80, 299, 331, 311, 385, 391, 394, 377, 461, 428, 513, 529, 545, 547, 549, 561, 562, 599, 609, 616; 544/398, 400, 232, 221, 23, 162, 281, 568; 546/112, 227, 233, 248, 276, 221; 548/175, 567, 950; 549/487; 558/391

[56] References Cited

U.S. PATENT DOCUMENTS

| | | | |
|---|---|---|---|
| 4,004,008 | 1/1977 | Makovec et al. | 424/250 |
| 4,122,255 | 10/1992 | Krapcho | 544/160 |
| 4,243,807 | 1/1981 | Friebe et al. | 546/232 |
| 4,622,331 | 11/1986 | Jozic | 514/331 |
| 5,030,654 | 7/1991 | Barnish | 546/232 |

FOREIGN PATENT DOCUMENTS

| | | |
|---|---|---|
| 0381033 | 8/1990 | European Pat. Off. |
| 0384362 | 8/1990 | European Pat. Off. |
| 449079-A | 10/1991 | European Pat. Off. |

OTHER PUBLICATIONS

Merck Index, 10th Edition, paragraph 9301, Tiropramide, (1985).

*Primary Examiner*—Cecilia Tsang
*Attorney, Agent, or Firm*—Richard S. Parr; Melvin Winokur; Paul D. Matukaitis

[57] ABSTRACT

A series of non-peptide derivatives that are antagonists of the fibrinogen IIb/IIIa receptor and thus are platelet aggregation compounds useful in the prevention and treatment of diseases caused by thrombus formation.

16 Claims, No Drawings

FIBRINOGEN RECEPTOR ANTAGONISTS

CROSS-REFERENCE

This application is a continuation-in-part application of U.S. Ser. No. 07/750,645, filed Aug. 30, 1991, now abandoned which is a continuation-in-part application of U.S. Ser. No. 589,299, filed Sep. 27, 1990 now abandoned.

BACKGROUND OF THE INVENTION

The present invention provides novel compounds, novel compositions, methods of their use and methods of their manufacture, such compounds being generally pharmacologically useful as anti-platelet aggregation agents in various vascular pathologies.

The aforementioned pharmacologic activities are useful in the treatment of mammals. More specifically, the compounds of the present invention act by blocking the platelet receptor site of the protein fibrinogen. Fibrinogen is a glycoprotein that circulates in the blood plasma, and whose platelet receptor site is glycoprotein IIb/IIIa. By blocking the action of fibrinogen at the receptor (glycoprotein IIb/IIIa), the compounds of the present invention interfere with platelet aggregation, which is a cause of many vascular pathologies. At the present time, there is a need in the area of vascular therapeutics for such a fibrinogen receptor blocking agent. By interfering with hemostasis, such therapy would decrease the morbidity and mortality of thrombotic disease.

Hemostasis is the spontaneous process of stopping bleeding from damaged blood vessels. Precapillary vessels contract immediately when cut. Within seconds, thrombocytes, or blood platelets, are bound to the exposed matrix of the injured vessel by a process called platelet adhesion. Platelets also stick to each other in a phenomenon known as platelet aggregation to form a platelet plug. This platelet plug can stop bleeding quickly, but it must be reinforced by the protein fibrin for long-term effectiveness, until the blood vessel tear can be permanently repaired by growth of fibroblasts, which are specialized tissue repair cells.

An intravascular thrombus (clot) results from a pathological disturbance of hemostasis. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These diseases include venous thrombosis, thrombophlebitis, arterial embolism, coronary and cerebral arterial thrombosis, myocardial infarction, stroke, cerebral embolism, kidney embolisms and pulmonary embolisms.

There is a need in the area of cardiovascular and cerebrovascular therapeutics for an agent which can be used in the prevention and treatment of thrombi, with minimal side effects, including unwanted prolongation of bleeding in other parts of the circulation while preventing or treating target thrombi. The compounds of the present invention meet this need in the art by providing therapeutic agents for the prevention and treatment of thrombi.

The compounds of the present invention show efficacy as antithrombotic agents by virtue of their ability to block fibrinogen from acting at its platelet receptor site, and thus prevent platelet aggregation.

SUMMARY OF THE INVENTION

The present invention relates to novel compounds having the general structural formula I:

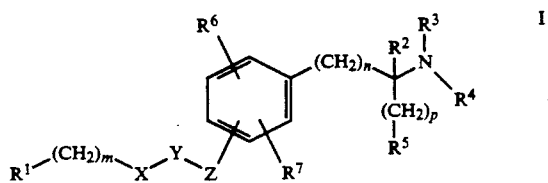

and the pharmaceutically acceptable salts thereof, wherein $R^1$ is a four to eight member heterocyclic ring containing 1, 2, 3 or 4 hetero atoms wherein said heteroatoms are N, O or S and wherein said heterocyclic ring is optionally substituted at any atom by H, $R^6$ or $R^7$;

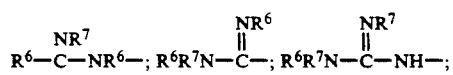

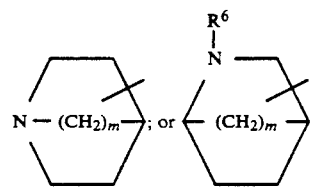

$NR^6R^7$ wherein $R^6$ and $R^7$ are independently hydrogen, $C_{1-10}$ alkoxycarbonyl or unsubstituted or substituted $C_{1-10}$ alkyl and cycloalkyl wherein said substituents are $C_{1-10}$ alkoxy,
$C_{1-10}$ alkoxyalkyl,
$C_{1-10}$ alkoxyalkyloxy,
$C_{1-10}$ alkoxycarbonyl,
$C_{1-10}$ alkylcarbonyl,
$C_{0-6}$ alkylaminocarbonyl,
$C_{1-10}$ aralkylcarbonyl,
$C_{1-10}$ alkylthiocarbonyl,
$C_{4-10}$ aralkylthiocarbonyl,
thiocarbonyl,
$C_{1-10}$ alkoxythiocarbonyl,
aryl,
5 to 6 membered saturated heterocyclic rings of 1, 2, 3 or 4 hetero atoms wherein said hetero atoms are taken from the group consisting of N, O and S,
$C_{1-4}$ alkanoylamino,
$C_{1-6}$ alkoxycarbonyl-$C_{0-6}$ alkylamino,
$C_{1-10}$ alkylsulfonylamino,
$C_{4-10}$ aralkylsulfonylamino,
$C_{4-10}$ aralkyl,
$C_{1-10}$ alkaryl,
$C_{1-10}$ alkylthio,
$C_{4-10}$ aralkylthio,
$C_{1-10}$ alkylsulfinyl,
$C_{4-10}$ aralkylsulfinyl,
$C_{1-10}$ alkylsulfonyl,
$C_{4-10}$ aralkylsulfonyl,
aminosulfonyl, $C_{1-10}$ alkylaminosulfonyl,
$C_{4-10}$ aralkylsulfonylamino,
oxo,
thio,
unsubstituted or mono- or di-substituted 1-ethenyl, 2-ethenyl or 3-propenyl wherein said substituents are selected from the group consisting of hydrogen, $C_{1-10}$ alkyl and $C_{7-10}$ aralkyl,
carboxy,
hydroxy,
amino,
$C_{1-6}$ alkylamino,
$C_{1-6}$ dialkylamino,
halogen, where halogen is defined as Cl, F, Br, or I,
nitro, or
cyano,
and further wherein said N can additionally be substituted to form a quaternary ammonium ion wherein said substituent is as previously defined for $R^6$ and $R^7$;
$R^2$ and $R^3$ are independently hydrogen, aryl or unsubstituted or substituted $C_{0-10}$ alkyl or cycloalkyl wherein said substituent is
$C_{1-10}$ alkoxyalkyl,
aryl,
a 4 to 8 membered heterocyclic ring containing 1, 2, 3 or 4 hetero atoms, wherein said heteroatoms are taken from the group consisting of N, O and S,
$C_{4-10}$ aralkyl,
$C_{1-10}$ alkaryl,
carboxy,
$C_{1-10}$ alkylcarbonyl,
$C_{1-10}$ alkylthiocarbonyl,
$C_{4-10}$ aralkylcarbonyl,
$C_{4-10}$ aralkylthiocarbonyl,
$C_{1-6}$ alkoxycarbonyl,
$C_{4-10}$ aralkoxycarbonyl,
$C_{1-6}$ alkoxy,
$C_{4-10}$ aralkoxy,
$C_{1-6}$ alkylamino,
$C_{1-12}$ dialkylamino,
$C_{1-6}$ alkanoylamino,
$C_{4-12}$ aralkanoylamino,
$C_{4-10}$ aralkylamino;
$R^4$ is
hydrogen,
aryl,
$C_{1-10}$ alkyl or cycloalkyl
$C_{4-10}$ aralkyl,
arylcarbonyl, aminocarbonyl,
$C_{1-10}$ alkylcarbonyl, $C_{1-6}$alkylaminocarbonyl,
$C_{1-10}$ alkylthiocarbonyl, $C_{0-6}$dialkylaminocarbonyl,
$C_{1-10}$ alkoxythiocarbonyl, aryl$C_{0-6}$alkylaminocarbonyl,
$C_{1-10}$ alkoxycarbonyl,
$C_{4-10}$ aralkylcarbonyl,
$C_{4-10}$ aralkoxycarbonyl,
$C_{1-10}$ carboxyalkyl and
further wherein any of the substitutents for $R^4$ may be substituted by one or more substituents selected from the group as defined for $R^6$, or an L- or D-amino acid joined by an amide linkage;
$R^5$ is
a four to eight membered saturated or unsaturated heterocyclic ring containing 1, 2, 3 or 4 hetero atoms wherein said hetero atoms are N, O, or S or,

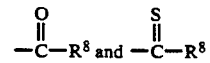

wherein $R^8$ is hydroxy,
$C_{1-10}$ alkyloxy,
$C_{1-10}$ alkaryloxy,
$C_{4-10}$ aralkyloxy,
$C_{4-10}$ aralkylcarbonyloxy,
$C_{1-10}$ alkoxyalkyloxy,
$C_{1-10}$ alkoxyalkylcarbonyloxy,
$C_{1-10}$ alkoxycarbonyloxyalkyl,
$C_{1-10}$ alkylcarbonyloxyalkyloxy,
an L- or D-amino acid joined by an amide linkage, and wherein the carboxylic acid moiety of said amino acid is as the free acid or is esterified by $C_{1-6}$ alkyl.

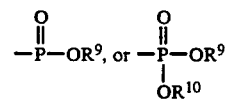

wherein $R^9$ and $R^{10}$ are selected from the group consisting of hydrogen, $C_{1-10}$ alkyl and $C_{4-10}$ aralkyl;
X and Y are independently
$NR^6$,
O,
S,
SO,
$SO_2$, $$-\underset{\underset{R^6}{|}}{C}=\underset{\overset{R^7}{\diagup}}{C}-,$$

—C≡C—,
oxo,
aryl,
thiono,
unsubstituted or substituted $C_{1-15}$ alkyl or cycloalkyl wherein said substituents are independently $R^6$ and $R^7$, $$\underset{NR^{6'}}{\overset{O}{\underset{\|}{\diagdown C \diagup}}},$$

$$\underset{NR^{6'}}{\diagup}\overset{O}{\underset{\|}{\diagdown C}}\diagdown,$$

$-NR^6-SO_2-$, $-SO_2-NR^6-$, or
a 4- to 8- membered heterocyclic ring containing 1, 2, 3, or 4 heteroatoms wherein said atoms are N, O, or S and wherein said ring is independently substituted at any atom with $R^6$;
Z is an optional substituent that, when present, is independently chosen as defined by X and Y;
m is an integer of from zero to ten;
n is an integer of from zero to ten; and
p is an integer of from zero to three.
A preferred group of compounds of the present invention are those defined for general structural formula II as:

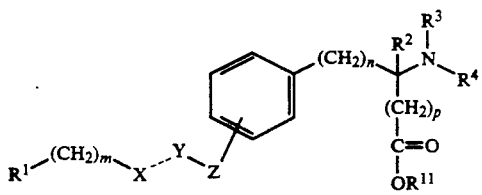

wherein
R¹ is a five to six membered heterocyclic ring wherein said heteroatoms are N, O, or S, and wherein said heterocyclic ring is optionally substituted by hydrogen, $C_{1-5}$ alkyl; or $NR^6R^7$ wherein $R^6$ and $R^7$ are independently hydrogen, unsubstituted or substituted $C_{1-10}$ alkyl or $C_{4-10}$ aralkyl wherein said substituents are chosen from
$C_{1-10}$ alkoxycarbonyl,
aryl,
$C_{0-5}$ dialkylamino $C_{1-10}$ alkyl, and
$C_{4-10}$ aralkyl,
and further wherein said N can additionally be substituted to form a quaternary ammonium ion;
$R^2$ and $R^3$ are hydrogen, $C_{1-4}$ alkyl or $C_{4-10}$ aralkyl;
$R^4$ is
H,
$C_{1-10}$ alkyl,
$C_{4-10}$ aralkyl,
arylcarbonyl,
$C_{1-10}$ alkylcarbonyl,
$C_{1-10}$ alkoxycarbonyl,
$C_{4-10}$ aralkylcarbonyl, or
$C_{4-10}$ aralkoxycarbonyl, wherein $R^4$ is unsubstituted or substituted with $R^6$ as previously defined;
$R^{11}$ is
hydrogen or
$C_{1-10}$ alkyl;
X and Y are independently O, S, SO, $SO_2$,

aryl, —CH=CH—,

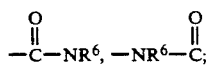

—$SO_2NR^6$; —$NR^6SO_2$—, or a 5- or 6- membered heterocyclic ring containing 1 or 2 heteroatoms, wherein said atoms are N, O or S, unsubstituted or substituted $C_{1-15}$ straight, branched, or cyclic alkyl wherein said substituent is oxo, hydroxy $C_{1-4}$ alkyloxy, or $C_{4-10}$ arylalkyl;
Z is an optional substituent that, when present, is O, $SO_2$, —$NR^6CO$—, —$CONR^6$—,

or $C_{1-10}$ straight or branched alkyl;
m is an integer of from zero to eight;
n is an integer of from zero to two; and
p is an integer of from zero to two.
A more preferred group of compounds of the present invention are those defined for the general structural formula III as

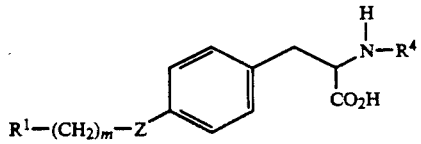

wherein
R¹ is a five or 6-membered heterocyclic ring wherein said heteroatom is N and wherein said heterocyclic ring is optionally substituted by hydrogen or $C_{1-5}$ alkyl, or $NR^6R^7$ wherein $R^6$ and $R^7$ are independently hydrogen, $C_{1-10}$ alkyl or $C_{4-10}$ arylalkyl;
$R^4$ is
arylcarbonyl,
$C_{1-10}$ alkylcarbonyl,
$C_{1-10}$ alkoxycarbonyl,
$C_{4-10}$ aralkylcarbonyl,
$C_{4-10}$ aralkoxycarbonyl wherein $R^4$ is unsubstituted or substituted with $R^6$ as previously defined;
Z is chosen from: O, —$NR^6CO$—, —$CONR^6$—, or $CH_2$; and
m is an integer of from one to six
Preferred compounds of the invention are:
2-S-(N-Benzyloxycarbonylamino)-3-[4-(N,N,2,2-tetramethyl-1,3-propanediamino)propyloxyphenyl]propionic acid;
2-S-(N-Benzyloxycarbonylamino)-3-[4-(3-N-pyrolidinylpropyloxy)phenyl]propionic acid;
2-S-(N-Benzyloxycarbonylamino)-[4-(3-N-methyl-N-benzylaminopropyloxyphenyl)propionic acid;
2-S-(N-Benzyloxycarbonylamino)-3-[4-(4-piperazinyl)-butyloxyphenyl]propionic acid;
2-S-(N-Benzyloxycarbonylamino)-3-[4-(1,1,3,3-tetramethylbutylamino)propyloxyphenyl]propionic acid;
2-S-(N-Benzyloxycarbonyl)-3-[4-(4-methylpiperazin-1-yl)propyloxyphenyl]propanoic acid;
2-S-(N-Benzyloxycarbonylamino)-3[4-(4-piperazin-1-yl)pentyloxyphenyl]propionic acid;
2-S-(N-Benzyloxycarbonylamino)-3-[4-(6-aminohexyloxyphenyl)]propionic acid hydrochloride;
2-S-(N-Benzyloxycarbonylamino)-3-[4-(7-aminoheptyloxy) phenyl]propionic acid hydrochloride;
2-S-(N-Benzyloxycarbonylamino)-3-[4-(8-aminooctyloxy)phenyl]propionic acid;
2-S-(N-Benzyloxycarbonylamino)-3-[4-(5-aminopentyloxy)phenyl]propionic acid hydrochloride;
2-S-(N-Benzyloxycarbonylamino)-3-[4-(4-piperidinylbutyloxy)phenyl]propionic acid;
2-S-Phenylcarbonylamino-3-[4-(6-aminohexyloxy)-phenyl]propionic acid hydrochloride;
2-S-(Phenethylcarbonylamino)-3-[4-(6-aminohexyloxy)phenyl]propanoic acid hydrochloride;
2-S-(Phenylacetylamino)-3-[4-(6-aminohexyloxy)-phenyl]propionic acid;
2-S-(2-Carboxy-3-phenylpropionylamino)-3-[4-(6-aminohexyloxy)phenyl]propionic acid;
2-S-(Hexanoylamino)-3-[4-(6-aminohexyloxy)phenyl]-propionic acid Hydrochloride;
2-S-(2-Naphthanoylamino)-3-[4-(6-aminohexyloxy)-phenyl]propionic acid;
2-S-(Butanoylamino)-3-[4-(6-aminohexyloxy)phenyl]-propionic acid;
2-S-(Heptanoylamino)-3-[4-(6-aminohexyloxy)phenyl]-propionic acid hydrochloride;
2-S-(5-Phenylpentanoylamino)-3-[4-(6-aminohexyloxy)-phenyl]propionic acid hydrochloride;

2-S-(3-Carboxypropanoyl)amino-3-[4-(6-aminohexyloxy)phenyl]propionic acid hydrochloride;
2-S-(Acetylamino)-3-[4-(6-aminohexyloxy)phenyl]propionic acid hydrochloride;
2-S-(N-Benzyloxycarbonylamino)-3-[4-(4-piperidinyl)-but-2-enyloxyphenyl]propionic acid;
2-S-(N-t-Butyloxycarbonylamino)-3-[4-(4-t-butylaminobutyl)phenyl]propionic acid;
2-S-(Pentanoylamino)-3-[4-(4-piperidin-ylbutyloxy)-phenyl]propionic acid hydrochloride;
2-S-(Hexanoylamino)-3-[4-(4-piperidin-ylbutyloxy)-phenyl]propionic acid;
2-S-(5-Aminopentanoyl)amino-3-[4-(6-aminohexyloxy)-phenyl)]propionic acid dihydrochloride;
2-S-(4-Carboxybutanoylamino)-3-[4-(6-aminohexyloxy)phenyl]propionic acid;
Methyl 2-S-(N-Benzyloxycarbonylamino)-3-[4-(2,6-dimethylpiperazin-4-yl)butyloxyphenyl]propionate;
2-(N-Benzyloxycarbonylamino)-3-[4-(2,6-dimethylpiperazin-4-yl)butyloxyphenyl]propionic acid;
3-S-(N-Benzyloxycarbonylamino)-4-[4-piperidin-4-yl)propyloxyphenyl]butanoic acid; and
2-S-(Hexanoylamino)-3-[4-(5-piperidin-4-yl)pentyl-phenyl]propionic acid.

DETAILED DESCRIPTION OF THE INVENTION

The term "pharmaceutically acceptable salts" shall mean non-toxic salts of the compounds of this invention which are generally prepared by reacting the free base with a suitable organic or inorganic acid. Representative salts include the following salts:
Acetate
Benzenesulfonate
Benzoate
Bicarbonate
Bisulfate
Bitartrate
Borate
Bromide
Calcium Edetate
Camsylate
Carbonate
Chloride
Clavulanate
Citrate
Dihydrochloride
Edetate
Edisylate
Estolate
Esylate
Fumarate
Gluceptate
Gluconate
Glutamate
Glycollylarsanilate
Hexylresorcinate
Hydrabamine
Hydrobromide
Hydrochloride
Hydroxynaphthoate
Iodide
Isothionate
Lactate
Lactobionate
Laurate
Malate
Maleate
Mandelate
Mesylate
Methylbromide
Methylnitrate
Methylsulfate
Mucate
Napsylate
Nitrate
Oleate
Oxalate
Pamaote
Palmitate
Pantothenate
Phosphate/diphosphate
Polygalacturonate
Salicylate
Stearate
Subacetate
Succinate
Tannate
Tartrate
Teoclate
Tosylate
Triethiodide
Valerate The term "pharmacologically effective amount" shall mean that amount of a drug or pharmaceutical agent that will elicit the biological or medical reponse of a tissue, system or animal that is being sought by a researcher or clinician. The term "anti-coagulant" shall include heparin, and warfarin. The term "thrombolytic agent" shall include streptokinase and tissue plasminogen activator. The term "platelet anti-aggregation agent" shall include aspirin and dipyridimole.

The term "aryl" shall mean a mono- or polycyclic system composed of 5- and 6- membered aromatic rings containing 0, 1, 2, 3 or 4 heteroatoms chosen from N, O or S and either unsubstituted or substituted with $R^6$.

The term "alkyl" shall mean straight or branched chain alkane, alkene or alkyne.

The term "alkoxy" shall be taken to include an alkyl portion where alkyl is as defined above.

The terms "aralkyl" and "alkaryl" shall be taken to include an alkyl portion where alkyl is as defined above and to include an aryl portion where aryl is as defined above.

The term "halogen" shall include fluorine, chlorine, iodine and bromine.

The term "oxo" shall mean the radical =O.
The term "thio" shall mean the radical =S.
In the schemes and examples below, various reagent symbols have the following meanings:
BOC: t-butyloxycarbonyl.
Pd-C: Palladium on activated carbon catalyst.
DMF: Dimethylformamide.
DMSO: Dimethylsulfoxide.
CBZ: Carbobenzyloxy
$CH_2Cl_2$: methylene chloride
$CHCl_3$: chloroform
EtOH: ethanol
MeOH: Methanol
EtOAc: ethylacetate
HOAc: acetic acid
BOP: Benzotriazol-1-yloxytris(dimethylamino)phosphonium, hexafluororophosphate The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, subcutaneous or intramuscular form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol., 1987, 252:H, pp 615–621). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter of arrest the progress of the condition.

Oral dosages of the present invention, when used for the indicated effects, will range between about 0.01 mg per kg of body weight per day (mg/kg/day) to about 100 mg/kg/day and preferably 1.0–100 mg/kg/day and most preferably 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesuim stearate, dicalcium phosphate, calcium sulfate, mannitol, sorbitol and the like; for oral administration in liquid form, the oral drug components can be combined with any oral, non-toxic, pharmacetically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesilces and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds of the present invention can also be co-administered with suitable anti-coagulant agents or thrombolytic agents such as plasminogen activators or streptokinase to achieve synergistic effects in the treatment of various vascular pathologies. They may also be combined with heparin, aspirin or warfarin.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

Generally, compounds of the invention are prepared as follows:

Scheme I

An N-protected tyrosine analog is O-alkalated by deprotonation with an alkali hydride followed by treatment with an appropriate alkylating agent. Typically, the N-protecting groups are BOC or CBZ and the hydride reagent is NaH, KH or the like. The alkylating agent may be a dihalide, which reacts at only one site under the present conditions, or may, for example, be an amino-group containing halide, wherein the amine has suitable BOC, CBZ, FMOC, etc. protection. This reaction is typically carried out in DMF or an ethereal solvent such as THF at 0°–50° for from 0.5 to 12 hrs. In the case of a dihalide alkylating agent, bromides, chlorides or iodides may be used, and subsequent treatment with an amine reagent will provide a further intermediate. This reaction typically would be run in acetonitrile or an ether, such as THF or $Et_2O$, at 0°–60° for 1–24 hrs and would employ a variety of primary and secondary amines.

Deprotection of the tyrosine amino group would then typically be carried out by catalytic hydrogenation (to remove CBZ) or acid treatment (to remove BOC). This free amino acid may then be functionalized, e.g. acylated or alkylated on the α-amino N by treatment under basic conditions with an appropriate acid chloride, acid anhydride, alkyl halide or other similarly reactive reagent. Final deprotection may then be effected with treatment by acid or base.

Alternatively the N-protected amino acid described above may be esterified, for example by treatment of its cesium salt with an alkyl halide such as an alkyl iodide. Removal of the N-protecting group via catalytic hydrogen (for N-CBZ analogs) or HCl or $CF_3CO_2H$ (for N-Boc analogs) provides the L-amino ester which may be acylated or alkylated. Typically, this reaction involves treatment of the amino ester with alkyl or aryl acid chlorides, anhydrides or alkylating agents in halocarbon solvents, such as $CH_2Cl_2$, ethers, such as THF, or similar solvents in the presence of a base such as N-methylmorpholine or $NaHCO_3$. Typically, these reactions are run at 0°–80° C. for from 1–24 hours.

Scheme 4

Iodo-substituted N-protected tyrosines are alkynylated with an alkyne under catalytic Pd $[PPh_3]_2Cl_2$ conditions with an alkanol such as butyn-4-ol. Typically, this reaction is run in an amine solvent, such as $Et_2NH$ and may employ alkyl and arylalkyl alcohols. The resulting alkyne may be catalytically reduced and then functionalized by conversion to a reactive halide, tosylate or the like. Displacement with a primary or secondary amine, or similar nucleophile will then provide an advanced intermediate. Deprotection of the appended amine and carboxylic acid groups may then be carried out under basic or acidic conditions.

Scheme 6

A variety of amino terminal groups may be introduced by alkylation of tyrosine-O with dihalides, such as 1-bromo-3-chloropropane or similar iodochlorides, or chlorotosylates. Typically, the phenol is treated with $Cs_2CO_3$ or similar reagent followed by the alkylating agent. Displacement at the second alkylating site with piperidine, piperazine or similar nucleophilic reagents affords structurally diverse intermediates. Typically, the displacement reaction involves heating the reactants neat or in a solvent, such as THF or $CH_3CN$ at 30°–90° for from 1–10 hours. The resultant intermediates are then suitably deprotected to provide the final products.

Scheme 8

Modified C-terminal analogs may be prepared by palladium-mediated coupling of a halogenated phenyl alanine ester, such as 8-2 with an alkyne, such as 8-4 to provide the advanced intermediate 8-6. For this coupling, the phenyl alanine component may be a carboxylic ester, such as methyl or ethyl, and the α-amine group may be a free amine or it may be acylated or sulfonylated. The acetylenic component may contain alkyl or aryl substituents and may be substituted with suitably protected amino groups. Typically, the coupling reaction is run in $Et_2NH$ at 0°–35° C. for from 1–18 hours.

The resultant coupling products may be subsequently modified by, for example, reduction with $H_2$ over Pd catalyst. Final deprotection with base and subsequently with acid to remove amino and carboxy protection groups affords final products.

SCHEME 1

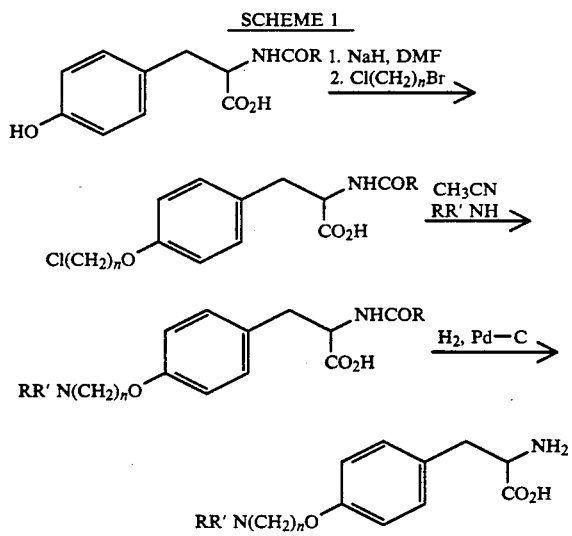

EXAMPLE 1

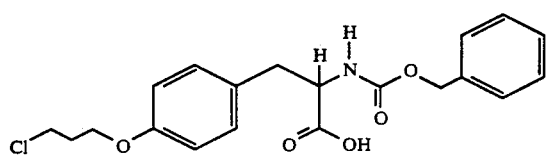

2-S-(N-Benzyloxycarbonylamino)-3-[4-(3-chloropropyloxy)phenyl]propionic acid (1-1)

N-CBZ-tyrosine (3 g, 9.9 mmole) (from Bachem Chemical Supply, California), was dissolved in DMF and treated with NaH (50% dispersion in oil, 0.95 g, 19.8 mmole) for 1 hour, then 1,3 bromochloropropane (1 ml, 9.9 mmole) was added and the reaction stirred for 16 hours. The DMF was removed in vacuo and the residue dissolved in water, acidified to pH 3, and extracted with ethyl acetate. The ethyl acetate layer was dried with MgSO4, filtered and evaporated. Column chromatography (SiO2, 97:3:1 CHCl3/CH3OH/HOAc) yielded 2.42 g of product as a yellow oil.

RF=0.3 in 97:3:1 CHCl3/CH3OH/HOAc ninhydrin stain

300 MHz $^1$H NMR (CDCl3) δ 7.3 (bs, 5H), 7.03 (d, J=8.3, 2H), 6.8 (d, J=8.3, 2H), 5.2 (d, J=8Hz, 1H), 5.05 (bs, 2H) 4.65 (m, 1H), 4.05 (t, J=5.7 Hz, 2H), 3.73 (t, J=6.3 Hz, 2H), 3.1 (m, 2H), 2.2 (m, 2H).

EXAMPLE 2

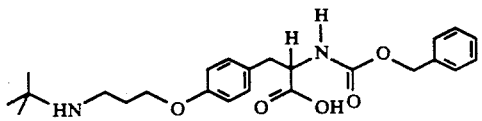

2-S-(N-Benzyloxycarbonylamino)-[4-(3-t-butylaminopropyloxy)phenyl]propionic acid (1-2)

Compound 1-1 (0.4 g, 1.1 mmole) was refluxed in t-butylamine (20 ml) and acetonitrile (20 mL) for three days. The reaction was evaporated to dryness, the residue dissolved in water, and extracted with ether. The aqueous layer was then acidified to pH 4-5 and a precipitate formed. The solid was collected and dried to yield 70 mg of product.

Rf=0.8 in 9:1 EtOH/NH4OH, ninhydrin stain.

300 MHz $^1$H NMR (D2O+NaOH) δ 7.4 (bs, 2H), 7.2 (bs, 4H), 6.85 (d, J=8.55, 2H), 5.2 (d, J=12.8 Hz, 1H), 5.0 (d, J=12.8 Hz, 1H), 4.3 (dd, J=4.0, 9.6 Hz, 1H), 4.0 (bs, 2H), 3.2(dd, J=4.0, 13.6 Hz, 1H), 2.8 (dd, J=9.6 Hz, 13.6 Hz, 1H), 2.65 (t, J=7.3 Hz, 2H), 1.8 (m, 2H), 1.09 (s, 9H), mass spec (FAB) m/e=429 (m+1)

C, H, N analysis C24H32N2O5 0.65 H2O: MW=440.244 Calculated C=65.47, H=7.62, N=6.36; Found C=65.52, H=7.54, N=6.27.

EXAMPLE 3

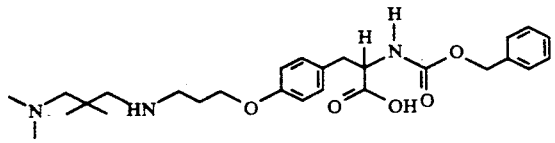

2-S-(N-Benzyloxycarbonylamino)-3-[4-(N,N,2,2-tetramethylpropanediamino)propyloxyphenyl]propionic acid (1-3)

Treatment of compound 1-1 with excess N,N,2,2-tetramethyl-1,3-propenediamine by refluxing in acetonitrile for three days, and followed by an aqueous workup provided crude 1-3. This was chromatographed on silica gel eluting with 9:1:1 EtOH/H2O/NH4OH to provide pure 1-3 (R$_f$=0.37 ninhydrin stain). 300 MHz $^1$H NMR (D2O) δ 7.5 (bs, 3H), 7.4 (bs, 2H), 7.33 (d, J=8.3 Hz, 2H), 7.0 (d, J=8.3 Hz, 2H), 5.20 (d, J=10 Hz, 1H), 5.10 (d, J=10 Hz, 1H), 4.25 (m, 1H), 4.25 (t, J=5.6 Hz, 2H), 3.4 (t, J=7.8 Hz 2H), 3.4 (s, 2H), 3.25-2.95 (m, 2H), 3.22 (s, 2H), 3.1 (s, 6H), 2.35 (m, 2H), 1.38 (s, 6H).

MW=759.28

C, H, N analysis for C27H39N2O5.2.4 C2HF3O2. Calcd: C, 50.30; H, 5.50; N, 5.53; Found: C, 50.35; H, 5.43; N, 5.56.

EXAMPLE 4

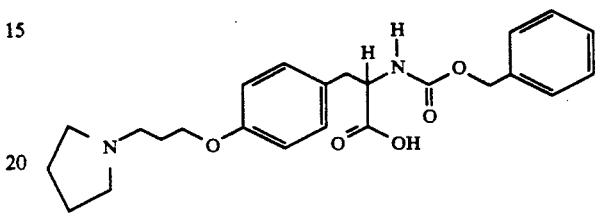

2-S-(N-Benzyloxycarbonylamino)-3-[4-(3-N-pyrrolidinylpropyloxy)phenyl]propionic acid (1-4)

Treatment of compound 1-1 with excess pyrrolidine in CH3CN at reflux for three days provided crude 1-4. This was purified by flash chromatography on silica gel eluting with 9:1:1 EtOH/H2O/NH4OH to give pure 1-4 (R$_f$=0.81, ninhydrin stain) in 36% yield. 300 MHz $^1$H NMR (CDCl3) δ 7.3 (bs, 5H), 7.0 (d, J=8.1 Hz, 2H), 6.7 (d, J=8.1 Hz, 2H), 5.5 (d, J=7.4 Hz, 1H), 5.0 (bs, 2H), 4.5 (m, 1H), 3.8 (m, 2H), 3.75 (bs, 1H), 3.4 (m, 2H), 3.18 (t, J=8.5 Hz, 2H), 3.1 (bs, 2H), 2.8 (bs, 1H), 2.2-1.8 (m, 6H).

C, H, N analysis C24H30N2O5.0.25 CH2Cl2: Calcd: C, 65.05; H, 6.87; N, 6.26; Found: C, 65.28; H, 6.78; N, 6.27.

EXAMPLE 5

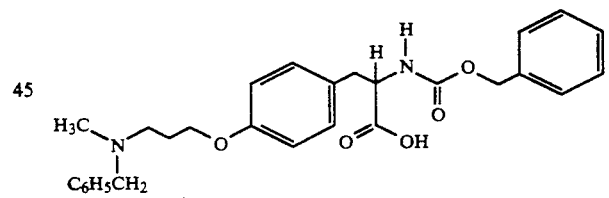

2-S-(N-Benzyloxycarbonylamino)-[4-(3-N-methyl-N-benzylaminopropyloxyphenyl)]propionic acid (1-5)

Treatment of 1-1 with excess N-methyl benzylamine in acetonitrile at reflux for three days afforded crude 1-5. The solvent was removed on a rotary evaporator and the residue was dissolved in water and extracted with 3×75 mL portions of ether. The product separated out as an oil which was collected and concentrated to give 1-5 (70 mg) as a foam. 300 MHz $^1$H NMR (CDCl3/CD3OD) δ 7.4 (m, 10H), 7.0 (d, J=8.5 Hz, 2H), 6.6 (d, J=8.5 Hz, 2H), 5.0 (bs, 2H), 4.5 (m, 1H), 4.2 (bs, 2H), 3.88 (t, J= 5.3 Hz, 2H), 3.1-2.8 (m, 4H), 2.69 (s, 3H), 2.2 (bs, 2H).

C, H, N analysis C28H32N2O5.0.8 CH2Cl2.0.25 EtOAc: Calcd: C, 63.17; H, 6.33; N, 4.94; Found: C, 63.16; H, 6.40; N, 5.04.

MW=548.771

EXAMPLE 6

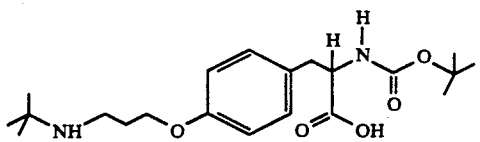

2-S-(N-t-Butyloxycarbonylamino)-[4-(3-N-t-butylaminopropyloxy)phenyl]propionic acid (1-6)

Treatment of N-BOC-L-tyrosine with sodium hydride in DMF followed by 1,3-bromochloropropane provided the N-BOC analog 1-1. This was treated with an excess of t-butylamine in refluxing acetonitrile for two days to provide crude 1-6 after aqueous workup and extraction. Pure 1-6 was prepared by preparative reverse phase HPLC.

300 MHz $^1$H NMR (CD$_3$OD) δ 7.17 (d, J=8.5 Hz, 2H), 6.85 (d, J=8.5 Hz, 2H), 4.28 (dd, J=4.8, 9.1 Hz, 1H), 4.1 (t, J=5.9 Hz, 2H), 3.2 (t, J=7.7 Hz, 2H), 3.1 (dd, J=4.8, 13.3 Hz, 1H), 2.8 (dd, J=9.1, 13.3 Hz, 1H), 2.15 (m, 2H), 1.38 (s, 18H).

C, H, N analysis C$_{21}$H$_{34}$N$_2$O$_7$.1.05 C$_2$HF$_3$O$_2$: MW=514.243; Calcd: C, 53.95; H, 6.87; N, 5.45; Found: C, 54.01; H, 6.97; N, 5.51.

EXAMPLE 7

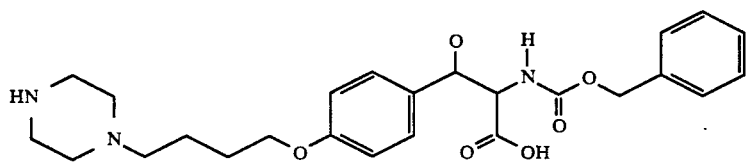

2-S-(N-Benzyloxycarbonylamino)-3-[4-(4-piperazinyl)-butyloxyphenyl]propionic acid (1-7)

Treatment of N-CBZ-L-tyrosine with sodium hydride in DMF followed by 1,4-dibromobutane, as described for the preparation of 1-1, provided the corresponding butyl analog. Treatment of this with 1,4-piperazine in refluxing acetonitrile for three days gave crude 1-7 as a precipitate from the reaction mixture. Reverse phase HPLC purification gave pure 1-7.

300 MHz $^1$H NMR (CD$_3$OD) δ 7.3 (m, 5H), 7.23 (d, 2H), 6.83 (d, 2H), 5.0 (bs, 2H), 4.35 (dd, 1H), 4.0 (t, 2H), 3.6 (bs, 8H), 3.1 (dd, 1H), 2.85 (dd, 1H), 2.00-1.8 (m, 4H).

C, H, N analysis C$_{26}$H$_{35}$N$_3$O$_5$.1.2 H$_2$O; MW=491.206; Calcd: C, 63.57; H, 7.67; N, 8.56; Found: C, 63.33; H, 7.28; N, 8.55.

EXAMPLE 7(a)

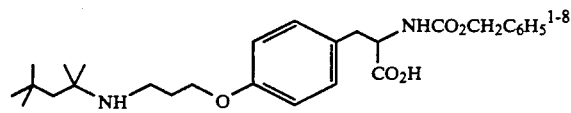

2-S-(N-Benzyloxycarbonylamino)-3-[4-(1,1,3,3-tetramethylbutylamino)propyloxyphenyl]propionic acid (1-8)

Treatment of 1-1 with 1,1,3,3-tetramethylbutylamine, as described for compound 1-2, gave 1-8 as the TFA salt. $^1$H NMR (300 MHz CD$_3$OD) δ 7.35 (5H, m), 7.18 (2H, d), 6.85 (1H, d), 5.00 (2H, s), 4.35 (1H, dd), 4.10 (2H, t), 3.1 (2H, t), 3.15 (1H, dd), 2.50 (1H, dd), 2.1 (2H, m), 1.70 (2H, s), 1.5 (6H, s), 1.10 (9H, s).

Analysis for C$_{28}$H$_{40}$N$_2$O$_5$.0.9 C$_2$HF$_3$O$_2$; Calcd: C, 60.94; H, 7.02; N, 4.77; Found: C, 60.85; H, 7.01; N, 4.69.

EXAMPLE 7(b)

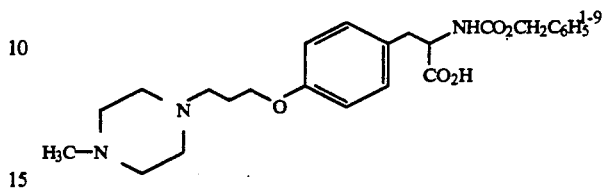

2-S-(N-Benzyloxycarbonyl)-3-[4-(4-methylpiperazin-1-yl)propyloxyphenyl]propanoic acid (1-9)

Treatment of 1-1 with N-methylpiperazine as described for 1-2 gave crude 1-9. This was purified by column chromatography on silica gel eluting with 9:1:1 C$_2$H$_5$OH/H$_2$O/NH$_4$OH to give pure 1-9 as the TFA salt.

$^1$H NMR (300 MHz D$_2$O) δ 7.5 (3H, m), 7.4 (2H, d), 7.0 (2H, d), 5.18 (1H, d), 5.05 (1H, d), 4.5 (1H, m), 4.2 (2H, t), 3.8 (8H, s), 3.6 (2H, t), 3.3 (1H, m), 3.1 (3H, s), 3.0 (1H, m), 2.4 (2H, m).

Analysis for C$_{25}$H$_{33}$N$_3$O$_5$.2.3 C$_2$HF$_3$O$_2$; Calcd: C, 49.52; H, 4.96; N, 5.85; Found: C, 49.42; H, 4.98; N, 6.01.

EXAMPLE 7(c)

2-(N-Benzyloxycarbonylamino)-3-[4-(5-bromopentyloxy)phenyl]propionic acid (1-10)

N-CBZ-L-tyrosine (2.06 g, 5.86 mmole) was treated with NaH (0.58 g, 12.08 mmole) and 1,5-dibromopentane (0.8 ml, 5.87 mmole) as described for 1-1 in Example 1. The crude product was dissolved in methanol and after stirring with silica gel for 0.5 hour; the solvent was removed. This was dry packed and eluted on a flash column with CHCl$_3$ and then with 97:3:0.3 CHCl$_3$/CH$_3$OH/HOAc to give pure 1-10 (0.66 g).

$^1$H NMR (300 MHz, CD$_3$OD) δ 1.50-1.65 (2H, m), 1.63-1.95 (4H, m), 3.10 (2H, m), 3.45 (1H, t), 3.92 (2H, m), 4.40 (1H, m), 6.80 (2H, d), 7.10 (2H, d), 7.28 (5H, m).

EXAMPLE 7(d)

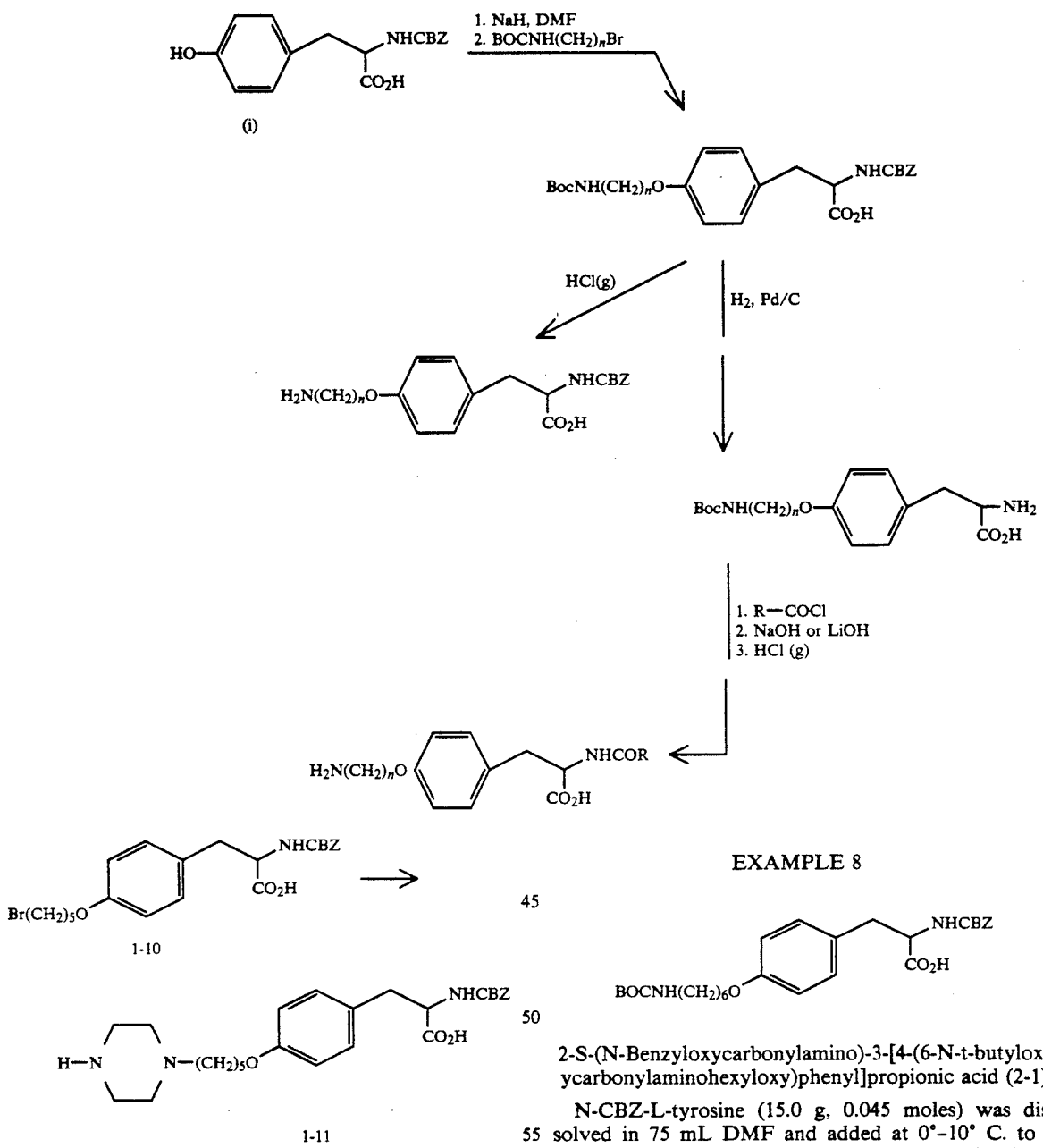

2-S-(N-Benzyloxycarbonylamino)-3-[4-(4-piperazin-1-yl)pentyloxyphenyl]propionic acid (1-11)

1-10 (0.658 g, 1.42 mmole), was dissolved in 30 mL CH$_3$CN and 1,4-piperazine (1.22 g, 14.16 mmoles) was added. This solution was stirred at room temperature for 4 days. The solvent was then removed and the residue was dry packed on a silica gel column and eluted with 18:1:1 C$_2$H$_5$OH/H$_2$O/NH$_4$OH to give pure 1-11 (34 mg) as a white solid.

$^1$H NMR (300 MHz, CD$_3$OD) δ 1.52 (4H, m), 1.77 (2H, m), 2.40 (2H, t), 2.59 (4H, m), 2.80–2.94 (1H, m), 3.01–3.12 (5H, m), 3.94 (2H, m), 4.21 (1H, m), 6.76 (2H, d), 7.09 (2H, d).

Analysis for C$_{26}$H$_{35}$N$_3$O$_5$·1.2 H$_2$O; Calcd: C, 63.57; H, 7.67; N, 8.56; Found: C, 63.33; H, 7.28; N, 8.55.

EXAMPLE 8

2-S-(N-Benzyloxycarbonylamino)-3-[4-(6-N-t-butyloxycarbonylaminohexyloxy)phenyl]propionic acid (2-1)

N-CBZ-L-tyrosine (15.0 g, 0.045 moles) was dissolved in 75 mL DMF and added at 0°–10° C. to a suspension of sodium hydride (2.16 g, 0.09 moles) in 25 mL DMF. The resulting suspension was stirred at 0°–10° C. for 1.0 hour and then 6-(t-butyloxycarbonylamino)hexyl bromide (12.6 g, 0.045 moles) in 25 mL DMF was added dropwise at 0°–5° C. and the clear, dark reaction mixture was stirred at room temperature overnight.

After solvent removal, the residue was taken up in EtOAc and this was made acidic with 10% KHSO$_4$ solution. The organic phase was separated, washed with brine, dried (Na$_2$SO$_4$) and the solvent removed to give an oil. This was purified by column chromatography on silica gel eluting with 98:2:1 CHCl$_3$/CH$_3$OH/HOAc to give pure 2-1 as a clear oil. ¹H NMR (300 MHz, CD₃OD) δ 1.45 (15H, m), 1.75 (2H, m), 2.80–3.15 (6H, m), 3.91 (2H, t), 4.38 (1H, m), 4.95 (6H, m), 6.79 (2H, d), 7.10 (2H, d), 7.28 (5H, m).

EXAMPLE 9

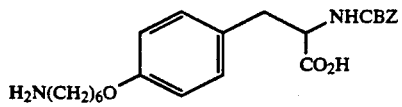

2-S-(N-Benzyloxycarbonylamino)-3-[4-(6-aminohexyloxyphenyl)]propionic acid hydrochloride (2-2)

Compound 2-1 (51.4 mg, 0.1 mmole) was dissolved in 20 mL EtOAc and cooled to −20° C. under N₂. HCl gas was bubbled into this solution for 10 minutes as the temperature rose to −5° C. The reaction mixture was stoppered and stirred at 0° to −5° C. for 1 hour. The solvent was then removed on the rotary evaporator and the residue was triturated with ether to give 2-2 (14.2 mg) as a white solid. R$_f$=0.4 (SiO₂, 9:1:1 EtOH/NH₄OH, H₂O).

¹H NMR (300 MHz, CD₃OD) δ 1.45 (6H, m), 1.73 (4H, m), 2.90 (3H, m), 3.13 (1H, m), 3.95 (2H, m), 4.30 (1H, bs), 6.77 (2H, d), 7.10 (2H, d), 7.32 (4H, m).

Analysis for C₂₃H₃₁N₂O₅Cl.0.5 H₂O: Calcd: C, 60.05; H, 7.01; N, 6.09; Found: C, 60.08; H, 7.06; N, 6.09.

EXAMPLE 10

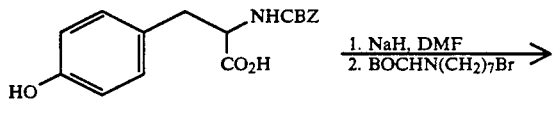

2-S-(N-Benzyloxycarbonylamino)-3-[4-(7-N-t-butyloxycarbonylaminoheptyloxy)phenyl]propionic acid (2-3)

N-CBZ-L-tyrosine (1.27 g, 4.02 mmoles) was alkylated with 7-(N-t-butyloxycarbonylaminoheptyl)bromide as taught in Example 8 for compound 2-1. Crude product was purified by flash chromatography on silica gel eluting with 95:5:0.5 CHCl₃/CH₃OH/HOAc to give 1.05 g (50%) of 2-3 as a clear oil.

¹H NMR (300 MHz, CD₃OD) δ 1.40 (20H, m), 1.66 (2H, m), 2.82 (1H, m), 2.97–3.18 (4H, m), 3.91 (2H, m), 4.19 (1H, m) 5.0 (2H, q), 6.77 (2H, d), 7.10 (2H, d), 7.30 (5H, m).

EXAMPLE 11

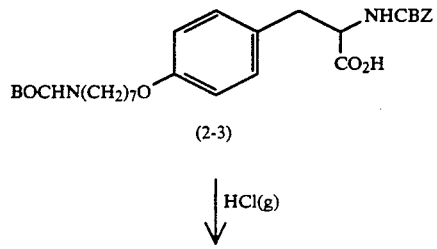

EXAMPLE 12

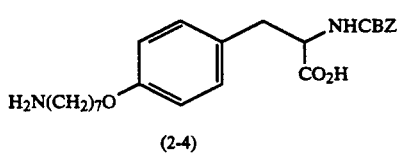

(2-4)

2-S-(N-Benzyloxycarbonylamino)-3-[4-(7-aminoheptyloxy)phenyl]propionic acid hydrochloride (2-4)

Compound 2-3 (67.4 mg, 0.127 mmole) was deprotected with HCl gas as described in Example 9 for 2-2 to provide 60.0 mg pure 2-4.

¹H NMR (300 MHz, CD₃OD) δ 1.32 (9H, m), 1.60 (4H, m), 2.77 (3H, m), 3.00 (1H, m), 3.18 (2H, m), 3.72 (2H, m), 4.25 (1H, m), 4.90 (2H, q), 6.70 (2H, d), 7.00 (2H, d), 7.18 (5H, m).

Analysis for C₂₄H₃₂N₂O₅.0.2EtOH.0.75 H₂O: Calcd: C, 64.94; H, 7.75; N, 6.21; Found: C, 64.97; H, 7.84; N, 6.22.

EXAMPLE 12

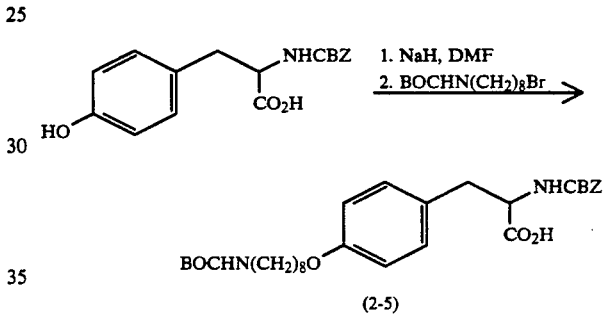

2-S-(N-Benzyloxycarbonylamino)-3-[4-(8-N-t-butyloxycarbonylaminooctyloxy)phenyl]propionic acid (2-5)

N-CBZ-L-tyrosine.H₂O (1.5 g, 4.29 mmole) was dissolved in EtOAc/CH₂Cl₂, dried over MgSO₄, filtered and evaporated. The residue was dissolved in DMF and treated with NaH (50% dispersion in oil, 0.43 g, 8.96 mmole) for 1 hour. N-BOC-8-amino-1-bromooctane (1.33 g, 4.34 mmole) was added and the reaction was stirred for 16 hours. The DMF was removed in vacuo, the residue dissolved in water, acidified to pH 3 and extracted with EtOAc. The EtOAc layers were combined, dried and concentrated. Column chromatography (SiO₂, 97:3:1 CHCl₃/MeOH/HOAc) gave 2-5 (1.35 g) (57% yield).

¹H NMR (300 MHz, CD₃OD) δ 7.3 (m, 5H), 7.1 (d, 2H), 6.78 (d, 2H), 5.0 (2q, 2H), 4.38 dd, 1H), 3.8 (m, 2H), 3.13 (dd, 1H), 3.0 (t, 2H), 2.85 (dd, 1H), 1.75 (m, 2H), 1.4 (s, 9H), 1.35 (m, 3H), 1.3 (bs, 7H).

EXAMPLE 13

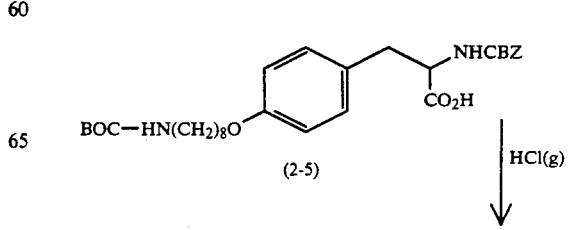

-continued

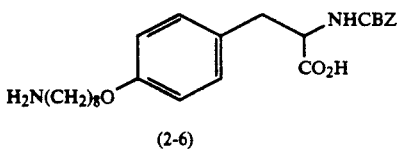

(2-6)

-continued

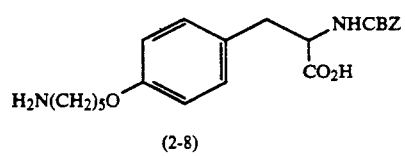

(2-8)

2-S-(N-Benzyloxycarbonylamino)-3-[4-(8-aminooctyloxy)phenyl]propionic acid (2-6)

Compound 2-5 (1.35 g, 2.49 mmole) was dissolved in ethyl acetate and treated with HCl gas at −20° C., purged with $N_2$ and concentrated to give a white solid which was rinsed with ethyl acetate and dried to give 0.965 g of product.

$^1$H NMR (300 MHz, CD$_3$OD) δ 7.3 (m, 5H), 7.1 (d, 2H), 6.8 (d, 2H), 5.02, (2q, 2H), 4.35 (dd, 1H), 4.03 (t, 2H), 3.1 (dd, 1H), 2.9 (t, 2H), 2.85 (dd, 1H), 1.75 (m, 2H), 1.65 (m, 2H), 1.5 (m, 2H), 1.4 (bs, 6H).

Analysis for $C_{25}H_{34}N_2O_5$.HCl.0.65 H$_2$O: MW=490.732; Calcd: C, 61.18; H, 7.46; N, 5.71; Found: C, 61.18; H, 7.45; N, 5.77.

EXAMPLE 14

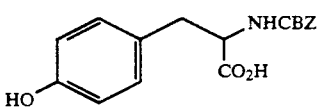

↓ 1. NaH, DMF
2. BocHN(CH$_2$)$_5$Br

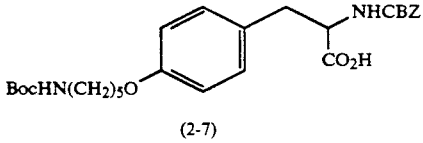

(2-7)

2-S-(N-Benzyloxycarbonylamino)-3-[4-(5-N-t-butyloxycarbonylaminopentyloxy)phenyl]propionic acid (2-7)

N-CBZ-L-tyrosine (1.06 g, 3.01 mmole) was alkylated with 5-N-t-(butyloxycarbonylaminopentyl) bromide as described for compound 2-1 in Example 8. Crude product was purified by flash chromatography on silica gel eluting with 97:3:0.5 CHCl$_3$/CH$_3$OH/HOAc to give pure 2-7.

$^1$H NMR (300 MHz, CD$_3$OD)δ 1.42 (9H, S), 1.52 (4H, m), 1.76 (2H, m), 3.05, (3H, m), 3.92 (2H, t), 5.00 (2H, m), 6.79 (2H, d), 7.11 (2H, d), 7.28 (5H, m).

EXAMPLE 15

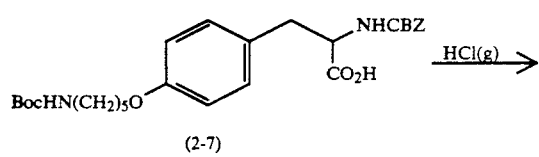 $\xrightarrow{HCl(g)}$ (2-7)

2-S-(N-Benzyloxycarbonylamino)-3-[4-(5-amino-pentyloxy)phenyl]propionic acid hydrochloride (2-8)

2-7 was treated with HCl gas as taught in Example 9 for compound 2-2, to provide pure 2-8 as a white powder.

$^1$H NMR (300 MHz, CD$_3$OD)δ 1.60 (2H, m), 1.77 (4H, m), 2.90 (3H, m), 3.12, (1H, m), 3.96 (2H, t), 4.37 (1H, m), 5.02 (2H, m), 6.81 (2H, d), 7.12 (2H, d), 7.30 (5H, m).

Analysis for $C_{22}H_{29}N_2O_5$.0.25 H$_2$O: Calcd: C, 59.85; H, 6.74; N, 6.35; Found: C, 59.85; H, 6.73; N, 6.32.

EXAMPLE 16

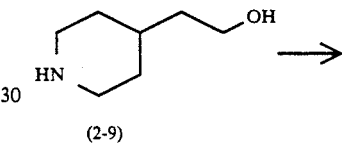 →

(2-9)

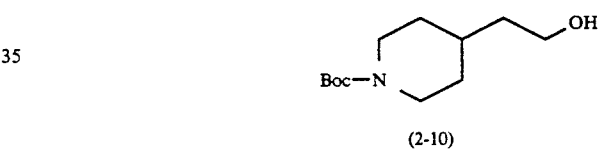

(2-10)

2-(4-N-t-Butyloxycarbonylpiperidinyl)ethanol (2-10)

4-piperidine-2-ethanol (Available from American Tokyo Kasei) (130 g, 1.0 mole) was dissolved in 700 mL dioxane, cooled to 0° C. and treated with 3N NaOH (336 mL, 1.0 mole), and di-t-butylcarbonate (221.8 g, 1.0 mole). The ice bath was removed and the reaction stirred overnight. The reaction was concentrated, diluted with water and extracted with ether. The ether layers were combined, washed with brine, dried over MgSO$_4$, filtered and evaporated to give 225.8 g of product (98%).

R$_f$=0.37 in 1:1 EtOAc/Hexanes, ninhydrin stain.

300 MHz $^1$H NMR (CDCl$_3$) δ 4.07 (bs, 2H), 3.7 (bs, 2H), 2.7 (t, J=12.5 Hz, 2H), 1.8–1.6 (m, 6H), 1.51 (s, 9H), 1.1 (ddd, J=4.3, 12.5, 12 Hz, 2H).

EXAMPLE 17

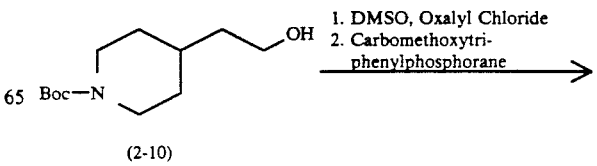 $\xrightarrow{\text{1. DMSO, Oxalyl Chloride} \atop \text{2. Carbomethoxytriphenylphosphorane}}$ (2-10)

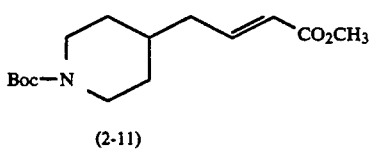

(2-11)

Methyl 4-(4-N-t-Butyloxycarbonylpiperidinyl)-but-2-enoate (2-11)

Oxalyl chloride (55.8 mL, 0.64 mole) was dissolved in 1 L CH$_2$Cl$_2$ and cooled to −78° C. under N$_2$. DMSO (54.2 mL, 0.76 mole) was added dropwise. After gas evolution had ceased, 2-10 (102.5 g, 0.45 mole) dissolved in 200 mL CH$_2$Cl$_2$ was added over 20 minutes. After stirring an additional 20 minutes, triethylamine (213 mL, 1.53 mole) was added dropwise and the cold bath removed. After 1 and ½ hours TLC showed starting material gone. Carbomethoxytriphenylphosphorane (179 g, 0.536 mole) was added and the reaction stirred overnight. The solution was diluted with 300 mL Et$_2$O, extracted once with 800 mL H$_2$O, twice with 300 mL 10% KHSO$_4$ solution, then once with 300 mL brine. The organic layer was dried over MgSO$_4$, filtered and evaporated. Column chromatography (SiO$_2$, 5% EtOAc/Hexanes) yielded 78.4 g (62%) of pure 2-11.

300 MHz $^1$H NMR (CDCl$_3$) δ 6.9 (ddd J=15.6, 7.6, 7.6 Hz, 1H), 5.8 (d, J=15.6 Hz, 1H), 4.0 (bs, 2H), 3.7 (s, 3H), 2.6 (t, J=12.6 Hz, 2H), 2.1 (t, J=7.4 Hz, 2H), 1.7–1.4 (m, 3H), 1.4 (s, 9H), 1.1 (m, 2H).

EXAMPLE 18

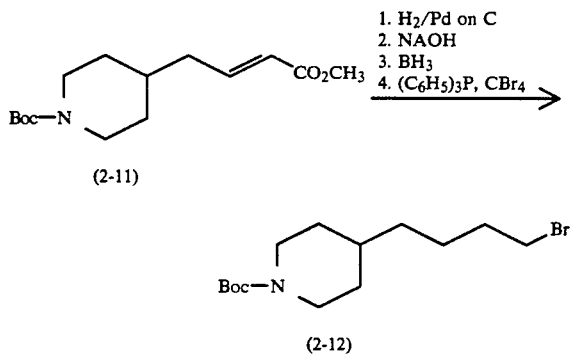

4-(4-N-t-Butyloxycarbonylpiperidinyl)butyl bromide (2-12)

Compound 2-11 (36.2 g, 0.128 mole), was dissolved in 500 mL EtOAc. 10% Palladium on carbon (10 g) was added as a slurry in EtOAc and the reaction was placed under H$_2$ (in a balloon) overnight. The reaction was filtered through Solka-Floc, the cake washed with EtOAc and the ethyl acetate evaporated to give 34.7 g (90%) of 4-(4-N-t-butyloxycarbonylpiperidin-4-yl)butanoate. TLC R$_f$=0.69 in 30% EtOAc/Hexanes.

$^1$H NMR (300 MHz, CDCl$_3$) δ 4.0 (bs, 2H), 3.6 (s, 3H), 2.60 (t, J=12.3 Hz, 2H), 2.20 (t, J=7.4, 2H), 1.6 (m, 4H), 1.40 (s, 9H), 1.40 (m, 1H), 1.20 (m, 2H), 1.0 (m, 2H).

The butanoate ester (45.3 g, 0.159 mole) was dissolved in CH$_3$OH and treated with 1N NaOH (500 mL, 0.5 mole) overnight. The solvent was removed in vacuo, water was added and the solution washed with ether, then acidified with 10% KHSO$_4$ solution. The aqueous layer was washed with ether, the ether layers were combined, washed with brine, dried (MgSO$_4$), and concentrated to give the corresponding acid as a clear oil (41.85 g, 97% yield).

$^1$H NMR (300 MHz, CDCl$_3$) δ 4.0 (bs, 2H), 2.6 (m, 2H), 2.25 (m, 2H), 1.6 (bs, 4H), 1.4 (s, 9H), 1.3–0.9 (9H).

This acid (20.4 g, 0.077 moles) was treated with borane (BH$_3$/THF, 235 mL, 235 mmole) in THF at 0° for 1 hour. NaOH (1N, 250 mL) was added dropwise and the solution stirred overnight. The reaction was concentrated to remove THF and extracted with ether. The ether extracts were combined, dried over MgSO$_4$, filtered and evaporated to give the corresponding alcohol as 19.7 g of a colorless oil.

R$_f$=0.7 in 2:1 ethyl acetate/hexanes.

$^1$H NMR (300 MHz, CDCl$_3$) δ 4.1 (bs, 2H), 3.6 (t, 2H), 2.65 (t, 2H), 2.1 (bs, 1H), 1.65 (bs, 2H), 1.55 (m, 2H), 1.4 (s, 9H), 1.35 (m, 3H), 1.25 (m, 2H), 1.1 (m, 2H).

This alcohol (19.7 g, 76.5 mmole) was dissolved in THF and treated with triphenylphosphine (23.1 g, 88 mmol) and cooled to 0° C. Carbon tetrabromide (29.8 g, 89.9 mmol) was added in one portion, the cold bath was removed and the reaction stirred overnight. Additional triphenyl phosphine (11.71 g) and carbon tetrabromide (14.9 g) was added to drive the reaction to completion. The mixture was filtered and the liquid was diluted with ether and filtered again. After solvent removal the resulting liquid was adsorbed onto SiO$_2$ and chromatographed with 5% EtOAc/Hexanes to yield 2-12 as a clear colorless oil (20.7 g, 85% yield).

R$_f$=0.6 in 1:4 ethyl acetate/hexanes $^1$H NMR (300 MHz, CDCl$_3$) δ 4.1 (bs, 2H), 3.4 (t, 2H), 2.65 (t, 2H), 1.85 (m, 2H), 1.65 (bd, 2H), 1.4 (s, 9H), 1.35 (m, 2H), 1.3 (m, 3H), 1.1 (m, 2H).

EXAMPLE 19

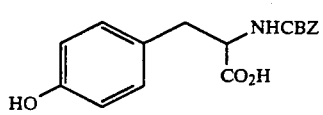
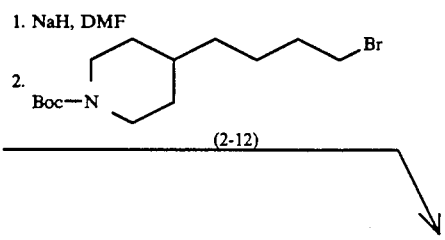

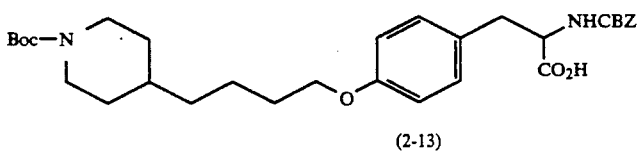

(2-13)

EXAMPLE 21

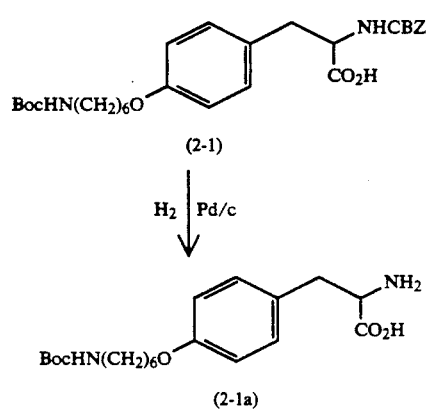

2-S-(N-(Benzyloxycarbonylamino)-3-[4-(4-N-t-butyloxycarbonylpiperidin-4-ylbutyloxy)phenyl]propionic acid (2-13)

N-CBZ-L-tyrosine was alkylated with 2-12 as taught for compound 2-5 in Example 12 to provide 2-13 in 87% yield.

$R_f$=0.15 in 97:3:1 $CHCl_3/CH_3OH/HOAc$, iodine stain.

$^1$H NMR (300 MHz, $CDCl_3$) δ 7.2 (d, J=7.5 Hz, 2H), 7.1 (d, J=7.5 Hz, 2H), 7.0 (d, J=7.3 Hz, 2H), 6.8 (d, J=7.3 Hz, 2H), 5.2 (d, J=7.9 Hz, 1H), 5.1 (s, 2H), 4.6 (m, 1H), 4.01 (bd, 2H), 3.92 (t, J=6 Hz, 2H), 6.7 (m, 2H), 2.65 (bt, 7H), 1.75-1.4 (m, 7H), 1.45 (s, 9H), 1.3 (m, 2H), 1.1 (m, 2H).

EXAMPLE 20

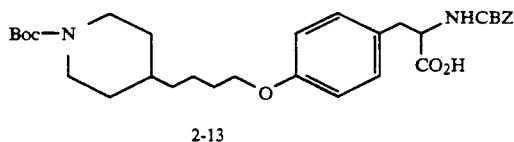

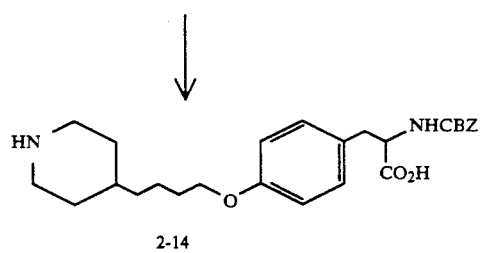

2-S-(N-(Benzyloxycarbonylamino)-3-[4-(4-piperidin-4-ylbutyloxy)phenyl]propionic acid (2-14)

Compound 2-13 was deprotected as taught for compound 2-2 in Example 9. The solvent was removed on the rotary evaporator and the residue was dissolved in water and extracted with ethyl acetate. The water layer was concentrated to dryness, evaporated and the residue was chromatographed ($SiO_2$, 9:1:1 $EtOH/H_2O/NH_4OH$). A small portion was then purified further by HPLC and isolated as the TFA salt.

$^1$H NMR (300 MHz, $CD_3OD$) d 7.3 (m, 5H), 7.1 (d, 2H), 6.8 (d, 2H), 5.0 (q, 2H), 2.93 (t, 2H), 2.85 (dd, 1H), 1.92 (bd, 2H), 1.75 (m, 2H), 1.6-1.45 (m, 3H), 1.35 (m, 4H).

Mass Spec. (FAB) m/e=455 (m+1).

EXAMPLE 22

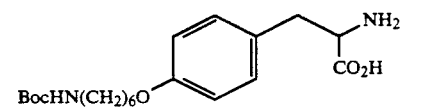

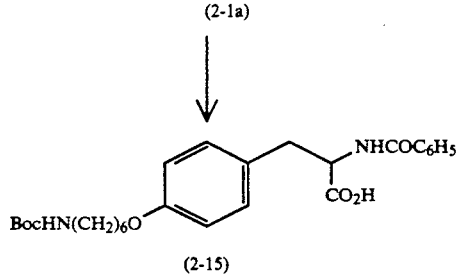

2-S-Amino-3-[4-(6-N-t-butyloxycarbonylaminohexyloxy)phenyl]propionic acid (2-1a)

A solution of compound 2-1 (0.52 g, 1.0 mmole) in 20 mL of 4:1 ethanol/HOAc was hydrogenated under balloon pressure for 8 hours. The catalyst was filtered off and the solvent removed on the rotary evaporator to give a residue that was triturated with 30 mL ether to provide 0.16 g of 2-1a.

$^1$H NMR (300 MHz, $CD_3OD$) δ 1.40 (9H, m), 1.75 (2H, m), 2.90-3.05 (3H, m), 3.10-3.23 (3H, m), 3.70 (1H, m), 3.96 (3H, t), 6.88 (2H, d), 7.20 (2H, d).

2-S-(Phenylcarbonylamino)-3[4-(6-N-t-butyloxycarbonylaminohexyloxy)phenyl] propionic acid (2-15)

0.152 g (0.4 mmole) of compound 2-1a was added to a solution of 1N NaOH (0.4 ml) in 10 mL $H_2O$ and this was stirred at 0°-5° C. for 10 minutes as most of the solid dissolved. To this vigorously stirred suspension was added benzoyl chloride (0.062 g, 0.44 mmole) followed by solid sodium bicarbonate (0.037 g, 0.44 mmol)

and the resulting mixture was stirred at 0°–5° C. for 1 hour.

The reaction mixture was then diluted with 30 mL H₂O and acidified to pH 2–3 with 10% KHSO₄ solution. This was extracted with 3×50 mL EtOAc and the combined organic extract was washed with 30 mL of H₂O, 30 mL of brine and dried (Na₂SO₄). Solvent removal provided a viscous residue that was purified by flash chromatography on silica gel eluting with chloroform(95)-methanol(5) to give 2-15 as a viscous residue.

¹H NMR (300 MHz, CDCl₃) δ 1.40 (9H, m), 1.75 (2H, bs), 3.20 (m, 4H), 3.92 (2H, m), 5.03 (2H, m), 6.79 (2H, d), 7.10 (2H, d), 7.45 (3H, m), 7.72 (2H, m).

EXAMPLE 23

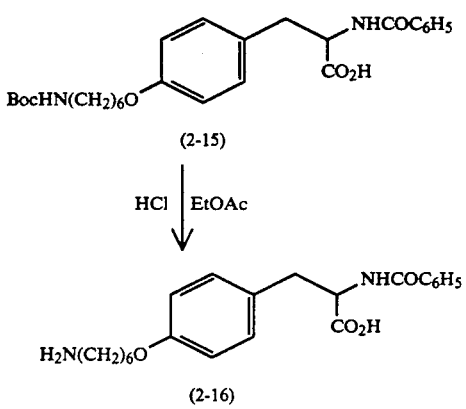

2-S-(Phenylcarbonylamino)-3-[4-(6-aminohexyloxy)-phenyl]-propionic acid hydrochloride (2-16)

0.28 g (2.0 mmole) of compound 2-15 was dissolved in 20 mL of EtOAc and this was cooled to −15° C. and HCl gas was bubbled into the solution for 10 minutes. The resulting mixture was stoppered and stirred at 0° C. for 1.5 hours at which point all starting material was consumed. The solvent was then removed on the rotary evaporator to afford a white, foam-like residue. This was stirred with 30 mL ether for 1 hour and the resulting solid was collected by filtration to provide pure 2-16 as a white solid.

¹H NMR (300 MHz, CD₃OD), δ 1.50 (3H, m), 1.70 (2H, m), 1.78 (2H, m), 2.90 (2H, t), 3.21 (4H, m), 3.94 (2H, t), 6.80 (2H, d), 7.19 (2H, d), 7.42 (2H, m), 7.50 (1H, m), 7.72 (2H, d).

Analysis for C₂₂H₃₈N₂O₄·HCl·0.75 H₂O: Calc.: C=60.82, H=6.90, N=6.45; Found: C=60.89, H=6.67, N=6.35.

EXAMPLE 24

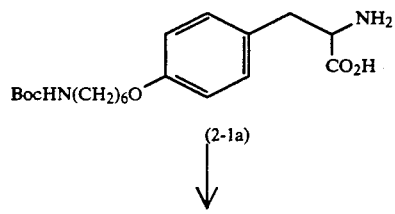

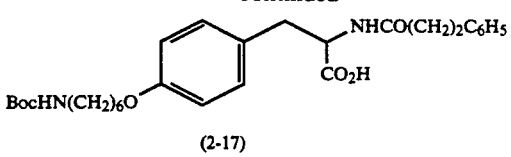

2-S-(Phenethylcarbonylamino)-3[4-(6-N-t-butyloxy carbon-ylaminohexyloxy)phenyl]propanoic acid (2-17)

To a stirred solution of 1.2 mL 1N NaOH in 15 mL H₂O cooled to 0°–5° C. was added 0.457 g (1.2 mmole) of compound 2-1a and the resulting mixture was stirred for 10 minutes during which time most of the solid dissolved. To this vigorously stirred suspension was then added 3-phenylpropanoyl chloride (0.223 g, 1.32 mmole) followed by solid sodium carbonate (0.111 g, 1.32 mmole). The resulting white mixture was stirred vigorously at 0°–5° C. for 1.5 hours. The reaction mixture was then diluted with 40 mL H₂O and this was acidified to pH 2–3 with a 10% KHSO₄ solution. The resulting aqueous phase was then extracted with 4×50 mL portions of EtOAc, and the combined organic phase was washed with 50 mL H₂O, 50 mL brine and dried (Na₂SO₄). Solvent removal gave a viscous solid that was purified by flash chromatography on silica gel, eluting with chloroform (95)-methanol(5) to give 0.30 g of pure 2-17 as a clear viscous gum.

¹H NMR (300 MHz, CDCl₃) δ 1.40 (9H, m), 1.72 (2H, bs), 2.50 (2H, m), 3.02 (6H, m), 3.91 (2H, m), 6.72 (2H, d), 6.88 (2H, m), 7.20 (3H, m), 7.29 (2H, m).

EXAMPLE 25

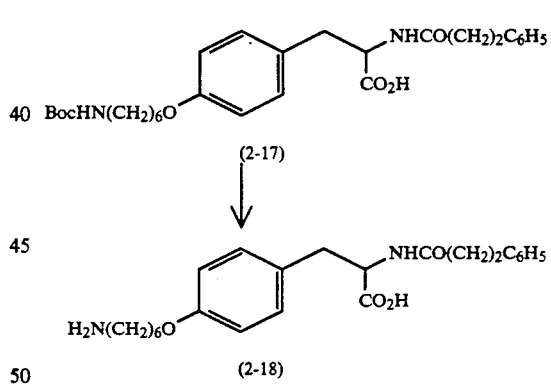

2-S-(Phenethylcarbonylamino)-3-[4-(6-aminohexyloxy)phenyl]propanoic acid hydrochloride (2-18)

A solution of compound 2-17 (0.3 g, 3.0 mmole) in 15 mL EtOAc was cooled to −15° C. and HCl gas was bubbled in for 10 minutes. The stoppered reaction mixture was then stirred for 2 hours at 0° C. at which time all 2-17 was consumed. The solvent was then removed on the rotary evaporator and the resulting foam was triturated with 40 mL ether at room temperature for 1.0 hour to give pure 2-18 as a white solid, 0.22 g.

¹H NMR (300 MHz, CD₃OD) δ 1.48 (3H, m), 1.67 (2H, m), 1.80 (2H, m), 2.46 (2H, m), 2.80 (3H, m), 2.90 (2H, m), 3.30 (3H, m), 3.95 (2H, t), 6.79 (2H, d), 7.06 (2H, d), 7.15 (3H, m), 7.22 (2H, m).

Analysis for C₂₄H₃₂N₂O₄·HCl·H₂O: Calc.: C=61.72, H=7.55, N=6.00; Found: C=61.97, H=7.11, N=5.96.

EXAMPLE 26

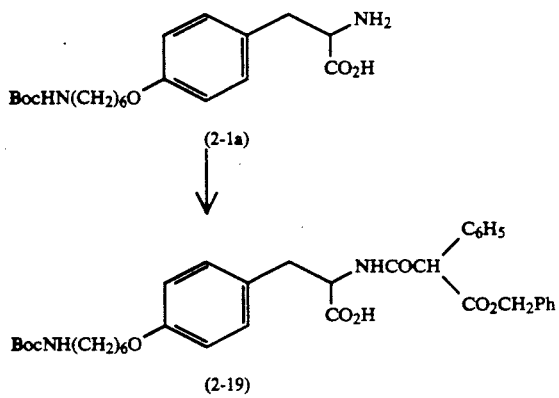

2-S-(2-N-2-Benzyloxycarbonyl)phenylacetylamino-3[4-(6-N-t-butyloxycarbonylaminohexyloxy)phenyl]propionic acid (2-19)

To a cold solution of 1.8 mL of 1N NaOH in 15 mL $H_2O$ was added 0.685 g (1.8 mmole) of compound 2-1a with stirring to give, after 10 minutes, a clear solution. Then, 2-benzyloxycarbonylphenylacetyl chloride (0.577 g, 2.0 mmole) was added followed by sodium bicarbonate (0.168 g, 2.0 mmole) and the resulting mixture was stirred at 0°-5° C. for 1.0 hour. The reaction mixture was diluted with water, acidified to pH 2-3 with 10% $KHSO_4$ solution and extracted with 4×500 mL portions of EtOAc. The combined organic extracts were washed with brine, dried ($Na_2SO_4$) and the solvent was removed to give a viscous amber residue. This was purified by column chromatography on silica gel, eluting with $CHCl_3$ (98)-methanol (2) to give 0.326 g of pure 2-19 as an oil.

$^1H$ NMR (300 MHz $CDCl_3$) δ 1.45 (9H, 6s), 1.75 (2H, 6s), 3.07 (4H, m), 3.89 (2H, bs), 4.57 (2H, bs), 5.15 (2H, m), 6.69 (2H, d), 6.88 (2H, d), 7.30 (5H, m).

EXAMPLE 27

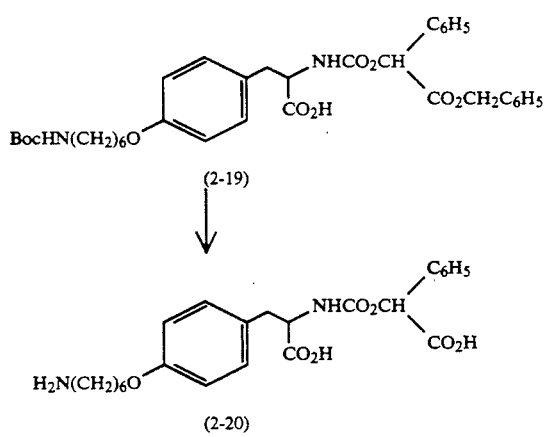

2-S-(2-Carboxyphenylacetylamino)-3-[4-(6-aminohexyloxy)phenyl]propionic acid hydrochloride (2-20)

Compound 2-19 (0.34 g, 0.55 mmole) was dissolved in 25 mL absolute ethanol and after adding 100 mg 10% Pd/C the suspension was hydrogenated under balloon pressure. Then, the catalyst was filtered off and the solvent removed on the rotary evaporator to give 0.25 g of 2-S(2-Carboxyphenylacetylamino)-3-[4-(6-t-butyloxycarbonylaminohexyloxy)phenyl]propionic acid.

$^1H$ NMR (300 MHz, $CD_3OD$) δ 147 (12H, m), 1.78 (2H, m), 3.06 (3H, m), 3.32 (4H, m), 3.92 (2H, m), 4.60 (2H, m), 6.72 (2H, d), 6.96, (2H, d), 7.30 (5H, m).

This acid was dissolved in 25 mL EtOAc and treated with HCl gas as described for compound 2-2 in Example 9. Solvent removal provided a residue that was purified by flash chromatography on silica gel eluting with 9:1:1 ethanol/$H_2O$/$NH_4OH$ to give pure 2-20.

$^1H$ NMR (300 MHz, $D_2O$) δ 1.55 (H, m), 1.90 (2H, m), 2.83-3.09 (4H, m), 3.28 (1H, m), 4.15 (2H, m), 6.88-7.45 (9H, m).

Analysis for $C_{24}H_{30}N_2O_6 \cdot 1.5\ H_2O \cdot 0.25\ NH_3$; Calc.: C=60.84, H=7.18, N=6.65; Found: C=60.48, H=6.81, N=6.99.

EXAMPLE 28

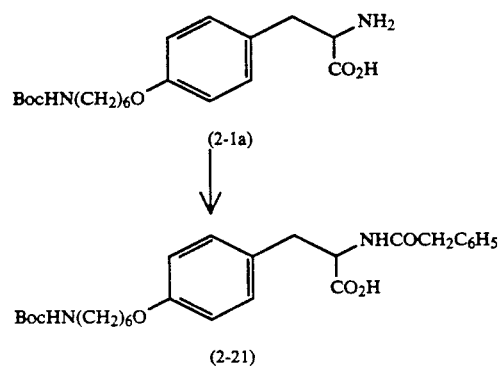

2-S-(Phenylacetylamino)-3-[4-(6-N-t-butyloxycarbonylaminohexyloxy)phenyl]propionic acid (2-21)

Compound 2-1a (0.685 g, 1.8 mmole) was acylated with phenylacetyl chloride as described for compound 2-19 in Example 26. The crude product was purified by flash chromatography on silica gel eluting with 95:5:0.5 $CHCl_3/CH_3OH/HOAc$ to give pure 2-21 as a viscous oil. (0.35 g).

$^1H$ NMR (300 MHz, $CD_3OD$) δ 1.45 (12H, m), 1.78 (2H, m), 2.88 (1H, m), 3.10 (3H, m), 3.30 (1H, m), 3.48 (2H, m ), 3.92 (2H, m), 4.61 (1H, m), 6.74 (2H, d), 7.02 (2H, d), 7.12 (2H, m) 7.22 (3H, m).

EXAMPLE 29

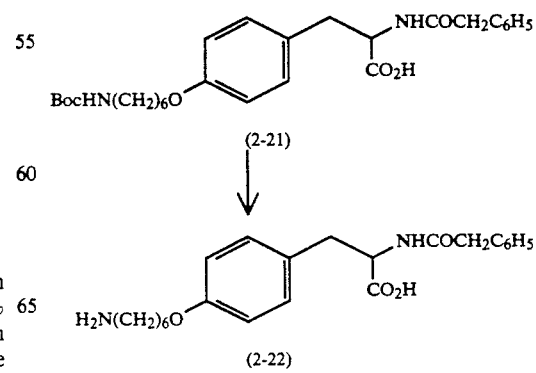

2-S-(Phenylacetylamino)-3-[4-(6-aminohexyloxy)-phenyl]propionic acid (2-22)

Compound 2-21 (0.35 g) was dissolved in 25 mL EtOAc and this solution was treated with HCl gas as described for compound 2-16 in Example 23 to give 0.26 g pure 2-22 as a white solid.

$^1$H NMR (300 MHz, CD$_3$OD) δ 1.50 (6H, m), 1.65 (2H, m), 2.20 (2H, m), 2.88 (3H, m), 3.12 (1H, m), 3.30 (2H, m), 3.47 (2H, m), 3.94 (2H, m), 4.61 (1H, m), 6.75 (2H, d), 7.02 (2H, d), 7.13 (2H, d), 7.30 (3H, m).

Analysis for C$_{23}$H$_{30}$N$_2$O$_4$.HCl.H$_2$O: Calc.: C=60.98, H=7.34, N=6.19; Found: C=61.29, H=6.92, N=6.12.

EXAMPLE 30

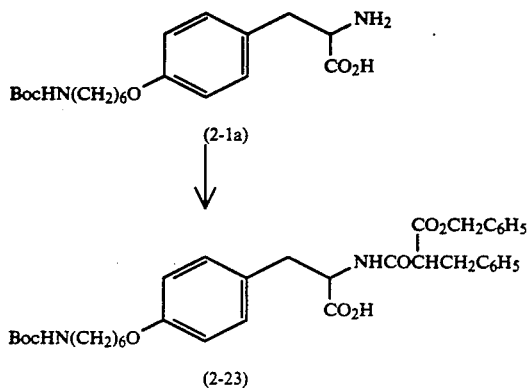

2-S-[(2-N-Benzyloxycarbonyl-3-phenylpropionylamino]-3-[4-(6-N-t-butyloxycarbonylaminohexyloxy)phenyl]propionic acid (2-23)

Compound 2-1a (0.685 g, 1.8 mmole) was acylated with 2-N-benzyloxycarbonyl-3-phenylpropionylchloride as described for compound 2-19 in Example 26. The crude product was purified by flash chromatography on silica gel eluting with 98:2:1 CHCl$_3$/CH$_3$OH/HOAc to give pure 2-23 as a viscous oil.

$^1$H NMR (300 MHz, CD$_3$OD) δ 1.40 (16H, m), 1.61 (2H, m), 3.03 (8H, m), 3.30 (6H, m), 3.71 (1H, m), 3.86 (2H, m), 4.60 (1H, m), 5.02 (2H, m), 6.70 (2H, d), 6.86, (1H, d), 7.02 (1H, 3), 7.22 (5H, m).

EXAMPLE 31

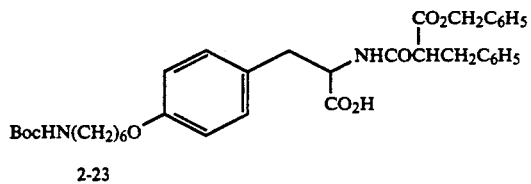

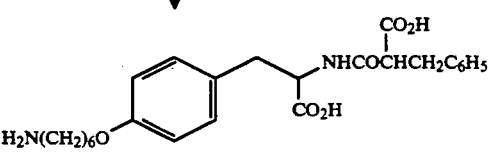

2-S-(2-Carboxy-3-phenylpropionylamino)-3-[4-(6-aminohexyloxy)phenyl]propionic acid (2-24)

Compound 2-23 (0.49 g, 0.76 mmole) was dissolved in 25 mL ethanol and after the addition of 100 mg 10% Pd/C was hydrogenated at balloon pressure overnight. Solvent removal provided 2-S-(2-carboxy-3-phenylpropionylamino)-3-[4-(6-N-t-butyloxycarbonylaminohexyloxy)phenyl]propionic acid as a viscous residue (0.35 g).

$^1$H NMR (300 MHz, CD$_3$OD) δ 1.42 (10H, m), 1.75 (2H, m), 2.80–3.15 (5H, m), 3.30 (1H, m), 3.90 (2H, m), 4.58 (2H, m), 6.68–6.85 (4H, m), 7.06–7.27 (5H, m).

This acid (0.32 g) was treated with HCl gas as described for compound 2-12 to give after solvent removal a crude product that was purified by flash chromatography on silica gel eluting with 90:5:5 CHCl$_3$/CH$_3$OH/HOAc to provide the diastereomeric products 2-24a and 2-24b.

2-24a had $^1$H NMR (300 MHz, D$_2$O) δ 1.58 (4H, m), 1.83 (4H, m), 2.95 (2H, m), 3.08 (3H, m), 3.20 (1H, m), 3.51 1H, m), 4.18 (2H, m), 4.53 (1H, m), 4.95 (2H, g), 6.92 (4H, m), 7.43 (5H, m).

2-24b had $^1$H NMR (400 MHz, D$_2$O) δ 1.40 (4H, m), 1.62 (2H, m), 1.73 (2H, m) 2.90 (6H, m), 3.31 (1H, m), 4.17 (2H, m), 4.32 (1H, m), 6.93 (2H, d), 7.07 (2H, d), 7.15 (2H, d), 7.26 (3H, m).

EXAMPLE 31(a)

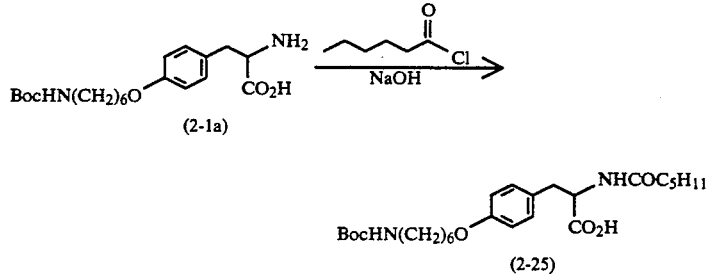

2-S-(Hexanoylamino)-3-[4-(6-N-t-butyloxycarbonylaminohexyloxy)phenyl]propionic acid (2-25)

2-1a (0.685 g, 1.8 mmole) was treated with hexanoyl chloride (0.38 g, 2.0 mmole) as described for 2-15 to provide crude 2-25. This was purified by flash chromatography on silica gel eluting with 95:5:1 CHCl₃/CH₃OH/HOAc to give pure 2-25 as an oil (0.35 g, 41%).

¹H NMR (300 MHz, CDCl₃) δ 0.89 (3H, t), 1.20–1.65 (21H, m), 1.75 (2H, m), 2.19 (2H, t), 3.11 (4H, m), 3.92 (2H, m), 4.83 (1H, m), 6.80 (2H, d), 7.05 (2H, d).

EXAMPLE 31(b)

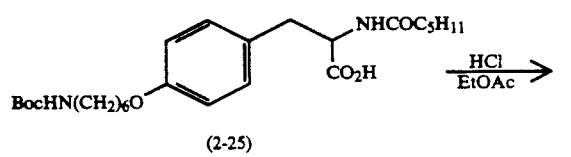

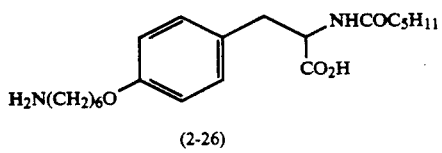

2-S-(Hexanoylamino)-3-[4-(6-aminohexyloxy)phenyl]-propionic acid hydrochloride (2-26)

2-25 (0.35 g, 0.75 mmole) was dissolved in 30 mL EtOAc and treated with HCl as described for compound 2-2 to give a foam-like solid that was triturated with 50 mL of ether for 1 hour at room temperature. This gave pure 2-26 as a white solid. (0.186 g).

¹H NMR (300 MHz, CD₃OD) δ 0.85 (3H, t), 1.20 (4H, m), 1.48 (6H, m), 1.68 (2H, m), 1.77 (2H, m), 2.14 (2H, m), 4.61 (1H, m), 6.80 (2H, d), 7.13 (2H, m).

Analysis for C₂₁H₃₄N₂O₄.HCl.0.5 H₂O: Calc: C=59.49, H=8.56, N=6.61; Found: C=59.32, H=8.48, N=6.55.

EXAMPLE 31(c)

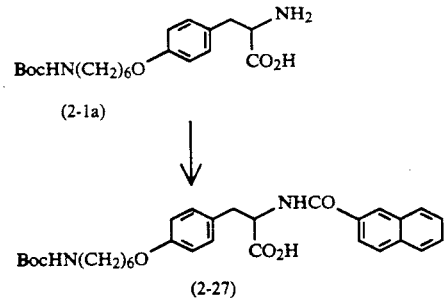

2-S-(2-Napthanoylamino)-3-[4-(6-N-t-butyloxycarbonylaminohexyloxy)phenyl]propionic acid (2-27)

2-1a (0.685 g, 1.8 mmole) was treated with 2-napthanoyl chloride (0.409 g, 2.0 mmole) as described for 2-15 to provide crude 2-27. This was purified by flash chromatography on silica gel eluting with 95:4:1 CHCl₃/CH₃OH/HOAc to give pure 2-27 as a white solid (0.14 g).

¹H NMR (300 MHz, CD₃OD) δ 1.45 (16H, m), 1.70 (2H, m), 2.88 (1H, m), 3.08 (3H, m), 3.57–3.80 (4H, m), 4.62 (1H, m), 6.54 (2H, d), 6.92 (2H, d), 7.25 (1H, d), 7.42 (2H, m), 7.61 (1H, bs), 7.77 (3H, m).

EXAMPLE 31 (d)

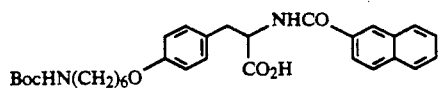

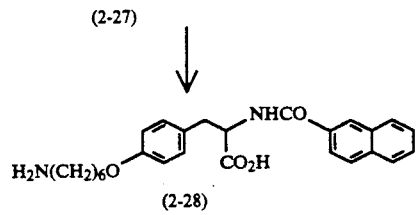

2-S-(2-Naphthanoylamino)-3-[4-(6-aminohexyloxy)-phenyl]propionic acid (2-28)

2-27 (0.14 g, 0.31 mmole) was dissolved in 25 mL EtOAc and treated with HCl gas as described for 2-2. Crude product was purified by flash chromatography on silica gel eluting with 10:1:1 C₂H₅OH/H₂O/NH₄OH to give pure 2-28 (55 mg) as a white solid.

¹H NMR (300 MHz, CD₃OD), δ 1.42 (5H, m), 1.71 (2H, m), 2.63 (2H, m), 2.86 (1H, m), 3.07 (2H, m), 3.30 (3H, m), 3.55–3.75 (4H, m), 4.47 (1H, m), 6.43 (2H, d), 6.82 (2H, d), 7.30 (1H, dd), 7.45 (2H, m), 7.64 (1H, bs), 7.80 (3H, m).

Analysis for C₂₇H₃₂N₂O₄.0.5 H₂O: Calc.: C=70.87, H=7.27, N=6.12; Found: C=70.93, H=7.04, N=6.11.

EXAMPLE 31 (e)

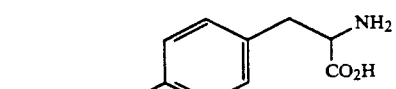

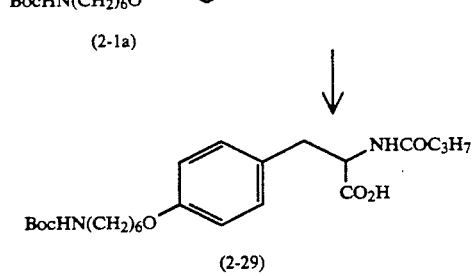

2-S-(2-Butanoylamino)-3-[4-(6-N-t-butyloxycarbonylaminohexyloxy)phenyl]propionic acid (2-29)

2-1a (0.685 g, 1.8 mmol) was acylated with butanoyl chloride as described for 2-15 to give crude 2-29. This was purified by flash chromatography eluting with 95:4:1 CHCl₃/CH₃OH/HOAc to provide pure 2-29 as an oil.

¹H NMR (300 MHz, CD₃OD) δ 0.73 (3H, t), 1.32–1.60 (16H, m), 1.73 (2H, m), 2.12 (2H, m), 2.87 (1H, m), 3.03 (2H, t), 3.12 (1H, m), 3.92 (2H, t), 4.61 (1H, m), 6.80 (2H, d), 7.12 (2H, d).

EXAMPLE 31(f)

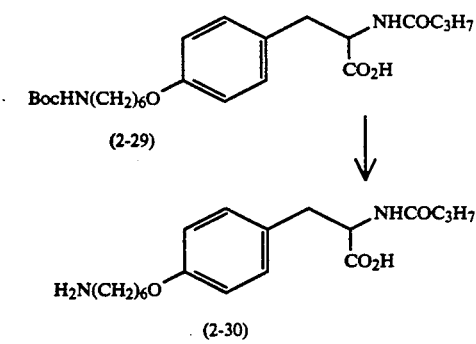

2-S-(Butanoylamino)-3-[4-(6-aminohexyloxy)-phenyl]-propionic acid (2-30)

2-29 (0.05 g, 1.0 mmole) was dissolved in 25 mL ethyl acetate and treated with HCl gas as described for 2-2. Crude reaction product was triturated with 25 mL ether to give pure 2-30 as a white solid.

$^1$H NMR (300 MHz, CD$_3$OD) δ 0.72 (3H, t), 1.45–1.60 (6H, m), 1.70 (2H, m), 1.79 (2H, m), 2.12 (2H, m), 2.80–2.95 (3H, m), 3.14 (1H, dd), 3.30 (1H, m), 3.95 (2H, t), 4.40 (1H, m), 6.80 (2H, d), 7.13 (2H, d).

Analysis for C$_{19}$H$_{30}$N$_2$O$_4$·HCl·H$_2$O; Calc.: C=56.35, H=8.21, N=6.92; Found: C=56.70, H=8.12, N=6.91.

EXAMPLE 31(g)

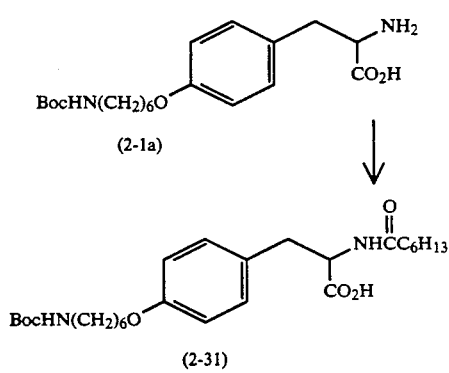

2-S-(Heptanoylamino)-3-[4-(6-N-t-butyloxycarbonylaminohexyloxy)phenyl]propionic acid (2-31)

2-1a (0.685 g, 1.8 mmole) was acylated with heptanoyl chloride as described for 2-15. Crude product was purified by flash chromatography on silica gel eluting with 96:3:1 CHCl$_3$/CH$_3$OH/HOAc to give pure 2-31 (0.07 g) as an oil.

$^1$H NMR (300 MHz, CD$_3$OD) δ 0.78 (3H, t), 1.22 (6H, m), 1.32–1.55 (16H, m), 1.73 (2H, m), 2.13 (2H, m), 2.85 (1H, m), 3.02 (2H, t), 3.15 (1H, m), 4.91 (2H, t), 4.61 (1H, m), 6.81 (2H, d), 7.12 (2H, d).

EXAMPLE 31(h)

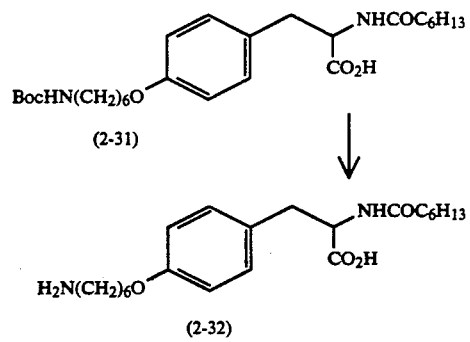

2-S-(Heptanoylamino)-3-[4-(6-aminohexyloxy)phenyl]-propionic acid hydrochloride (2-32)

2-31 (0.070 g) was dissolved in 30 mL EtOAc and treated with HCl gas as described for 2-2. Crude reaction product was triturated with 30 mL ether to provide pure 2-32 (52 mg) as a white solid.

$^1$H NMR (300 MHz, CD$_3$OD) δ 0.88 (3H, t), 1.22 (6H, m), 1.47 (6H, m), 1.68 (2H, m), 1.78 (2H, m), 2.13 (2H, t), 2.80–2.95 (3H, m), 3.14 (1H, m), 3.30 (1H, m), 3.94 (2H, m), 4.61 (1H, m), 6.80 (2H, d), 7.13 (2H, d).

Analysis for C$_{22}$H$_{36}$N$_2$O$_4$·HCl·0.75 H$_2$O: Calc.: C=59.71, H=8.77, N=6.33; Found: C=59.76, H=8.40, N=6.25.

EXAMPLE 31(i)

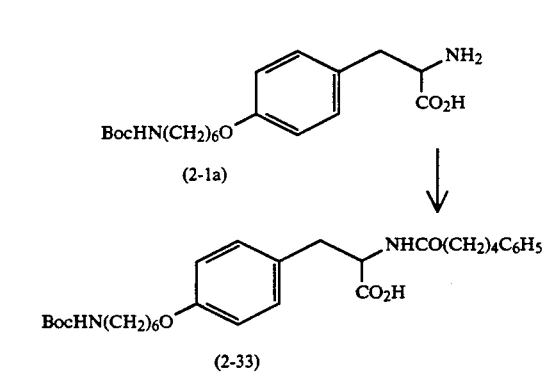

2-S-(5-Phenylpentanoylamino)-3-[4-(6-N-t-butyloxycarbonylaminohexyloxy)phenyl]propionic acid (2-33)

2-1a (0.685 g, 1.8 mmole) was acylated with 5-phenylpentanoyl chloride as described for 2-15. Crude product was purified by flash chromatography on silica gel eluting with 96:3:1 CHCl$_3$/CH$_3$OH/HOAc to give pure 2-33 (0.49 g) as a clear oil.

$^1$H NMR (300 MHz, CD$_3$OD) δ 1.32–1.60 (1H, m), 1.73 (2H, m), 2.18 (2H, m), 2.53 (2H, m), 2.80–2.90 (1H, m), 3.02 (2H, t), 3.04 (1H, m), 4.62 (1H, m), 6.78 (2H, d), 7.08–7.28 (7H, m).

EXAMPLE 31(j)

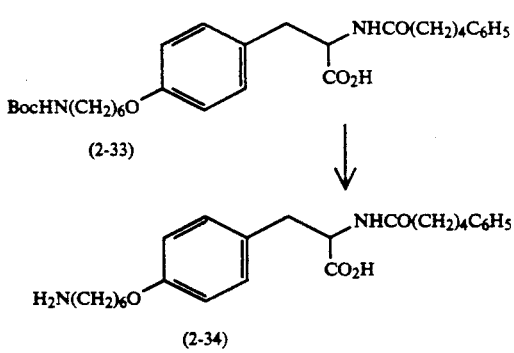

2-S-(5-Phenylpentanoylamino)-3-[4-(6-aminohexyloxy)-phenyl]propionic acid hydrochloride (2-34)

2-33 (0.49 g) was dissolved in 30 mL ethyl acetate and treated with HCl gas as described for 2-2. Crude product was triturated with 50 mL ether to give pure 2-34 (0.32 g) as a white solid.

$^1$H NMR (300 MHz, CD$_3$OD) δ 1.40–1.58 (8H, m), 1.62–1.70 (2H, m), 1.80 (2H, m), 2.19 (2H, m), 2.55 (2H, m), 2.80–2.95 (3H, m), 3.15 (1H, m, 3.30 (1H, m), 3.90 (2H, t), 4.62 (1H, m), 6.88 (2H, d), 7.08–7.27 (7H, m).

Analysis for C$_{26}$H$_{36}$N$_2$O$_4$.HCl.H$_2$O: Calc.: C=64.24, H=7.88, N=5.76; Found: C=64.53, H=7.84, N=5.71.

SCHEME 3

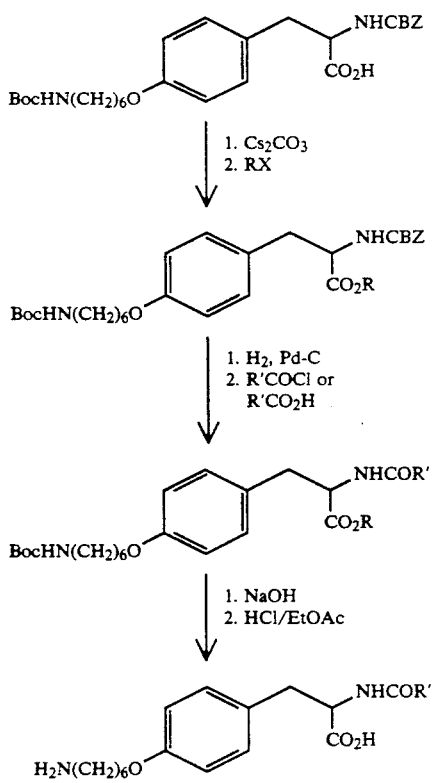

EXAMPLE 32

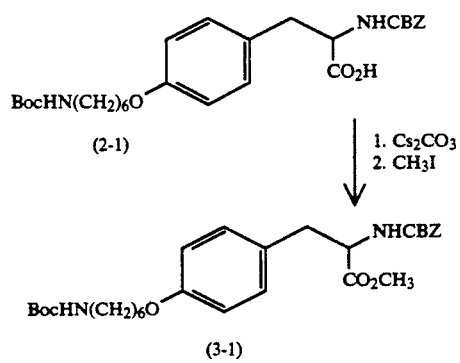

Methyl 2-S-(N-Benzyloxycarbonylamino)-3-[4-(6-N-t-butyloxycarbonylaminohexyl)oxyphenyl]propionate (3-1)

Compound 2-1 (10.0 g, 19.43 mmole) in 75 mL DMF was treated with cesium carbonate (3.16 g, 9.72 mmole) with stirring at room temperature for 2.0 hours. Then, methyl iodide (2.76 g, 19.43 mmole) was added dropwise and the reaction mixture was stirred overnight at ambient temperature. The solvent was removed at high vacuum (30 degrees C.) and the residue was taken up in 300 mL EtOAc and washed with 2×40 mL protions of saturated NaHCO$_3$ solution, brine, and dried (Na$_2$SO$_4$). Solvent removal provided 3-1 (8.5 g, 83%) as a clear oil.

$^1$H NMR (300 MHz, CDCl$_3$) δ 1.25–1.53 (16H, m), 1.76 (2H, m), 2.96–3.17 (4H, m), 3.71 (3H, s), 3.90 (2H,t), 4.61 (1H, m). 5.10 (2H, m), 5.19 (1H, m), 6.88 (2H, d), 6.98 (sH, d), 7.32 (5H, m).

EXAMPLE 33

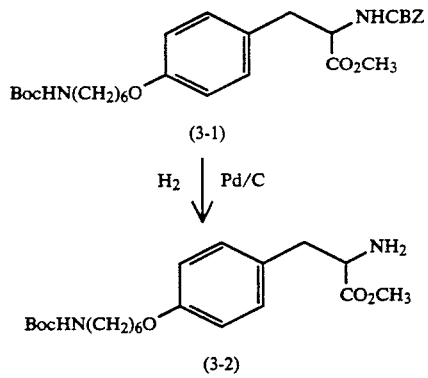

Methyl 2-S-Amino-3-[4-(6-N-t-butyloxycarbonylaminohexyloxy)phenyl]propionate (3-2)

Compound 3-1 (8.0 g, 15.1 mmole) was dissolved in 150 mL absolute ethanol and 1.0 g 10% Pd/C was added. This suspension was hydrogenated in a Parr apparatus (50 psi) for 3.5 hours. The catalyst was then filtered off and the solvent removed on the rotary evaporator to give pure 3-2 (5.56 g) as a clear oil. R$_f$=0.4 on SiO$_2$ with 95:5 CHCl$_3$/CH$_3$OH $^1$H NMR (300 MHz, CDCl$_3$) δ 1.30–1.55 (16H, m), 1.70 (2H, m), 2.80 (1H, m), 3.00–3.17 (3H, m), 3.71 (3H, s), 3.93 (2H, t), 6.82 (2H, d), 7.09 (2H, d).

EXAMPLE 34

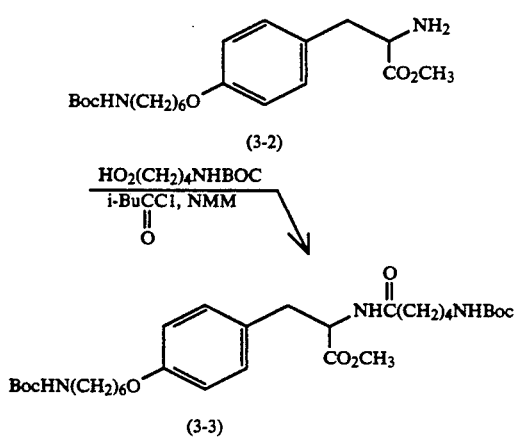

Methyl 2-S-[(5-N-t-Butyloxycarbonylamino)pentanoylamino]-3-[4-(6-N-t-butyloxycarbonylaminohexyloxy)phenyl]-propionate (3-3)

To a solution of 5-(N-t-butyloxycarbonylamino)pentanoic acid (0.293 g, 1.35 mmole) and N-methyl-morpholine (0.187 g, 1.35 mmole) in 10 mL EtOAc at 0°–5° C. was added i-butylchloroformate (0.184 g, 1.35 mmole) via syringe and the resulting white suspension was stirred for 0.5 hours. Then, 3-2 (0.5 g, 1.27 mmole) dissolved in 10 mL EtOAc was added dropwise and the reaction mixture was stirred at 0° C. for 2.0 hours. The reaction mixture was then diluted with 25 mL water/ 40 mL EtOAc and the organic phase was separated, washed with water, 10% KHSO₄, water, saturated NaHCO₃, brine and dried (Na₂SO₄). Solvent removal gave an oil that was purified by flash chromatography on silica gel eluting with 2% CH₃OH/CHCl₃ (R$_f$=0.35) to give pure 3-3 (0.68 g, 90%) as a clear oil.

$^1$H NMR (300 MHz, CDCl₃) δ 1.35–1.55 (26H, m) 1.62 (2H, m), 1.68 (2H, m), 2.20 (2H, t), 3.0–3.16 (6H, m), 3.33 (3H, s), 3.92 (2H, t), 4.83 91H, m), 6.80 (2H, d), 6.99 (2H, m).

EXAMPLE 35

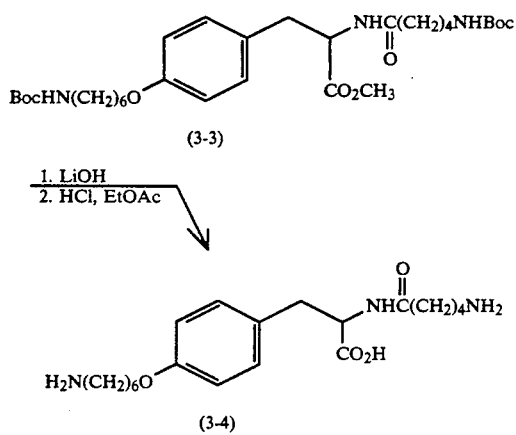

2-S-(5-Aminopentanoyl)amino-3-[4-(6-aminohexyloxy)-phenyl)]propionic acid dihydrochloride (3-4)

3-3 (0.68 g, 1.14 mmole) was dissolved in 30 mL THF(1)/H₂O(1)/CH₃OH(1), LiOH (0.137 g, 5.73 mmole) was added and the reaction mixture stirred at room temperature overnight. The solvent was then removed and the residue was taken up in 75 mL H₂O and acidified to pH 2-3 with 10% KHSO₄ solution. This was extracted with EtOAc and the combined organic extracts were washed with brine and dried (Na₂SO₄). Solvent removal gave 2-S-(5-t-butyloxycarbonylaminopentyl)amino-3-[4-(6-t-butyloxycarbonylaminohexyl)oxyphenyl]-propionic acid (0.65 g).

$^1$H NMR (300 MHz, CDCl₃) δ 1.40–0.155 (22H, m). 1.60 (2H, m), 1.73 (2H, m), 2.20 (2H, m), 3.10 (4H, m), 3.90 (2H, m), 4.60 (1H, m), 4.72 (1H, m), 4.83 (1H, m), 6.78 (2H, d), 7.05 (2H, d).

This acid was dissolved in EtOAc and was treated with HCl gas as described for 2-2. The crude hygroscopic white solid was triturated with a solution of 10 mL EtOAc/50 mL Et₂O to give pure 3-4 as a white solid.

$^1$H NMR (300 MHz, CD₃OD) δ 1.42–1.85 (14H, m), 2.23 (2H, m), 2.90 (6H, m), 3.14 (1H, dd), 3.30 (1H, m), 3.97 (2H, t), 4.60 (1H, m), 6.82 (2H, d), 7.13 (2H, d).

Analysis for C₂₀H₃₃N₃O₄.2HCl.3H₂O Calc.: C=47.43, H=8.16, N=8.30, Found: C=47.87, H=7.49, N=7.90.

EXAMPLE 36

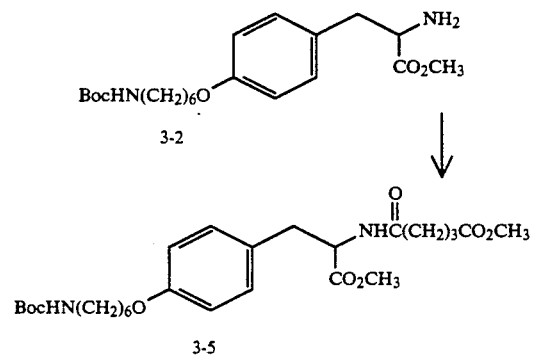

Methyl 2-S-(4-Carbomethoxybutanoyl)amino-3-[4-(N-t-butyloxycarbonylaminohexyloxy)phenyl]propionate (3-5)

To a solution of 3-2 (0.5 g, 1.27 mmole), 4-carbomethoxybutanoic acid (0.213 g, 1.5 mmole) and 1 drop of triethylamine in 20 mL CH₃CN was added BOP reagent (0.66 g, 1.5 mmole) and the resulting clear solution was stirred overnight at room temperature. The solvent was removed on the rotary evaporator and the residue was taken up in EtOAc and this was washed with H₂O, 10% KHSO₄, H₂O, saturated NaHCO₃, brine and dried (Na₂SO₄). Solvent removal provided a residue that was purified by flash chromatography on silica gel eluting with 1% CH₃OH/CHCl₃ to give pure 3-5 (110 mg) as a clear oil.

$^1$H NMR (300 MHz, CDCl₃), δ 1.35–1.55 (14H, m), 1.75 (3H, m), 1.94 (2H, m), 2.26 (2H, t), 2.35 (2H, t), 2.98–3.16 (4H, m), 3.67 (3H, s), 3.73 (3H, s), 3.91 (2H, t), 4.82 (1H, m), 6.80 (2H, d), 6.95 (2H, d).

EXAMPLE 37

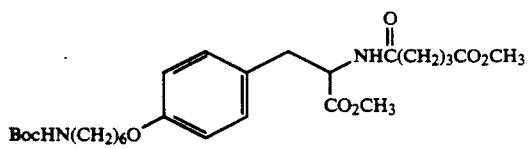

3-5

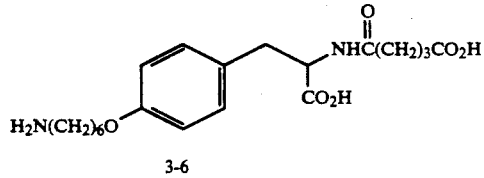

3-6

2-S-(4-Carboxybutanoylamino)-3-[4-(6-aminohexyloxy)phenyl]propionic acid (3-6)

3-5 (0.11 g, 0.21 mmole) was treated with LiOH (0.025 g, 1.05 mmole) as described for compound 3-4 to give the desired diacid (0.105 g).

$^1$H NMR (300 MHz, CD$_3$OD) δ 1.30–1.55 (16H, m) 1.70–1.82 (4H, m), 2.20 (4H, m), 2.85 (1H, m), 3.03 (2H, m), 3.13 (1H, dd), 3.30 (1H, m), 3.92 (2H, m), 4.62 (1H, m), 6.81 (2H, d), 7.12 (2H, d).

This diacid (0.105 g) was dissolved in 30 mL EtOAc and treated with HCl gas as described for compound 2-2. The resulting solid was purified by flash chromatography on silica gel eluting wtih 90:8:8 ethanol/N-H$_4$OH/H$_2$O to provide pure 3-6 as a white solid.

$^1$H NMR (300 MHz, CD$_3$OD) δ 1.42 (2H, m), 1.50 (2H, m), 1.63 (2H, m), 1.76 (4H, m), 2.17 (4H, m), 2.85 (3H, m), 3.16 (1H, m), 4.0 (2H, t), 4.48 (1H, m), 6.78 (2H, d), 7.12 (2H, d).

Analysis for C$_{20}$H$_{30}$N$_2$O$_6$.1.2 H$_2$O: Calc.: C=57.73, H=7.85, N=6.73; Found: C=57.66, H=7.21, N=6.83.

EXAMPLE 38

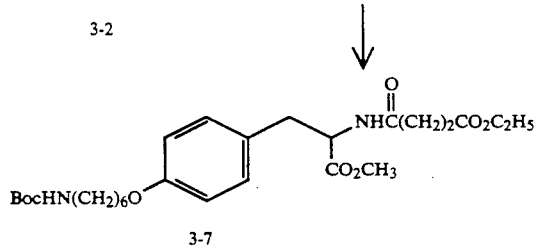

Methyl 2-S-(3-Carboethoxypropanoyl)amino)-3-[4-(6-N-t-butyloxycarbonylaminohexyloxy)phenyl]propionate (3-7)

3-2 (0.562 g, 1.42 mmole) was dissolved in 15 mL EtOAc and treated with NaHCO$_3$ (0.36 g, 4.27 mmole) and 3-carboethoxypropanoyl chloride (0.235 g, 1.42 mmole) with stirring overnight. The reaction mixture was diluted with 150 mL EtOAc and the organic phase was washed with H$_2$O, brine and dried (Na$_2$SO$_4$). Solvent removal gave a residue that was purified by flash chormatography on silica gel eluting with 98:2 CHCl$_3$/CH$_3$OH to give pure 3-7 (0.5 g).

$^1$H NMR (300 MHz, CDCl$_3$) δ 1.26 (3H, t), 1.35–1.61 (16H, m), 1.76 (2H, m), 2.48 (2H, m), 2.63 (2H, m), 3.05 (2H, m), 3.11 (2H, m), 3.72 (3H, s), 3.92 (2H, t), 4.13 (2H, q), 4.82 (2H, m), 6.80 (2H, d), 7.00 (2H, d).

EXAMPLE 39

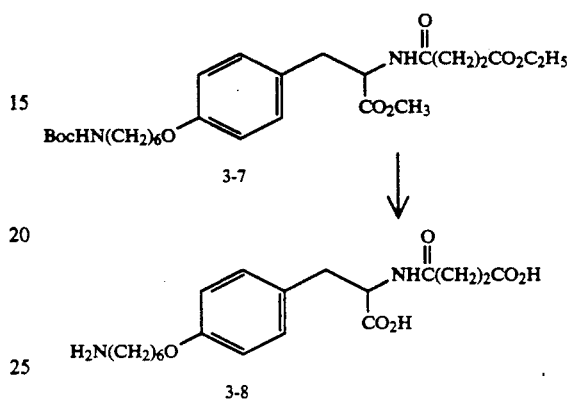

2-S-(3-Carboxypropanoyl)amino-3-[4-(6-aminohexyloxy)phenyl]propionic acid hydrochloride (3-8)

3-7 (0.58 g, 1.11 mmole) was treated with LiOH as described for 3-3 to give 2-S-(carboxypropanoyl)amino-3-[4-(6-N-t-butyloxycarbonylaminohexyloxyphenyl]-propionic acid (0.44 g) as a foam.

$^1$H NMR (300 MHz, CD$_3$OD) δ 1.32–1.58 (16H, m), 1.77 (2H, m), 2.40 (4H, m), 2.89 (1H, m), 3.0–3.16 (3H, m), 3.33 (1H, m), 3.90 (2H, t), 4.42 (1H, m), 6.78 (2H, d), 7.11 (2H, d).

This acid (0.435 g) was treated with HCl gas in EtOAc (30 mL) as described for 2-2 to give a foam that was triturated with EtOAc to give pure 3-8 (0.25 g) as a white solid.

$^1$H NMR (300 MHz, CD$_3$OD) δ 1.4–1.6 (4H, m), 1.76 (2H, m), 2.46 (4H, m), 2.92 (3H, m), 3.14 (1H, m), 3.30 (1H, m), 3.96 (2H, m), 4.60 (1H, m), 6.81 (2H, d), 7.14 (2H, d).

Analysis for C$_{19}$H$_{28}$N$_2$O$_5$.HCl.0.5 H$_2$O: Calc.: C=53.58, H=7.10, N=6.58; Found: C=53.18, H=6.93, N=6.27.

EXAMPLE 40

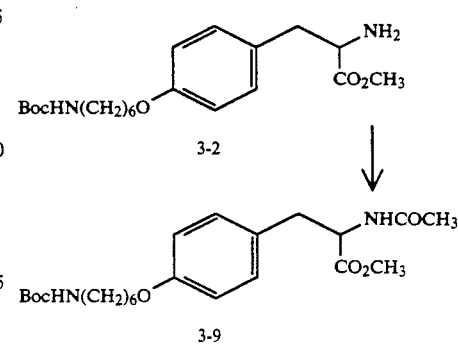

Methyl 2-S-(Acetylamino)-3-[4-(6-N-t-butyloxycarbonylaminohexyloxy)phenyl]propionate (3-9)

3-2 (0.562 g, 1.42 mmole) was treated with acetyl chloride (0.112 g, 4.27 mmole) as described for 3-7 to give a yellow oil. This was purified by flash chromatography on silica gel eluting with 98:2 CHCl3/CH3OH to give pure 3-9 (0.58 g) as a clear oil.

1H NMR (300 MHz, CDCl3) δ 1.30–1.56 (14H, m), 1.78 (2H, m), 2.00 (3H, s), 3.05–3.16 (4H, m), 3.73 (3H, s), 3.92 (2H, t), 4.84 (1H, m), 6.80 (2H, d), 6.98 (2H, d).

EXAMPLE 41

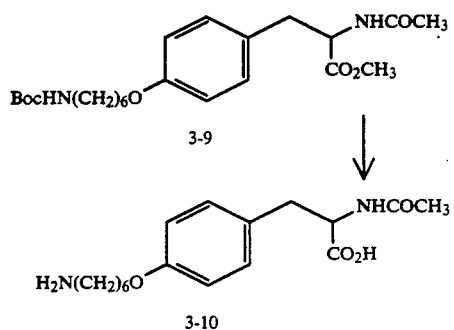

2-S-(Acetylamino)-3-[4-(6-aminohexyloxy)phenyl]propionic acid hydrochloride (3-10)

3-9 (0.58 g, 1.33 mmole) was treated with LiOH (0.16 g, 6.64 mmole) as described for 3—3 to give 2-S(acetylamino)-3-[4-(6-N-t-butyloxycarbonylaminohexyloxy)phenyl]propionic acid (0.485 g) as a white solid.

1H NMR (300 MHz, CD3OD) δ 1.35–1.53 (16H, m), 1.75 (2H, m), 1.90 (3H, s), 2.86 (1H, m) 3.00–3.15 (3H, m), 3.30 (1H, m), 3.93 (2H, t), 4.59 (1H, m), 6.82 (2H, d), 7.12 (2H, d).

This compound (0.485 g) was dissolved in 30 mL EtOAc and treated with HCl gas as described for 2-2 to give a residue that was triturated with EtOAc to provide pure 3-10 (0.4 g) as a white solid.

1H NMR (300 MHz, CD3OD) δ 1.42–1.60 (4H, m), 1.66 (2H, m), 1.70 (2H, m), 1.90 (3H, s), 2.82 (1H, m), 2.92 (2H, m), 3.12 (1H, dd), 3.30 (1H, m), 3.95 (2H, t), 4.60 (1H, m), 6.82 (2H, d), 7.13 (2H, d).

Analysis for C17H26N2O4.HCl.H2O: Calc.: C=54.17, H=7.76, N=7.43; Found: C=54.30, H=7.71, N=7.09.

EXAMPLE 42

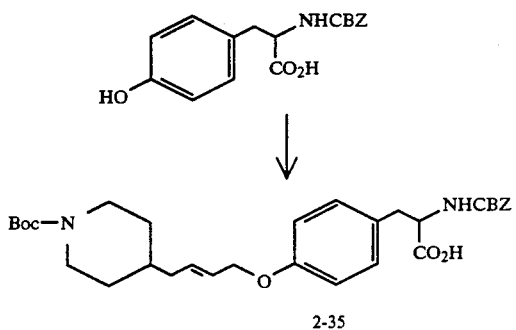

2-S-(N-Benzyloxycarbonylamino)-3-[4-(4-N-t-butyloxycarbonylpiperidin-4-yl)but-2-enyloxyphenyl]propionic acid (2-35)

N-CBZ-L-tyrosine (0.48 g, 0.0014 mmole) was alkylated with (4-N-t-butyloxycarbonylpiperidin-4-yl)but-2-enyl bromide (0.424 g, 1.35 mmole) (prepared from 2-11 by basic hydrolysis (LiOH), reduction with BH3 to give the alcohol, and halogenation with PPh3/CBr4) as described for 2-1. Crude product was purified by flash chromatography on silica gel eluting with 97:3:1 CHCl3/CH3OH/HOAc to give pure 2-35 as an oil.

1H NMR (300 MHz, CDCl3) δ 1.00–1.21 (4H, m), 1.40–1.55 (14H, m), 2.00–2.15 (2H, m), 2.61–2.75 (2H, m), 4.02–4.14 (3H, m), 4.57 (2H, m), 4.63 (1H, m), 5.15 (2H, m), 5.32 (1H, m), 5.58 (1H, m), 5.62–5.70 (2H, m), 6.72 (2H, t), 7.00 (2H, d).

EXAMPLE 43

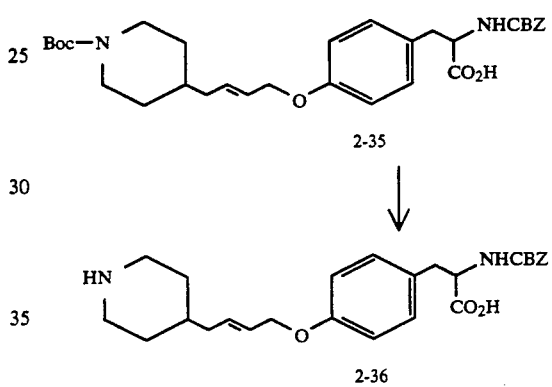

2-S-(N-Benzyloxycarbonylamino)-3-[4-(4-piperidin-4-yl)-but-2-enyloxyphenyl]propionic acid (2-36)

2-35 (0.5 g) was dissolved in 25 mL EtOAc and treated with HCl gas as described for 2-15 to provide a residue that was titurated with ether to give 2-36. A small sample was purified by HPLC to give 2-36 as the trifluoroacetate salt.

1H NMR (300 MHz, D2O) 7.2 (2H, m), 7.1 (4H, m), 6.7 (2H, d), 5.5 (2H, m), 5.1 (1H, d), 4.8 (1H, d), 4.2 (3H, bs), 3.2 (1H, d), 2.8 (3H, m), 2.25 (2H, 6t), 1.8 (2H, m), 1.4 (3H, m), 1.2 (1H, m), 0.9 (2H, m).

Analysis for C26H32N2O5: Calc.: C=57.87, H=5.68, N=4.75; Found: C=57.98, H=5.79, N=4.61.

SCHEME 4

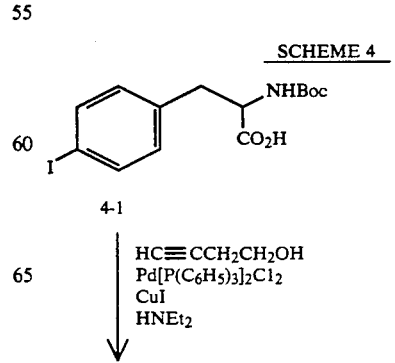

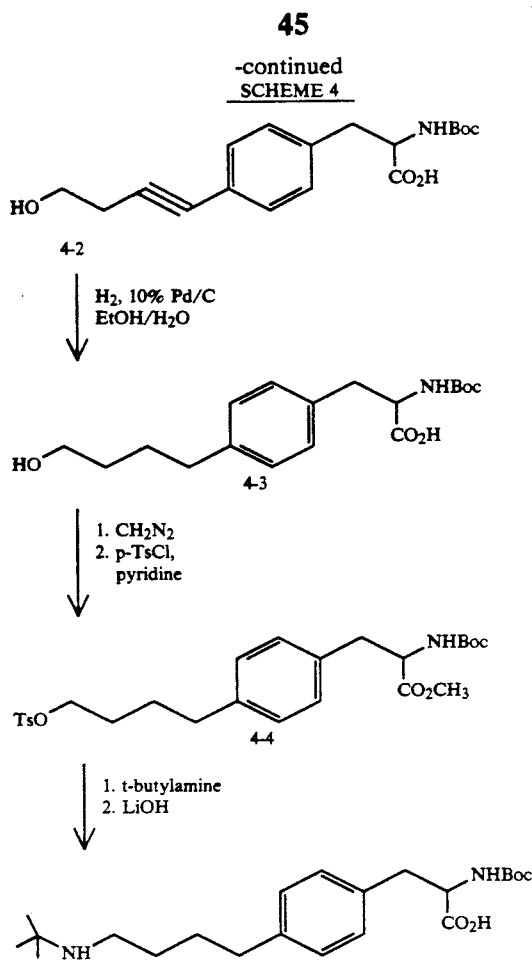

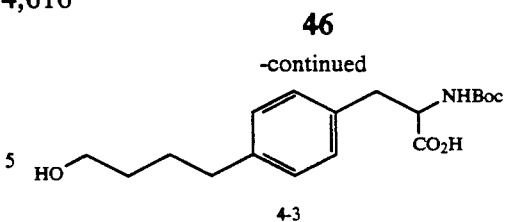

2-S-(N-t-Butyloxycarbonylamino)-3-[4-(4-hydroxybutyl)phenyl]propionic acid (4-3)

4-2 (0.40 g, 1.2 mmole) was dissolved in an ethanol/water solution (25 mL) and was treated with 10% Pd/C (0.1 g) and $H_2$ on a Parr apparatus. After 2 hours the solution was filtered and evaporated. Column chromatography on silica gel (94:5:1 $CHCl_3/CH_3OH/HOAc$) yielded 0.321 g (80%) of 4-3. $R_f$=0.57 in 97:3:1 $CHCl_3/CH_3OH/HOAc$ ninhydrin stain.

$^1H$ NMR (300 MHz, $CDCl_3$) δ 7.1 (s, 4H), 4.95 (1H, m), 4.9 (1H, broad), 4.55 (1H, m), 3.65 (2H, t), 3.1 (2H, m), 1.6 (4H, m), 1.4 (9H, s).

EXAMPLE 48

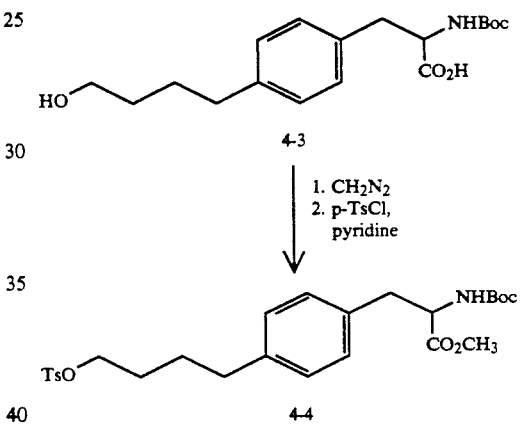

Methyl 2-S-(N-t-Butyloxycarbonylamino)-3-[4-(4-tosyloxybutyl)phenyl]propionate (4-4)

4-3 (0.285 g, 0.85 mmole) was dissolved in $CH_2Cl_2$ (10 mL) cooled to 0° C., and treated with $CH_2N_2$ solution. After 10 minutes the reaction was quenched with $MgSO_4$, filtered and evaporated to provide ester used in the next reaction. $R_f$=0.5 in 92:8:1 $CHCl_3/CH_3OH/HOAc$, ninhydrin stain.

$^1H$ NMR (300 MHz, $CDCl_3$) δ 7.05 (d, J=7.8 Hz, 2H), 7.0 (d, J=7.8 Hz, 2H), 5.0 (1H, m), 4.55 (1H, m), 3.69 (3H, s), 3.6 (2H, J=6.2 Hz, t), 3.0 (2H, m), 2.6 (2H, J=7.5 Hz, t), 1.7 (4H, m), 1.4 (9H, s).

This ester was dissolved in 10 mL $CH_2Cl_2$ and added at −78° C. to a solution prepared from treating p-toluenesulfonyl chloride (0.14 g, 0.67 mmole) in $CH_2Cl_2$ at −78° C. with pyridine (0.1 ml, 1.35 mmole) for 10 minutes. The reaction was allowed to warm to room temperature over 1.0 hour and then water was added. The organic layer was separated, dried, and evaporated. Column chromatography 97:3:1 on silica gel eluting with $CHCl_3/CH_3OH/HOAc$ gave 4-4 (0.27 g, 70%). $R_f$=0.85 97:3:1 $CHCl_3/CH_3OH/HOAc$.

$^1H$ NMR (300 MHz, $CDCl_3$) δ 7.88 (2H, J=7.2 Hz, d), 7.74 (2H, J=7.2 Hz, d), 7.38 (2H, J=Hz, d), 7.30 (2H, J=8 Hz, d), 5.0 (1H, m), 4.5 (1H, m), 4.0 (2H,

2-S-(N-t-Butyloxycarbonylamino)-3-[4-(4-hydroxybut-1-ynyl)phenyl]propionic acid (4-2)

N-BOC-4-iodo-L-phenylalanine (4-1) (1.0 g, 2.55 mmole) was dissolved in diethylamine under $N_2$ and treated with 3-butyne-1-ol (0.23 mL, 3.06 mmole), $[Pd(P(C_6H_5)_3]_2Cl_2$ (0.089 g, 0.127 mmole) and CuI (0.012 g, 0.064 mmole). After 3 hours the solvent was evaporated, the residue dissolved in water (pH=11) and extracted with ethyl acetate. The water layer was then acidified to pH 3, extracted with ethyl acetate. This organic extract was dried and evaporated to give 0.8 g crude 4-2. $R_f$=0.47 in 97/3/1 $CHCl_3/CH_3OH/HOAc$, ninhydrin stain.

$^1H$ NMR (300 MHz, $CDCl_3$) δ 7.35 (2H, d), 7.1 (2H, d), 6.4 (1H, broad) 5.0 (1H, d), 4.6 (1H, m), 3.8 (2H, t), 3.1 (2H, m), 2.65 (2H, t), 1.4 (9H, s).

EXAMPLE 47

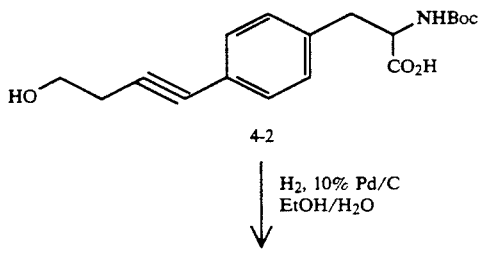

J=5.3 Hz, t), 3.67 (3H, s), 3.0 (2H, m), 2.5 (2H, t), 2.0 (3H, s), 1.6 (4H, m), 1.4 (9H, s).

EXAMPLE 49

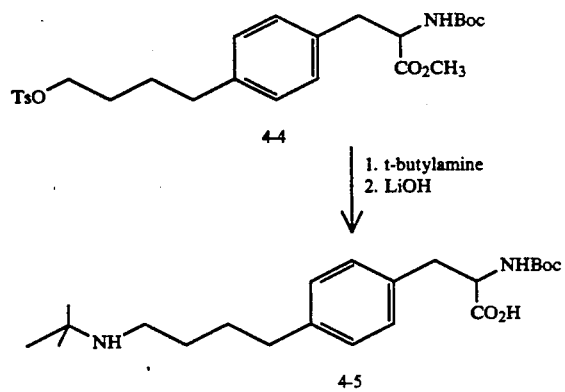

2-S-(N-t-Butyloxycarbonylamino)-3-[4-(4-t-butylaminobutyl)phenyl]propionic acid (4-5)

4-4 (0.26 g, 0.48 mmoles) was dissolved in t-butylamine (5 mL) and this solution was refluxed for 2 days. The reaction was filtered and the excess t-butylamine removed at high vacuum (30° C.). The residue was purified by flash chromatography on silica gel eluting with 98:2 CHCl₃ (saturated with NH₃)/CH₃OH to give methyl 2-S-(N-t-butyloxycarbonylamino)-3-[4-(4-t-butylaminobutyl)phenyl]propionate (0.11 g, 52%) as an oil.

¹H NMR (300 MHz, CDCl₃) δ 7.05 (2H, d), 7.0 (2H, d), 4.95 (1H, d), 4.55 (1H, m), 3.7 (3H, s), 3.0 (2H, m), 2.55 (2H, d).

This ester (0.10 g, 2.7 mmole) was dissolved in 1:1:1 THF/CH₃OH/H₂O (10 mL) and LiOH.H₂O (0.033 g, 1.38 mmole) was added at room temperature. After stirring for 2 hours the solvent was removed and the residue chromatographed on silica gel eluting with 9:1:1 C₂H₅OH/H₂O/NH₄OH to give pure 4-5.

¹H NMR (300 MHz, D₂O) δ 7.35 (4H, s), 4.25 (1H, dd), 3.2 (1H, m), 3.1 (2H, t), 2.9 (1H, m), 2.8 (2H, t), 1.8 (4H, m), 1.4 (18H, s).

Analysis for C₂₂H₃₆N₂O₄.1.0 CF₃CO₂H: Calc.: C=56.90, H=7.36, N=5.53; Found: C=56.73, H=7.51, N=5.58.

SCHEME 5

-continued
SCHEME 5

EXAMPLE 50

2-S-Amino-3-[4-(4-N-t-butyloxycarbonylpiperidin-4-yl)butyloxyphenyl]propionic acid (5-1)

2-13 (2.0 g) was dissolved in 100 mL EtOH, and 0.2 g 10% Pd-C was charged. This suspension was hydrogenated at balloon pressure overnight. Solvent removal provided 5-1 (1.36 g) as a white solid.

¹H NMR (300 MHz, CD₃OD), δ 0.97–1.12 (2H, m), 1.20–1.54 (14H, m), 1.72 (4H, m), 2.71 (2H, m), 2.90–3.00 (1H, m), 3.22 (1H, dd), 3.30 (1H, m), 3.71 (1H, m), 3.95–4.10 (4H, m), 6.88 (2H, d), 7.21 (2H, d).

EXAMPLE 51

-continued

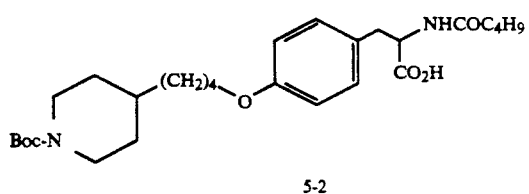

5-2

2-S-(Pentanoylamino)-3-[4-(4-N-t-butyloxycarbonyl-piperidin-4-yl)butyloxyphenyl]propionic acid (5-2)

5-1 (1.05 g, 2.5 mmole) was added to a cold solution of 1N NaOH (2.5 mL) in 20 mL H₂O and stirred at 0–10 degrees C. for 5 minutes to give a clear solution. Then, pentanoyl chloride (0.332 g, 2.75 mmole) was added dropwise followed by NaHCO₃ (0.231 g, 2.75 mmole) and the resulting mixture was stirred vigorously at 0°–10° C. for 1 hour. The reaction mixture was diluted with H₂O (75 mL), acidified to pH 2-3 with 10% KHSO₄ and extracted with EtOAc. This extract was filtered, washed with brine, dried (Na₂SO₄) and the solvent removed to give an oil. This was purified by flash chromatography on silica gel eluting with 97:3:1 CHCl₃/CH₃OH/HOAc to give pure 5-2 (0.44 g) as a clear oil.

¹H NMR (300 MHz, CD₃OD) δ 0.90 (3H, t), 1.20–1.62 (16H, m), 1.72 (2H, m), 2.14 (2H, m), 2.30 (8H, m), 2.65–2.90 (4H, m), 3.30 (1H, m), 3.93 (2H, m), 4.61 (1H, m), 6.81 (2H, d), 7.12 (2H, d).

EXAMPLE 52

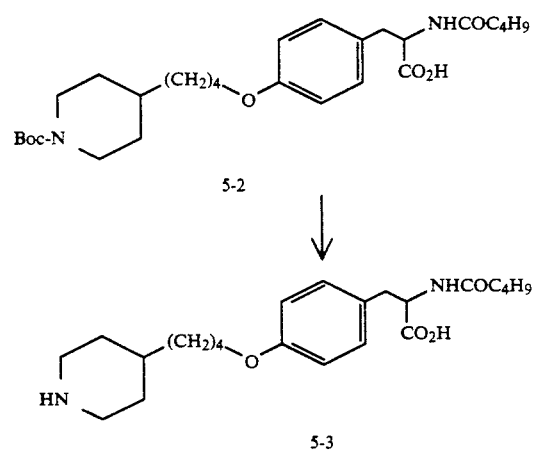

2-S-(Pentanoylamino)-3-[4-(4-piperidin-4-ylbutyloxy)-phenyl]propionic acid hydrochloride (5-3)

5-2 (0.449 g), was dissolved in 30 mL EtOAc and treated with HCl gas at −10° C. as described for 2-2. The resulting solid was triturated with 40 mL Et₂O to give pure 5-3 (0.36 g) as a white solid.

¹H NMR (300 MHz, CD₃OD) δ 0.85 (3H, t), 1.19 (2H, m), 1.30–1.65 (9H, m), 1.73 (2H, m), 1.95 (2H, m), 2.15 (2H, m), 2.80–3.02 (3H, m), 3.14 (1H, dd), 3.30–3.40 (3H, m), 3.95 (2H, t), 4.61 (1H, m), 6.82 (2H, d), 7.13 (2H, d).

Analysis for C₂₃H₃₆N₂O₄·HCl·0.75 H₂O: Calc.: C=60.77, H=8.54, N=6.16; Found: C=60.97, H=8.39, N=6.06.

EXAMPLE 53

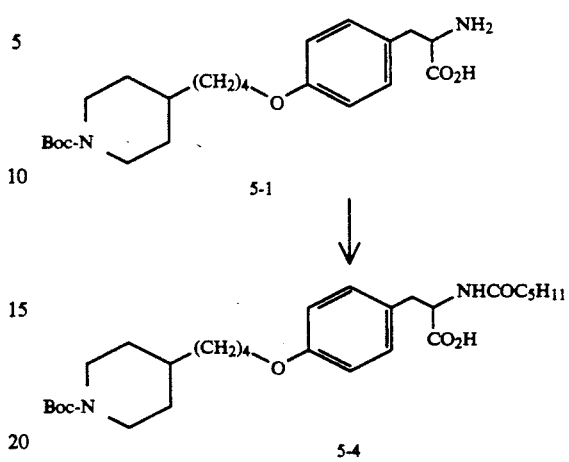

2-S-(Hexanoylamino)-3-[4-(4-N-t-butyloxycarbonyl-piperidin-4-yl)butyloxyphenyl]propionic acid (5-4)

5-1 (0.41 g) was treated with hexanoyl chloride (0.21 mL, 1.50 mmole) as described for 5-2. Crude product was purified by flash chromatography on silica gel eluting with 97:3:1 CHCl₃/CH₃OH/HOAc to give pure 5-4 (0.20 g).

¹H NMR (300 MHz, CD₃OD) δ 0.85 (3H, t), 0.97–1.35 (8H, M), 1.37–1.53 (12H, m), 1.60–1.80 (4H, m), 2.13 (2H, t), 2.80 (2H, m), 2.85 (1H, m), 3.12 (1H, dd) 3.90 (2H, t), 4.04 (2H, d), 4.62 (1H, m), 6.80 (2H, d), 7.12 (2H, d).

EXAMPLE 54

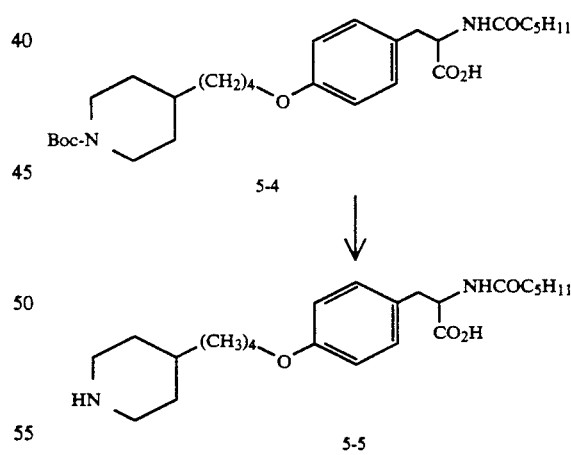

2-S-(Hexanoylamino)-3-[4-(4-piperidin-4-ylbutyloxy)-phenyl]propionic acid (5-5)

5-4 (0.199 g) was dissolved in 25 mL EtOAc and treated with HCl gas as described for compound 2-2 to provide pure 5-5 (48 mg).

¹H NMR (300 MHz, CD₃OD) δ 0.84 (3H, t), 1.08–1.20 (4H, m), 1.35 (4H, m), 1.52 (4H, m), 1.77 (2H, m), 1.92 (2H, d), 2.16 (2H, t), 2.80–3.-2 (3H, m), 3.15 (1H, dd), 3.40–3.52 (2H, m), 3.92 (2H, t), 4.61 (1H, m), 6.81 (2H, d), 7.13 (2H, d).

Analysis for $C_{26}H_{39}N_2O_6F_3 \cdot 0.55\ H_2O \cdot 0.30$ TFA: Calc.: C=55.39, H=7.06, N=4.86; Found: C=55.38, H=7.03, N=4.85.

SCHEME 6

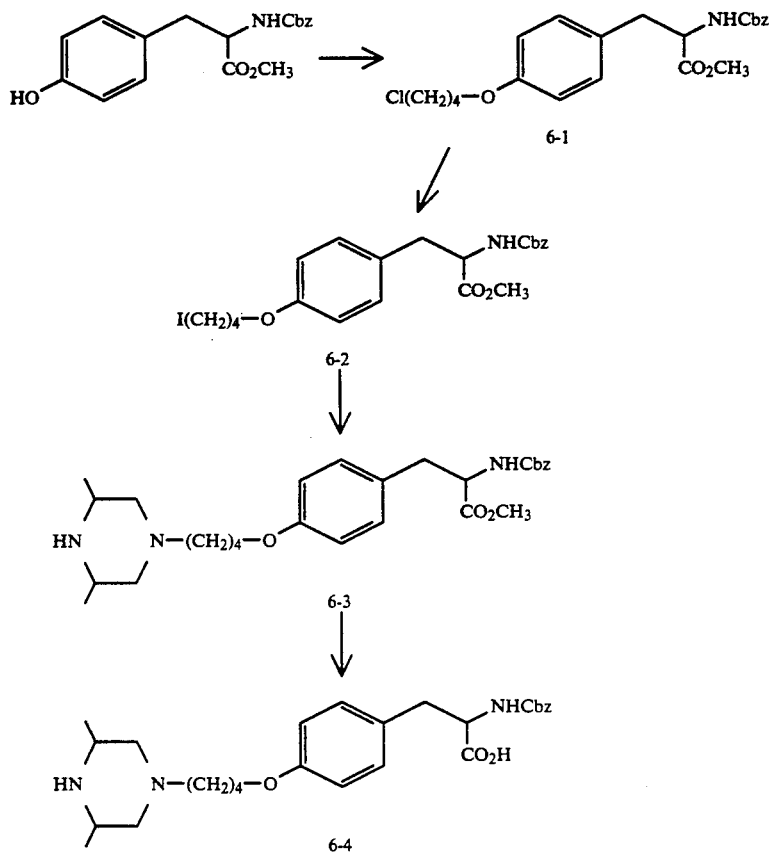

EXAMPLE 55

Methyl 2-S-(N-Benzyloxycarbonylamino)-3-[4-(4-chlorobutyloxyphenyl)]propionate (6-1).

Treatment of a DMF solution of N-CBZ-tyrosine (0.95 g, 2.9 mmol) and 4-chloro-1-tosyloxybutane (0.84 g, 3.19 mmol) with cesium carbonate (0.47 g, 1.45 mmole) gave a solution that was stirred at room temperature overnight. The reaction mixture was then diluted with $H_2O$ and extracted with ether. The ether extract was washed with brine, dried ($Na_2SO_4$) and the solvent removed to give an oily residue. This was purified by flash chromatography on silica gel eluting with EtOAc(5)-hexane(95) to afford 6-1 as a clear oil. $R_f 0.5$ (silica gel eluting with EtOAc(30)-hexane(70).

EXAMPLE 56

Methyl 2-S-(N-Benzyloxycarbonylamino)-3-[4-(4-iodobutyloxyphenyl)]propionate (6-2).

A solution of 6-1 (0.6 g, 1.5 mmol) in acetone was treated with sodium iodide (1.1 g, 7.5 mmol) and the resulting solution was heated at reflux for 16 hours. The reaction mixture was then diluted with ether, washed with water, brine and dried ($Na_2SO_4$). Solvent removal gave an oil that was purified by flash chromatography on silica gel eluting with hexane(90)-EtOAc(10) to give 6-2 as a clear oil.

$^1$H NMR (300 MHz, CDCl$_3$) δ 1.85–2.08 (4H, m), 3.04 (2H, m), 3.26 (2H, t), 3.71 (3H, s), 3.95 (2H, t), 4.60 (1H, m), 5.00–5.21 (3H, m), 6.78 (2H, d), 6.99 (2H, d), 7.33 (5H, m).

EXAMPLE 57

Methyl 2-S-(N-Benyzloxycarbonylamino)-3-[4-(2,6-di-methyl-piperazin-4-yl)butyloxyphenyl]propionate (6-3).

A solution of 6-2 (0.1 g, 0.2 mmol) and 2,6-dimethylpiperazine (0.068 g, 0.6 mmol) in 1 ml THF was stirred at room temperature for 20 hours. The solvents were removed at low pressure to provide 6-3 as a clear oil.

$^1$H NMR (300 MHz, CDCl$_3$) δ 1.45 (4H, d), 1.82 (3H, m), 2.65 (2H, m), 2.79 (2H, m), 3.05 (1H, m), 3.18 (2H, bd), 3.60 (1H, m), 3.72 (3H, s), 3.96 (2H, m), 4.62 (1H, m), 5.10 (2H, s), 5.21 (1H, m), 6.79 (2H, d), 7.00 (2H, d), 7.35 (5H, bs).

EXAMPLE 58

2-(N-Benzyloxycarbonylamino)-3-[4-(2,6-dimethylpiperazin-4-yl)butyloxyphenyl]propionic acid (6-4).

6-3 (0.090 g, 0.2 mmol) in methanol was treated with 1N NaOH (0.7 ml) at room temperature for 16 hours. The solvent was removed to give crude acid which was purified by flash chromatography on silica gel eluting with isopropanol(10)-NH$_4$OH(1)-H$_2$O(1) to provide pure 6-4, $R_f 0.25$.

¹H NMR (300 MHz, CD₃OD) δ 1.65-1.85 (4H, m), 2.60-2.70 (2H, m), 2.80-2.95 (6H, m), 3.11 (8H, m), 3.52 (2H, m), 3.65-3.75 (2H, m), 3.82 (2H, t), 4.17 (1H, m), 4.70 (2H, s), 4.85 (2H, m), 6.63 (2H, d), 6.92 (2H, d), 7.10 (5H, bs).

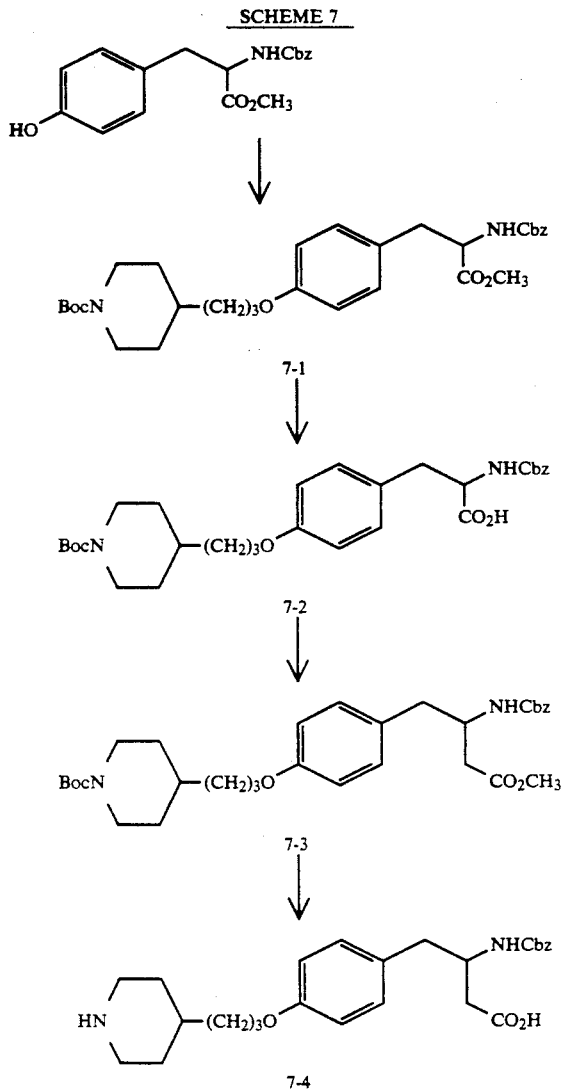

SCHEME 7

EXAMPLE 59

Methyl 2-S-(N-Benzyloxycarbonylamino)-3-[4-(N-t-butyloxycarbonylpiperidin-4-yl)propyloxyphenyl]propionate (7-1)

A solution of N-CBZ-tyrosine (4.0 g, 2.6 mmol) and 3-(N-Boc-piperidin-4-yl)propyl iodide (1.1 g, 3.3 mmol) in 40 ml DMF was treated with cesium carbonate (0.4 g, 1.35 mmol) and the resulting solution was stirred at room temperature for 20 hours. The solvent was removed and the residue was taken up in EtOAc, washed with water, brine and dried (Na₂SO₄). Solvent removal provided a residue that was purified by flash chromatography on silica gel eluting with 4:1 hexane (80)-EtOAc(20) to give pure 7-1 as a clear oil.

¹H NMR (300 MHz, CDCl₃) δ 1.10 (2H, m), 1.37-1.45 (11H, m), 1.65-1.82 (4H, m), 2.68 (2H, m), 3.03 (2H, m), 3.71 (3H, s), 3.90 (2H, t), 4.08 (2H, bd), 4.61 (1H, m), 5.10 (1H, s), 5.18 (1H, m), 6.79 (2H, d), 7.00 (2H, d), 7.35 (5H, bs).

EXAMPLE 60

2-(S)-(N-Benzyloxycarbonylamino)-3-[4-(N-t-butyloxycarbonylpiperidin-4-yl)propyloxyphenyl]propionic acid (7-2)

7-1 (0.5 g, 0.9 mmol) in methanol (12 ml) was treated with 1N NaOH (3 ml) at room temperature for 16 hours. The solvent was then removed and the residue acidified with 5% KHSO₄ solution. This was extracted with EtOAc several times and the combined organic extracts were washed with brine and dried (Na₂SO₄). Solvent removal gave 7-2 as a clear oil.

¹H NMR (300 MHz, CDCl₃) δ 1.10 (2H, m), 1.37-1.52 (12H, m), 1.62-1.85 (5H, m), 2.66 (2H, t), 3.10 (2H, m), 4.89 (2H, t), 4.10 (4H, m), 4.62 (1H, m), 5.09 (1H, s), 5.19 (1H, m), 6.79 (2H, d) 7.03 (2H, d), 7.34 (5H, bs).

EXAMPLE 61

Methyl 3-S-(N-Benzyoxycarbonylamino)-4-[4-(N-t-butyloxycarbonylpiperidin-4-yl)propyloxyphenyl]butanoate (7-3)

To a stirred solution of 7-2 (1.6 g, 2.9 mmol) in EtOAc at −15° C. was added isobutylchloroformate (2.9 mmol) and N-methylmorpholine (2.9 mmol) and the resulting solution was stirred for 0.5 hours at −15°. Then, diazomethane (5.0 mmol in Et₂O) was added and the reaction mixture was stirred at 0° for 20 minutes. The reaction mixture was purged with argon, diluted with EtOAc and washed with water. The organic phase was dried (MgSO₄) and the solvent removed to provide the desired diazoketone.

¹H NMR (300 MHz, CDCl₃) δ 1.10 (2H, m), 1.35-1.50 (12H, m), 1.55-1.85 (6H, m), 2.68 (2H, bt), 2.95 (2H, d), 3.90 (2H, t), 4.09 (3H, m), 4.42 (1H, m), 5.06 (1H, m), 5.20 (1H, m), 5.35 (1H, m), 6.80 (2H, d), 7.06 (2H, d), 7.35 (5H, bs).

This diazoketone (1.63 g, 2.9 mmol) was dissolved in CH₃OH (20 ml) and treated at room temperature with a CH₃OH solution (5 ml) of silver benzoate (0.22 mg, 0.96 mmoles) and triethylamine (1.25 ml). After a few minutes the reaction became black with gas evolution apparent. After 0.5 hours the solvent was removed and the residue was purified by flash chromatography on silica gel eluting with 4:1 hexane(80) EtOAc(20) to give 7-3 as an oil.

¹H NMR (300 MHz, CDCl₃) δ 1.12 (2H, m), 1.37-1.47 (12H, m), 1.60 (2H, s), 1.65-1.83 (4H, m), 2.49 (2H, m), 2.62-2.91 (4H, m), 3.67 (3H, s), 3.90 (2H, t), 4.03-4.20 (4H, m), 5.08 (2H, s), 5.24 (1H, m), 6.79 (2H, d), 7.05 (2H, d), 7.32 (5H, bs).

EXAMPLE 62

3-S-(N-Benzyloxycarbonylamino)-4-[4-(piperidin-4-yl)propyloxyphenyl]butanoic acid (7-4).

A solution of 7-3 (0.3 g, 0.53 mol) was treated with 1N NaOH (1.7 ml) and the resulting mixture was stirred at room temperature for 16 hours. The solvent was removed and the residue acidified with 5% aq KHSO₄ solvent and this was extracted several times with EtOAc. The combined organics were washed with brine, dried (NaSO₄) and the solvent removed to give the desired acid.

$^1$H NMR (300 MHz, CD$_3$OD) δ 1.10 (2H, m), 1.40-1.52 (12, m), 1.65-1.84 (6H, m), 2.54-2.93 (8H, m), 3.92 (2H, t), 4.05-4.12 (3H, m), 5.10 (2H, s), 6.71 (2H, d), 7.08 (2H, d), 7.35 (5H, m).

This acid was dissolved in CH$_2$Cl$_2$ (4 ml) and anisole (0.41 mmole) was added, followed at 0° with trifluoroacetic acid (2 ml). After 2.5 hours stirring at 0°, the solvents were removed and the residue purified by flash chromatography on silica gel eluting with EtOH(10)-NH$_4$OH(1)-H$_2$O(1) to give pure 7-4 as a white solid.

$^1$H NMR (300 MHz, CD$_3$OD) δ 1.3-1.5 (4H, m), 1.6 (1H, m), 1.75-1.85 (2H, m), 1.95 (2H, d), 2.54 (2H, m), 2.72 (2H, m), 2.93 (2H, t), 3.32 (6H, m), 3.92 (2H, t), 4.11 (1H, m), 4.95 (2H, m), 6.75 (2H, d), 7.05 (2H, d), 7.25 (5H, m).

Methyl 2-S-(Hexanoylamino)-3-(4-iodophenyl)propionate (8-2)

A suspension of 8-1 (1.01 g, 2.96 mmoles) in 20 ml CHCl$_2$ was cooled to 0° and pyridine (1.43 ml, 17.7 mmoles) was added followed by hexanoylchloride (1.25 ml, 8.88 mmoles). After 20 minutes all 8-1 was consumed. Water (25 ml) was then added carefully and this mixture was extracted with EtOAc (150 ml). The separated organic phase was washed with 10% KHSO$_4$, brine, dried (Na$_2$SO$_4$) and the solvent was removed to give a white solid. This was purified by flash chromatography on silica gel eluting with 5% Et$_2$O/CHCl$_3$ to give pure 8-2 (1.07 g) as a white solid.

$^1$H NMR (300 MHz, CDCl$_3$) δ 0.88 (3H, t), 1.27 (4H,

SCHEME 8

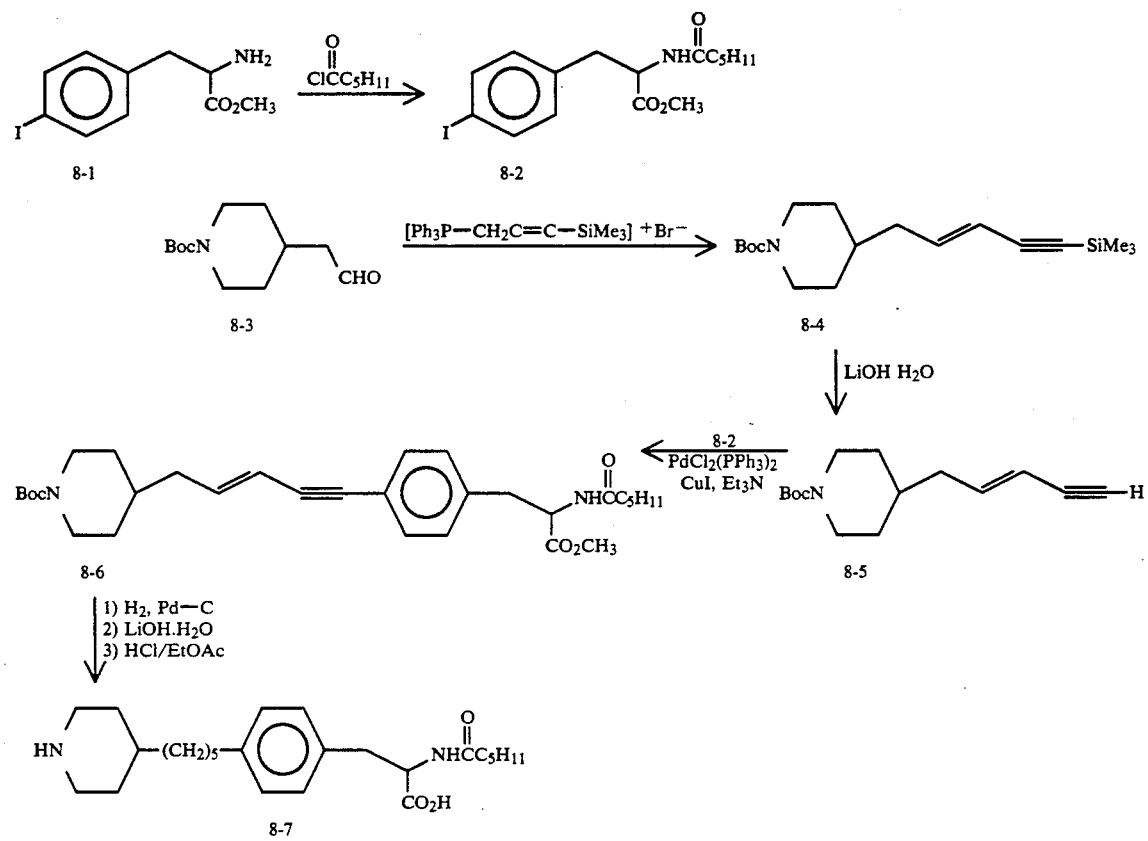

EXAMPLE 63

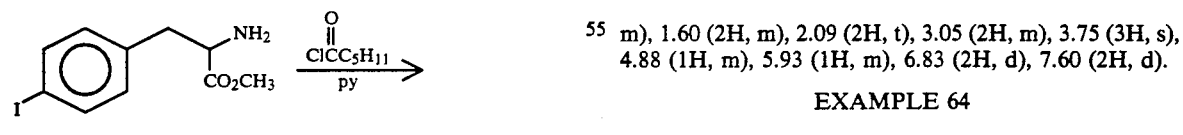

m), 1.60 (2H, m), 2.09 (2H, t), 3.05 (2H, m), 3.75 (3H, s), 4.88 (1H, m), 5.93 (1H, m), 6.83 (2H, d), 7.60 (2H, d).

EXAMPLE 64

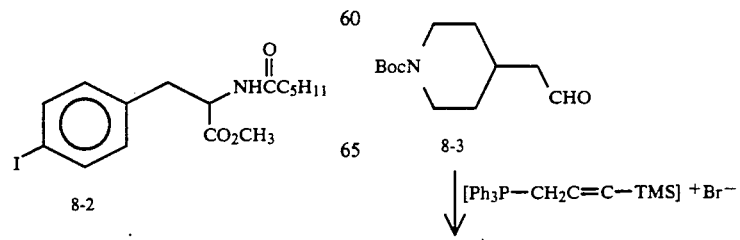

-continued

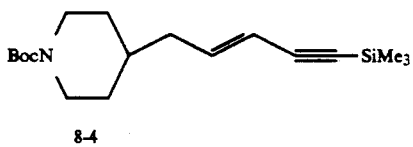

5-(N-t-Butyloxycarbonylpiperidin-4-yl)-1-trimethyl-1-silylpent-3-ene-1-yne (8-4).

A suspension of 3-trimethylsilyl-2-propynyl)triphenyl phosphonium bromide (3.0 g, 6.62 mmoles) (Aldrich) in 50 ml THF was cooled to −78° and treated with n-BuLi (6.62 mmoles) dropwise. The resulting solution was allowed to warm to −40° and was then stirred for 0.5 hours to give a deep red solution. After cooling to −78° C. the reaction mixture was treated with 8-3 (1.07 g, 4,73 mmoles) in 15 ml THF and was allowed to warm to 0° with stirring for 1 hour. The reaction was quenched with 50 ml H2O and this was extracted with EtOAc (200 ml). The organic phase was separated, dried (Na2SO4) and stripped to provide as residue that was purified by flash chromatography on silica gel eluting with 10% EtOAc/hexane to provide pure 8-4, (2.02 g), R$_f$=0.3.

$^1$H NMR (300 MHz, CDCl$_3$) δ 0.10 (9H, s), 0.70-1.10 (4H, m), 1.10-1.40 (13H, m), 1.40-1.60 (3H, m), 1.83 38H, m), 2.40-2.60 (3H, m), 3.85 (3H, m), 5.35 (1H, t), 6.00 (1H, m).

EXAMPLE 65

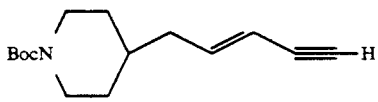

5-(N-t-Butyloxycarbonylpiperidin-4-yl)pent-3-en-1-yne (8-5)

A solution of 8-4 (0.815 g, 2.54 mmoles) in 60 ml THF was treated with 12 ml H$_2$O and lithium hydroxide hydrate (0.96 g, 2.28 mmoles). The reaction mixture was stirred at room temperature for 6 hours during which time the color became dark orange. The reaction mixture was then diluted with Et$_2$O (75 ml) and the aqueous phase was separated and washed with 3×75 ml Et$_2$O. The combined organic extacts were washed with brine, dried and stripped. The resulting residue was purified by flash chromatography on silica gel eluting with 10% EtOAc/hexanes to give 0.63 g pure 8-5.

$^1$H NMR (300 MHz, CDCl$_3$) δ 1.0-1.25 (3H, m), 1.25-1.60 (11H, m), 1.60-1.75 (3H, m), 2.06 (2H, t), 2.30 (1H, t), 2.60-2.78 (2H, m), 4.07 (2H, m), 5.51 (1H, m), 6.22 (1H, m).

EXAMPLE 66

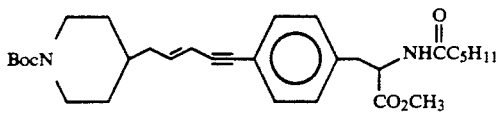

Methyl 2-S-(Hexanoylamino)-3-[4-(5-N-t-butyloxycarbonyl-piperidin-4-yl)pent-3-ene-1-ynephenyl]propionate (8-6).

A solution of 8-5 (0.3 g, 1.2 mmoles) and 8-2 (0.58 g, 1.4 mmoles) in diethylamine (6 ml) was purged with N$_2$ and bis-triphenylphosphine palladium chloride (0.049 g, 0.07 mmoles) was added followed by cuprous iodide (7 mg, 0.035 mmoles) and the suspension was purged again. After several minutes the reaction mixture became homogeneous and this solution was stirred for 16 hours at room temperature.

The solvent was removed at high vacuum and the residue was dissolved in pH 7 buffer and extracted with Et$_2$O. The organic extract was washed with 10% KHSO$_4$, brine, then dried (Na$_2$SO$_4$) and stripped. The residue was purified by flash chromatography on silica gel eluting with 20% EtOAc/hexanes to give 0.28 g pure 8-6. R$_f$=0.3 (20% EtOAc, hexanes).

$^1$H NMR (300 MHz, CDCl$_3$) δ 0.90 (3H, m), 1.05-1.40 (9H, m), 1.52 (6H, s), 1.58-1.75 (4H, m), 2.07 (2H, m), 1.70 (2H, m), 3.14 (2H, m), 3.75 (2H, m), 4.10 (2H, m), 4.89 (1H, m), 5.70 (1H, m), 5.94 (1H, m), 6.18 (1H, m), 7.03 (2H, m), 7.38 (2H, m).

EXAMPLE 67

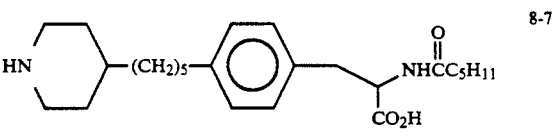

2-S-(Hexanoylamino)-3-[4-(5-Piperidin-4-yl)pentyl-phenyl]propionic acid (8-7)

8-6 (0.275 g, 0.52 mmoles) was dissolved in EtOH and 2 ml of H$_2$O was added along with 5 drops of HOAc. Pd-C (100 mg) was added and the resulting suspension was hydrogenated on a Paar shaker (50 psi) for 4 hours. The reaction mixture was filtered through Solka-Floc and the resulting solvent was removed. The resulting residue was purified by flash chromatography on silica gel eluting with 35% EtOAc/hexanes to give 0.22 g of methyl 2-S-hexanoyl amino-3-[4-5-N-t-butyloxycarbonylpiperidin-4-yl)pentylphenyl propionate.

$^1$H NMR (300 MHz, CDCl$_3$) δ 0.85 (3H, t), 1.00-1.35 (12H, m), 1.45 (9H, s), 1.50-1.65 (6H, m), 2.15 (2H, t), 2.50-2.65 (4H, m), 3.05 (2H, m), 3.71 (3H, s), 4.04 (2H, m), 4.83 (1H, m), 5.96 (1H, m), 6.98 (2H, d), 7.04 (2H, d).

This ester (0.17 g, 0.32 mmoles) was suspended in 10 ml of 1:1 THF/H$_2$O and CH$_3$OH (2 ml), lithium hydroxide hydrate (0.067 g, 1.6 mmoles) was added and the reaction was stirred for 2.0 hours at room temperature. The solvent was then removed and the residue was taken up in H$_2$O. This was acidified to pH 2-3 with 10% KHSO$_4$, and extracted with EtOAc. The organic extract was washed with brine, dried (Na$_2$SO$_4$) and stripped to give 0.050 g of the desired acid.

$^1$H NMR (300 MHz, CDCl$_3$) δ 0.85 (3H, m), 0.95-1.42 (15H, m), 1.47 (9H, s), 1.50-1.70 (7H, m), 2.18 (2H, m), 2.48-2.72 (5H, m), 5.02-5.30 (2H, m), 4.03 (2H, m), 4.84 (1H, m), 6.05 (1H, m), 7.06 (4H, s).

This acid (0.15 g, 0.29 mmoles) was dissolved in EtOAc (25 ml), cooled to −70° and treated with HCl gas for 10 minutes. The temperature was allowed to rise to −20° over 0.5 hr. The reaction mixture was purged with N$_2$ and the solvent was removed. The residue purified by flash chromatography on silica gel eluting with 9:1:1 EtOH/H₂O/NH₄OH to give pure 8-7, 0.040 g as a white solid.

¹H NMR (300 MHz, CD₃OD) δ 0.78 (3H, t), 1.05–1.30 (9H, m), 1.32–1.56 (4H, m), 1.74 (2H, d), 2.03 (2H, m), 2.42 (2H, m), 2.70–2.85 (3H, m), 3.04 (1H, dd), 3.21 (2H, m), 4.38 (1H, m), 6.92 (2H, d), 7.00 (2H, d).

In the above Schemes and Examples, various reagent symbols have the following meanings:

BOC: t-butoxycarbonyl.
Pd-C: Palladium on activated carbon catalyst.
DMF: Dimethylformamide.
CBZ: Benzyloxycarbonyl.
BOP: Benzotriazol-1-yloxytris(dimethylamino)phosphonium hexafluorophosphate.
EtOAc: ethyl acetate
DMF: dimethylformamide
CH₂Cl₂: methylene chloride
CHCl₃: chloroform
MeOH: methanol
HOAc: acetic acid Sample alternative protecting groups that can be used in the preparation of the present invention include benzyl ester, cyclohexyl ester, 4-nitrobenzyl ester, t-butyl ester, 4-pyridylmethyl ester, benzyloxycarbonyl, isonicotinyloxycarbonyl, O-chlorobenzyloxycarbonyl, p-nitrobenzyloxycarbonyl, p-methoxybenzyloxycarbonyl, t-butoxycarbonyl, t-amyloxycarbonyl, isobornyloxycarbonyl, adamantyloxycarbonyl, 2-(4-biphenyl)-2-propyloxycarbonyl and 9-fluorenylmethoxycarbonyl.

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

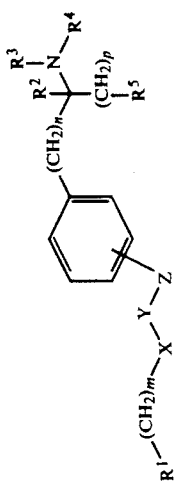
| Example | R¹ | R² | R³ | R⁴ | R⁵ | X | Y | Z | m | n | p |
|---|---|---|---|---|---|---|---|---|---|---|---|
| 55 | ![piperidine] | H | H | —CH₂C₆H₅ | CO₂H | CH₂ | O | O | 3 | 1 | 1 |
| 56 | ![imidazoline] | H | CH₃ | COCH₃ | CO₂H | CH₂ | O | — | 3 | 1 | 1 |
| 57 | ![methyl azepane] | CH₂OCH₃ | CH₂C₆H₅ | COC₂H₅ | CO₂C₂H₅ | CH₂ | CH₂ | CH₂ | 4 | 2 | 1 |
| 58 | ![methyl quinuclidine] | (CH₂)₂C₆H₅ | ![naphthylmethyl] | COCH₂CH(CH₃)₂ | COCH₃ | CH₂ | CH₂ | — | 5 | 3 | 1 |
| 59 | H₅C₆—H₂C—![azetidine]-N | H | (CH₂)₂OCH₂CH₃ | (CH₂)₂C₆H₅ | C(=S)—OH | CH₂ | O | CH₂ | 2 | 2 | 2 |
| 60 | CH₃NHC(=NH)— | ![cyclohexyl] | H | CO(CH₂)₂OCH₃ | C(=O)—O—C(=O)—C(CH₃)₃ | CH₂ | CH₂ | — | 3 | 1 | 1 |

-continued $$R^1-(CH_2)_m-X-Y-Z-\underset{\substack{|\\(CH_2)_m\\|\\R^2}}{\overset{\substack{R^3\\|\\}}{C}}-\underset{\substack{|\\R^5}}{\overset{\substack{R^4\\|\\N-(CH_2)_p}}{}}$$
(with phenyl ring between Z and the chain)

| Example | R¹ | R² | R³ | R⁴ | R⁵ | X | Y | Z | m | n | p |
|---------|----|----|----|----|----|----|----|----|----|----|----|
| 61 | (2-methyl-6-methyl-piperidin-3-one, HN in ring) | —CH₂—C₆H₅ | C₄H₉ | COO(CH₂)₂C₆H₅ | CO₂CH(CH₃)₂ | CH₂ | O | — | 2 | 3 | 1 |
| 62 | (3-methyl-5,6,7,8-tetrahydroquinoline) | CH₂CH₂CF₃ | (CH₂)₂SO₂CH₃ | CH₂SO₂CH₂C₂H₅ | P(OH)₂=O | CHOH | O | — | 3 | 1 | 1 |
| 63 | (6-methyl-5,6,7,8-tetrahydroquinoline) | H | (CH₂)₂CN | H | CONHCH₂CO₂CH₃ | NH | C=O | — | 0 | 6 | 2 |
| 64 | (N-cyano-guanidine: H₂N—C(=N-CN)—NH—) | C₆H₁₃ | (CH₂)₂NO₂ | C₆H₅ (phenyl) | C(=S)—O—CH₂C₂H₅ | NCH₃ | C=S | — | 2 | 0 | 10 |
| 65 | (5-methyl-1,2,4-triazole, NH) | CF₂CF₃ | CF₂CF₃ | (pyridin-3-yl) | (5-methyl-tetrazole, NH) | O | CH₂ | — | 3 | 1 | 1 |
| 66 | (azonan-2-one, HN in ring) | (4-pyridyl) | (CH₂)₂NHCH₃ | (oxazol-4-yl) | (pyrrol-2-yl, NH) | SO₂ | CH=CH | — | 1 | 2 | 3 |

-continued $$R^1-(CH_2)_m-X-Y-Z-\underset{\underset{R^5}{|}}{\overset{\overset{R^3}{|}}{\underset{(CH_2)_p}{C}}}-\overset{R^4}{\underset{R^5}{N}}$$

| Example | R$^1$ | R$^2$ | R$^3$ | R$^4$ | R$^5$ | X | Y | Z | m | n | p |
|---|---|---|---|---|---|---|---|---|---|---|---|
| 67 | piperazinyl (HN-N-) | methylcyclopentyl (CH$_3$ substituted cyclopentyl) | (CH$_2$)$_4$SCH$_2$CH$_3$ | COCH$_2$C$_6$H$_5$ | $-\overset{O}{\underset{\|}{P}}-OH$ | CH$_2$ | C=S | CH$_2$ | 4 | 2 | 1 |
| 68 | 2-azabicyclic with methyl | methylthiophene-CH$_2$ | (CH$_2$)$_4$-(3-pyridyl) | furan-2-CH$_2$ | $-\overset{O}{\underset{\|}{P}}-(OH)_2$ | C=O | O | — | 3 | 3 | 0 |
| 69 | 4-methyl-3-methoxy-1-(CH$_3$CON)-piperidinyl | CH$_2$SC$_6$H$_5$ | (CH$_2$)$_3$CO$_2$CH$_3$ | COC$_3$H$_7$ | $-C(=O)-O-C(=O)-CH_3$ | C=S | NHCH$_3$ | — | 4 | 1 | 3 |
| 70 | C$_6$H$_5$CH$_2$NHC(=NH)— | CH$_2$CH$_2$SO$_2$CH$_3$ | (CH$_2$)$_2$CO$_2$H | COC$_6$H$_5$ | $-C(=O)-O-C_2H_5$ | CH$_2$ | C=S | — | 3 | 4 | 1 |
| 71 | 1-methylazetidinyl | CH$_2$CH$_2$NHCH$_3$ | (CH$_2$)$_3$NH(CH$_2$)$_2$OCH$_3$ | COOC$_{10}$H$_{21}$ | C$_6$H$_5$ | CH$_2$ | SO$_2$ | CH$_2$ | 2 | 2 | 2 |
| 72 | 2,5-dimethylpyridinyl | CH$_3$ | 1-methyl-3-methylpyrrolidinyl | H | CO$_2$H | CH$_2$ | NCOCH$_3$ | — | 1 | 1 | 1 |

-continued

Structure:

$R^1-(CH_2)_m-X \overset{Y-Z}{\underset{}{\bigcirc}} (CH_2)_n-C(R^2)(R^3)-N(R^4)-(CH_2)_p-R^5$

| Example | R¹ | R² | R³ | R⁴ | R⁵ | X | Y | Z | m | n | p |
|---|---|---|---|---|---|---|---|---|---|---|---|
| 73 | 2-(CH₂C₆H₅)-pyrrolidin-1-yl | C₂H₅ | 3-methyl-4-methylpyridinyl (H₃C—) | (CH₂)₂CO₂H | $\overset{O}{\underset{}{\|}}$P(OH)₂ | O | C=O | O | 3 | 2 | 1 |
| 74 | C₂H₅NH—C(=N—CH₂C₆H₅)—NH— | C₃H₇ | 4-methyloxazolyl | —C(=O)(CH₂)₃SO₂CH₃ | COOC₂H₅ | CH₂ | SO₂ | CH₂ | 1 | 0 | 4 |
| 75 | 2-(FH₂C-CH₂)-piperidinyl (NH) | C₄H₉ | C₃H₇ | —C(=S)—CH(CH₂C₆H₅)CH₃ | C(=O)—O—C(=O)—OC₄H₉ | CH₂ | CH₂ | O | 3 | 1 | 3 |
| 76 | 3-methyl-4-methyl-pyrrolidin-1-yl (HN) | CH₂C₆H₅ | C₁₀H₂₁ | 2-(F₃C)C₆H₄—COCH₂— | CONHCH(CH₃)CO₂H | CH=CH | CH₂ | — | 2 | 2 | 2 |
| 77 | C₆H₅—NH— | (CH₂)₂C₆H₅ | (CH₂)₃—SO₂—C₆H₅ | CH₂(CH₂)₂CO₂CH₃ | —COOC₆H₅ | CH₂ | —C≡C— | — | 1 | 2 | 4 |
| 78 | H₃C—C(CH₃)(CHF₂)—N— | (CH₂)₂C₆H₅ | CH₂CH₂F | —C(=O)—(CH₂)₂OCH₃ | —P(=O)(OH)₂ | —C≡C— | CH₂ | O | 4 | 2 | 1 |

-continued
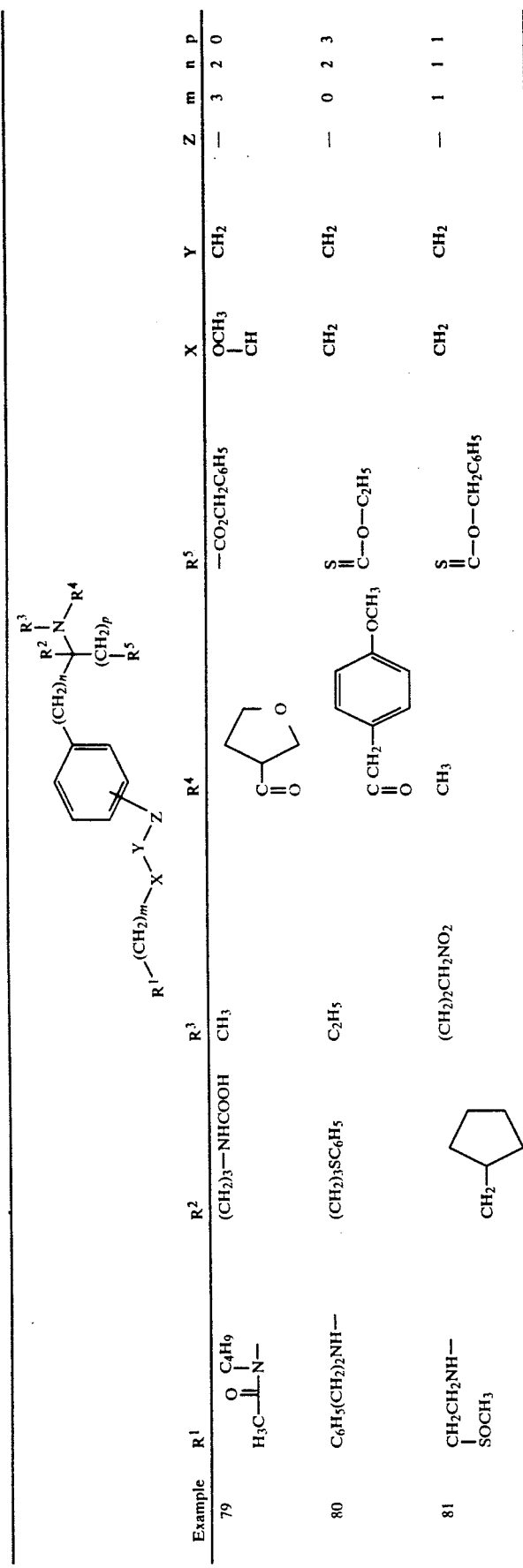
| Example | R¹ | R² | R³ | R⁴ | R⁵ | X | Y | Z | m | n | p |
|---|---|---|---|---|---|---|---|---|---|---|---|
| 79 | $H_3C-\overset{O}{\underset{\|}{C}}-\underset{\|}{N}-$ $C_4H_9$ | $(CH_2)_3-NHCOOH$ | $CH_3$ | tetrahydrofuran-3-yl (C=O) | $-CO_2CH_2C_6H_5$ | $\overset{OCH_3}{\underset{\|}{CH}}$ | $CH_2$ | — | 3 | 2 | 0 |
| 80 | $C_6H_5(CH_2)_2NH-$ | $(CH_2)_3SC_6H_5$ | $C_2H_5$ | 4-methoxybenzoyl | $\underset{\|}{\overset{S}{C}}-O-C_2H_5$ | $CH_2$ | $CH_2$ | — | 0 | 2 | 3 |
| 81 | $CH_2CH_2NH-$ $\|$ $SOCH_3$ | cyclopentyl-CH₂ | $(CH_2)_2CH_2NO_2$ | $CH_3$ | $\underset{\|}{\overset{S}{C}}-O-CH_2C_6H_5$ | $CH_2$ | $CH_2$ | — | 1 | 1 | 1 |

The test procedures employed to measure the antiplatelet aggregating activity of the compounds of the present invention are described below.

EXAMPLE 82

Blood was drawn into 0.1 volumes of acidcitrate-dextrose (85 mM sodium citrate, 64 mM citric acid, 110 mM dextrose) by venipuncture from normal human volunteers. Platelet-rich plasma was prepared by centrifugation at 400× g for 12 minutes. PGE1 (5 mg/ml) was added and platelets were collected by centrifugation at 800× g for 12 minutes. The platelet pellet was resuspended into human platelet buffer (140 mM NaCl, 7.9 mM KCl, 3.3 mM Na$_2$HPO$_4$, 6 mM HEPES, 2% bovine serum albumin, 0.1% destrose, pH 7.2) and filtered over Sepharose 2B that was previously equilabrated in human platelet buffer. Platelets were counted and adjusted to 2×108/ml with human platelet buffer. Human fibrinogen (10–100 mg/ml and CaCl$_2$ (1 mM) were added and aggregation was initiated by the addition of 10 mM ADP. Aggregation was monitored by the initial rate of increase of light transmittance.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of clotting disorders or emboli, or for other indications for the compounds of the invention indicated above. Likewise, the specific pharmacological responses observed may vary acording to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

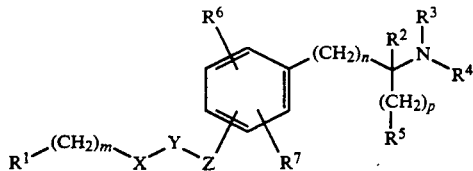

or a pharmaceutically acceptable salt thereof, wherein R$^1$ is

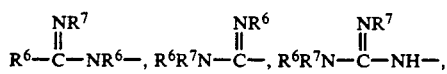

NR$^6$R$^7$ wherein R$^6$ and R$^7$ are independently
hydrogen,
C$_{1-10}$ alkoxycarbonyl or unsubstituted or substituted C$_{1-10}$ alkyl and cycloalkyl wherein said substituents are
C$_{1-10}$ alkoxy,
C$_{1-10}$ alkoxyalkyl,
C$_{1-10}$ alkoxyalkyloxy,
C$_{1-10}$ alkoxycarbonyl,
C$_{1-10}$ alkylcarbonyl,
C$_{1-6}$ alkylaminocarbonyl,
C$_{1-10}$ aralkylcarbonyl,
C$_{1-10}$ alkylthiocarbonyl,
C$_{4-10}$ aralkylthiocarbonyl,
thiocarbonyl,
C$_{1-10}$ alkoxythiocarbonyl,
phenyl,
C$_{1-4}$ alkanoylamino,
C$_{1-6}$ alkoxycarbonyl-C$_{1-6}$ alkylamino,
C$_{1-10}$ alkylsulfonylamino,
C$_{4-10}$ arlkylsulfonylamino,
C$_{4-10}$ aralkyl,
C$_{1-10}$ alkylthio,
C$_{4-10}$ aralkylthio,
C$_{1-10}$ alkylsulfinyl,
C$_{4-10}$ aralkylsulfinyl,
C$_{1-10}$ alkylsulfonyl,
C$_{4-10}$ aralkylsulfonyl,
aminosulfonyl,
C$_{1-10}$ alkylaminosulfonyl,
C$_{4-10}$ aralkylsulfonylamino,
oxo,
unsubstituted or mono- or di-substituted 1-ethenyl, 2-ethenyl or 3-propenyl wherein said substituents are selected from the group consisting of hydrogen, C$_{1-10}$ alkyl and C$_{7-10}$ aralkyl,
carboxy,
hydroxy,
amino,
C$_{1-6}$ alkylamino
C$_{1-6}$ dialkylamino
halogen, where halogen is defined as Cl, F, Br, or I,
nitro, or
cyano,
and further wherein said N can additionally be substituted to form a quaternary ammonium ion wherein said substituent is as previously defined for R$^6$ and R$^7$;
R$^2$ and R$^3$ are independently hydrogen, phenyl, naphthyl unsubstituted or substituted C$_{1-10}$ alkyl or cycloalkyl wherein said substituent is
C$_{1-10}$ alkoxyalkyl,
phenyl
C$_{4-10}$ aralkyl,
carboxy,
C$_{1-10}$ alkylcarbonyl,
C$_{1-10}$ alkylthiocarbonyl,
C$_{4-10}$ aralkylcarbonyl,
C$_{4-10}$ aralkylthiocarbonyl,
C$_{1-6}$ alkoxycarbonyl,
C$_{4-10}$ aralkoxycarbonyl,
C$_{1-6}$ alkoxy,
C$_{4-10}$ aralkoxy,
C$_{1-6}$ alkylamino,
C$_{1-12}$ dialkylamino,
C$_{1-6}$ alkanoylamino,
C$_{4-12}$ aralkanoylamino,
C$_{4-10}$ aralkylamino;
R$^4$ is
hydrogen,
phenyl
C$_{1-10}$ alkyl or cycloalkyl
C$_{4-10}$ aralkyl, arylcarbonyl, aminocarbonyl,
$C_{1-10}$ alkylcarbonyl, $C_{1-6}$ alkylaminocarbonyl,
$C_{1-10}$ alkylthiocarbonyl, $C_{1-6}$ dialkylaminocarbonyl,
$C_{1-10}$ alkylthiocarbonyl,
aryl$C_{1-6}$alkylaminocarbonyl,
$C_{1-10}$ alkoxycarbonyl,
$C_{4-10}$ aralkylcarbonyl,
$C_{4-10}$ aralkoxycarbonyl,
$C_{1-10}$ carboxylalkyl and
further wherein any of the substituents for $R^4$ may be substituted by one or more substituents selected from the group as defined for $R^6$, or an L- or D-amino acid joined by an amide linkage;
$R^5$ is

wherein $R^8$ is
hydroxy,
$C_{1-10}$ alkyloxy,
$C_{4-10}$ aralkyloxy,
$C_{4-10}$ aralkylcarbonyloxy,
$C_{1-10}$ alkoxyalkyloxy,
$C_{1-10}$ alkoxylalkylcarbonyloxy,
$C_{1-10}$ alkoxycarbonyloxyalkyl,
$C_{1-10}$ alkylcarbonyloxyalkyloxy,
an L- or D-amino acid joined by an amide linkage, and wherein the carboxylic acid moiety of said amino acid is as the free acid or is esterified by $C_{1-6}$alkyl,

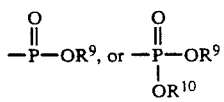

wherein $R^9$ and $R^{10}$ are selected from the group consisting of hydrogen, $C_{1-10}$ alkyl and $C_{4-10}$ aralkyl;
X and Y are independently
$NR^6$,
O,

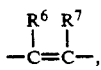

—C≡C—,
unsubstituted or substituted $C_{1-15}$ alkyl or cycloalkyl wherein said substituents are independently $R^6$ and $R^7$,

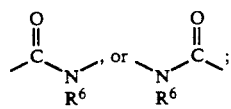

Z is an optional substitutent that, when present, is independently chosen as defined by X and Y;
m is an integer of from zero to ten;
n is an integer of from zero to ten; and
p is an integer of from zero to three;
wherein aryl is phenyl or naphthyl.

2. A compound of claim 1, having the structural formula

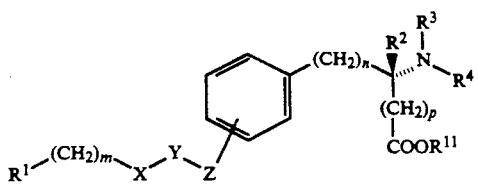

or a pharmaceutically acceptable salt thereof, wherein
$R^1$ is
  $NR^6R^7$ wherein $R^6$ and $R^7$ are independently hydrogen,
  $C_{1-10}$ alkoxycarbonyl or unsubstituted or substituted $C_{1-10}$ alkyl wherein said substitutent is
    $C_{1-10}$ alkoxy,
    $C_{1-10}$ alkoxycarbonyl,
    phenyl,
    $C_{4-10}$ aralkyl,
    carboxy,
    hydroxy or
    amino,

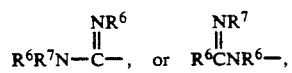

and further wherein said N can additionally be substituted to form a quaternary ammonium ion;
$R^2$ and $R^3$ are independently
  hydrogen
  $C_{1-10}$ alkyl,
  $C_{4-10}$ aralkyl;
$R^4$ is
  hydrogen,
  $C_{1-10}$ alkyl,
  $C_{4-10}$ aralkyl,
  phenylcarbonyl,
  aralkylcarbonyl
  $C_{1-10}$ alkylcarbonyl,
  $C_{1-10}$ alkoxycarbonyl, or
  $C_{4-10}$ aralkoxycarbonyl
  and further wherein any of the substituents for $R^4$ may be substituted by one or more substituents from the group defined as $R^6$ in claim 40;
$R^{11}$ is
  hydrogen or
  $C_{1-10}$ alkyl;
X and Y are independently
  O,
  —CH=CH—

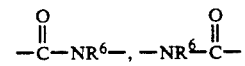

unsubstituted or substituted $C_{1-15}$ straight or branched alkyl either substituted or unsubstituted with
  carboxy,
  hydroxy, or
  $C_{1-10}$ alkoxy;
Z is an optional substitutent that, when present, is O, —$NR^6CO$—, —$CONR^6$,

or $C_{1-10}$ straight or branched alkyl;

m is an integer of from zero to six;

n is an integer of from zero to six; and p is an integer of from zero to three;

wherein aryl is phenyl or naphthyl.

3. A compound of claim 2, having the structural formula

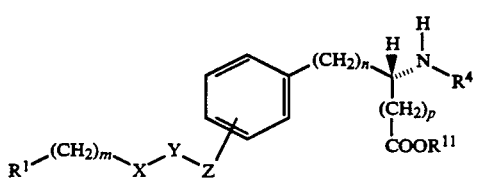

or a pharmaceutically acceptable salt thereof, wherein $R^1$ is

NR$^6$R$^7$ wherein R$^6$ and R$^7$ are independently hydrogen, unsubstituted or substituted $C_{1-10}$ alkyl wherein said substituent is $C_{1-10}$ alkoxycarbonyl, phenyl, $C_{1-10}$ aralkyl,

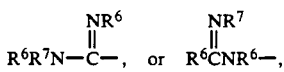

and further wherein said N can additionally be substituted to form a quaternary ammonium ion;

$R^4$ is phenylcarbonyl, $C_{1-10}$ alkylcarbonyl, $C_{1-10}$ alkyloxycarbonyl, $C_{4-10}$ aralkylcarbonyl, or $C_{4-10}$ aralkoxylcarbonyl, and further wherein the substituents for $R^4$ may be unsubstituted by one or more substituents from the group defined as $R^6$ in claim 1;

$R^{11}$ is hydrogen or $C_{1-10}$ alkyl;

X and Y are independently

O, NR$^6$CO—, —CONR$^6$—,

—CH=CH—, unsubstituted or substituted $C_{1-15}$ straight or branched alkyl wherein said substituent is hydroxy;

Z is an optional substituent that, when present, is

O or $C_{1-10}$ straight or branched alkyl;

m is an integer of from zero to six;

n is an integer of from zero to six; and p is an integer of from zero to three;

wherein aryl is phenyl or naphthyl.

4. A compound of claim 3, having the structural formula

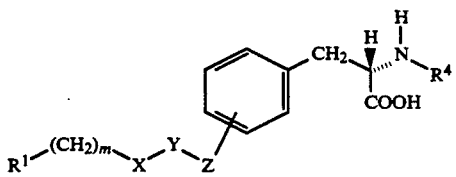

or a pharmaceutically acceptable salt thereof, wherein $R^1$ is NR$^6$R$^7$ wherein R$^6$ and R$^7$ are independently hydrogen or $C_{1-10}$ alkyl;

$R^4$ is phenylcarbonyl, $C_{1-10}$ alkylcarbonyl, $C_{4-10}$ aralkylcarbonyl, $C_{1-10}$ alkoxycarbonyl, $C_{4-10}$ aralkoxycarbonyl, and further wherein any of the substituents for $R^4$ may be substituted by one or more substituents from the group defined as $R^6$ in claim 1.

X and Y are independently

O,

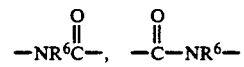

—CH=CH— or $C_{1-10}$ straight or branched alkyl;

Z is an optional substituent that, when present, is

O or $C_{1-5}$ straight or branched alkyl; and m is an integer of from zero to six;

wherein aryl is phenyl or naphthyl.

5. A compound of claim 1, or a pharmaceutically acceptable salt thereof, selected from the group consisting of:

2-S-(N-Benzyloxycarbonylamino)-[4-(3-t-butylamino-propyloxy)phenyl]propionic acid;

2-S-(N-t-Butyloxycarbonylamino)-[4-(3-N-t-butylamino-propyloxy)phenyl]propionic acid;

2-S-(N-Benzyloxycarbonylamino)-3-[4-(N,N,2,2-tetra-methyl-1,3-propanediamino)propyloxyphenyl]-propionic acid;

2-S-(N-Benzyloxycarbonylamino)-[4-(3-N-methyl-N-benzylamino)propyloxyphenyl]propionic acid;

2-S-(N-Benzyloxycarbonylamino)-3-[4-(1,1,3,3-tetramethylbutylamino)propyloxyphenyl]propionic acid;

2-S-(N-Benzyloxycarbonylamino)-3-[4-(6-aminohexyloxyphenyl)]propionic acid hydrochloride;

2-S-(N-Benzyloxycarbonylamino)-3-[4-(7-aminoheptyloxy)phenyl]propionic acid hydrochloride;

2-S-(N-Benzyloxycarbonylamino)-3-[4-(8-aminooctyloxy)phenyl]propionic acid;

2-S-(N-Benzyloxycarbonylamino)-3-[4-(5-aminopentyloxy)phenyl]propionic acid hydrochloride;

2-S-(N-Phenylcarbonylamino)-3-[4-(6-aminohexyloxyphenyl)]propionic acid hydrochloride;

2-S-(N-Phenethylcarbonylamino)-3-[4-(6-aminohexyloxyphenyl)]propionic acid hydrochloride;

2-S-(2-Carboxyphenylacetylamino)-3-[4-(6-aminohexyloxy)phenyl]propionic acid hydrochloride;

2-S-(Phenylacetylamino)-3-[4-(6-aminohexyloxyphenyl)]propionic acid;

2-S-(2-Carboxy-3-phenylpropionylamino)-3-[4-(6-aminohexyloxy)phenyl]propionic acid;

2-S-(Hexanoylamino)-3-[4-(6-aminohexyloxy)phenyl]propionic acid Hydrochloride;

2-S-(2-Naphthanoylamino)-3-[4-(6-aminohexyloxy)phenyl]propionic acid;

2-S-(Butanoylamino)-3-[4-(6-aminohexyloxy)phenyl]propionic acid;

2-S-(Heptanoylamino)-3-[4-(6-aminohexyloxy)phenyl]propionic acid hydrochloride;

2-S-(5-Phenylpentanoylamino)-3-[4-(6-aminohexyloxy)phenyl]propionic acid hydrochloride;

2-S-(3-Carboxypropanoyl)amino-3-[4-(6-aminohexyloxy)phenyl]propionic acid hydrochloride;

2-S-(Acetylamino)-3-[4-(6-aminohexyloxy)phenyl]propionic acid hydrochloride;

2-S-(N-t-Butyloxycarbonylamino)-3-[4-(4-t-butylamino-butyl)phenyl]propionic acid;

2-S-(5-Aminopentanoyl)amino-3-[4-(6-aminohexyloxy)phenyl]propionic acid dihydrochloride;

2-S-(4-Carboxybutanoylamino-3-[4-(6-aminohexyloxy)phenyl]propionic acid; and

Methyl 2-S-(N-Benzyloxycarbonylamino-3-[4-(2,6-dimethylpiperazin-4-yl)butyloxyphenyl]propionate.

6. A method of blocking fibrinogen from acting at its receptor site in a mammal, comprising the step of administering to said mammal a pharmacologically effective amount of a compound as claimed in claim 1.

7. A method of preventing thrombus and embolus formation in a mammal in need thereof, comprising the step of administering to said mammal a pharmacologically effective amount of a compound as claimed in claim 1.

8. A method of treating thrombus and embolus formation in a mammal in need thereof, comprising the step of administering to said mammal a pharmacologically effective amount of a compound as claimed in claim 1.

9. A method of inhibiting aggregation of blood platelets in a mammal in need thereof, comprising the step of administering to said mammal a pharmacologically effective amount of a compound as claimed in claim 1.

10. A composition for inhibiting the aggregation of blood platelets in a mammal, comprising a compound of claim 1 and a pharmaceutically acceptable carrier.

11. The compounds of claim 1 for use in inhibiting the binding of fibrinogen to blood platelets, inhibiting the aggregation of blood platelets, treating thrombus formation or embolus formation, or preventing thrombus or embolus formation in a mammal.

12. The compounds of claim 2 for use in inhibiting the binding of fibrinogen to blood platelets, inhibiting the aggregation of blood platelets, treating thrombus formation or embolus formation, or preventing thrombus or embolus formation in a mammal.

13. The compounds of claim 3 for use in inhibiting the binding of fibrinogen to blood platelets, inhibiting the aggregation of blood platelets, treating of thrombus formation or embolus formation, or preventing thrombus or embolus formation in a mammal.

14. The compounds of claim 4 for use in inhibiting the binding of fibrinogen to blood platelets, inhibiting the aggregation of blood platelets, treating thrombus formation or embolus formation, or preventing thrombus or embolus formation in a mammal.

15. The compounds of claim 8 for use in inhibiting the binding of fibrinogen to blood platelets, inhibiting the aggregation of blood platelets, treating of thrombus formation or embolus formation, or preventing thrombus or embolus formation in a mammal.

16. A pharmaceutical composition for inhibiting the aggregation of blood platelets comprising an effective amount of a compound as claimed in claim 1, and a pharmaceutically acceptable carrier.

* * * * *